(12) United States Patent
Plettenburg et al.

(10) Patent No.: US 8,541,449 B2
(45) Date of Patent: Sep. 24, 2013

(54) SUBSTITUTED ISOQUINOLINES AND ISOQUINOLINONES AS RHO KINASE INHIBITORS

(75) Inventors: Oliver Plettenburg, Frankfurt am Main (DE); Katrin Lorenz, Frankfurt am Main (DE); John Weston, Frankfurt am Main (DE); Matthias Loehn, Frankfurt am Main (DE); Heinz-Werner Kleemann, Frankfurt am Main (DE); Olivier Duclos, Paris (FR); Frederic Jeannot, Paris (FR)

(73) Assignee: Sanofi, Paris (FR)

( * ) Notice: Subject to any disclaimer, the term of this patent is extended or adjusted under 35 U.S.C. 154(b) by 131 days.

(21) Appl. No.: 13/000,754

(22) PCT Filed: Jun. 19, 2009

(86) PCT No.: PCT/EP2009/004421
§ 371 (c)(1),
(2), (4) Date: Apr. 20, 2011

(87) PCT Pub. No.: WO2009/156100
PCT Pub. Date: Dec. 30, 2009

(65) Prior Publication Data
US 2011/0190341 A1 Aug. 4, 2011

Related U.S. Application Data

(60) Provisional application No. 61/153,149, filed on Feb. 17, 2009.

(30) Foreign Application Priority Data

Jun. 24, 2008 (EP) .................................... 08290606

(51) Int. Cl.
*C07D 217/24* (2006.01)
*A61K 31/472* (2006.01)

(52) U.S. Cl.
USPC .......................................... 514/309; 546/141

(58) Field of Classification Search
None
See application file for complete search history.

(56) References Cited

U.S. PATENT DOCUMENTS

| | | | |
|---|---|---|---|
| 5,480,883 A | 1/1996 | Spada et al. | |
| 6,903,107 B1 | 6/2005 | Timmers et al. | |
| 7,217,722 B2 | 5/2007 | Takami et al. | |
| 7,618,985 B2 | 11/2009 | Ray et al. | |
| 2003/0220368 A1 | 11/2003 | Ozaki et al. | |
| 2004/0138286 A1 | 7/2004 | Imazaki et al. | |
| 2006/0079556 A1 | 4/2006 | Sher et al. | |
| 2007/0060595 A1 | 3/2007 | Yoshizawa et al. | |
| 2008/0045566 A1 | 2/2008 | Ray et al. | |
| 2008/0242699 A1 | 10/2008 | Plettenburg et al. | |
| 2009/0088429 A1 | 4/2009 | Plettenburg et al. | |
| 2009/0093518 A1 | 4/2009 | Plettenburg et al. | |
| 2010/0056518 A1 | 3/2010 | Plettenburg et al. | |
| 2010/0056553 A1 | 3/2010 | Plettenburg et al. | |
| 2010/0056566 A1 | 3/2010 | Plettenburg et al. | |
| 2010/0056568 A1 | 3/2010 | Plettenburg et al. | |
| 2010/0063025 A1 | 3/2010 | Plettenburg et al. | |
| 2010/0081671 A1 | 4/2010 | Plettenburg et al. | |
| 2010/0105650 A1 | 4/2010 | Plettenburg et al. | |

FOREIGN PATENT DOCUMENTS

| | | |
|---|---|---|
| EP | 1403255 | 3/2004 |
| EP | 1541559 | 6/2005 |
| EP | 1550660 | 7/2005 |
| FR | 2485537 | 6/1980 |
| JP | 10087629 A | 4/1998 |
| WO | 9202476 | 2/1992 |
| WO | 9706802 | 2/1997 |
| WO | 9723214 | 7/1997 |
| WO | WO98/06433 | 2/1998 |
| WO | 9911642 | 3/1999 |
| WO | 0024718 | 5/2000 |
| WO | 0073299 | 12/2000 |
| WO | WO01/39726 A2 | 6/2001 |
| WO | 0153288 | 7/2001 |
| WO | 0156988 | 8/2001 |
| WO | 0164656 | 9/2001 |
| WO | WO01/64238 A2 | 9/2001 |
| WO | 0177101 | 10/2001 |
| WO | 0192227 | 12/2001 |
| WO | 0234712 | 5/2002 |

(Continued)

OTHER PUBLICATIONS

Bonjoch, J. et al., "A New Synthetic Entry to the Tricyclic Skeleton of FR901483 by Palladium-Catalyzed Cyclization of Vinyl Bromides with Ketone Enolates" Tetrahedron Letters (2003) pp. 8387-8390, vol. 44.
Takami, A. et al., "Design and Synthesis of Rho Kinase Inhibitors (I)" Bioorganic & Medicinal Chemistry (2004) pp. 2115-2137, vol. 12.
Iwakubo, M. et al., "Design and Synthesis of Rho Kinase Inhibitors (III)" Bioorganic & Medicinal Chemistry (2007) pp. 1022-1033, vol. 15.
Forzato, C. et al., "Baker's yeast reduction of 4-hetero-2-(2-nitroethyl)cyclohexanones" Tetrahedron: Asymmetry (1997) pp. 1811-1820, vol. 8.
Tamura, M. et al., "Development of Specific Rho-Kinase Inhibitors and Their Clinical Application" Biochimica et Biophysica Acta (2005) pp. 245-252, vol. 1754.
Becker, D.P. et al., "A Short Synthesis of 1-Azaadamantan-4-one and the 4r and 4s Isomers of 4-Amino-1-azaadamantane" Synthesis (1992) pp. 1080-1082, vol. 11.
U.S. Appl. No. 12/970,376, filed Dec. 16, 2010, Inventor: Plettenburg, et al, entitled: "6-Substituted Isoquinolines and Isoquinolinones".

(Continued)

*Primary Examiner* — Zinna Northington Davis
(74) *Attorney, Agent, or Firm* — Scully, Scott, Murphy & Presser, P.C.

(57) ABSTRACT

The invention relates to substituted isoquinoline and isoquinolinones of the formula (I) useful for the treatment and/or prevention of diseases associated with Rho-kinase and/or Rho-kinase mediated phosphorylation of myosin light chain phosphatase, and compositions containing such compounds.

(I)

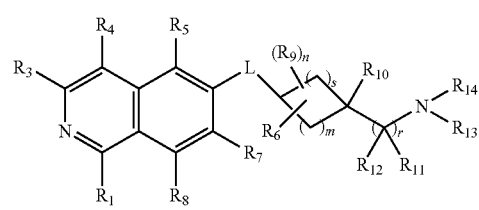

50 Claims, No Drawings

(56) References Cited

FOREIGN PATENT DOCUMENTS

| WO | 02055496 | 7/2002 |
|---|---|---|
| WO | 02076457 | 10/2002 |
| WO | 02088101 | 11/2002 |
| WO | 03018556 | 3/2003 |
| WO | 03024450 | 3/2003 |
| WO | WO03/053330 A2 | 7/2003 |
| WO | 2004113297 | 12/2004 |
| WO | WO2004/106325 A1 | 12/2004 |
| WO | 2005035933 | 2/2005 |
| WO | 2005035516 | 4/2005 |
| WO | WO2005/030130 A2 | 4/2005 |
| WO | WO2005/030791 A2 | 4/2005 |
| WO | 2005054202 | 6/2005 |
| WO | 2005074535 | 8/2005 |
| WO | 2005087226 | 9/2005 |
| WO | 2005095362 | 10/2005 |
| WO | WO2007/012421 A1 | 2/2007 |
| WO | WO2007/012422 A1 | 2/2007 |
| WO | 2007039563 A1 | 4/2007 |
| WO | 2007065916 | 6/2007 |
| WO | 2008020081 | 2/2008 |
| WO | WO2008/020081 | 2/2008 |
| WO | WO2008/077556 | 7/2008 |
| WO | 2008077555 A2 | 6/2011 |

OTHER PUBLICATIONS

U.S. Appl. No. 13/000,202, filed Dec. 20, 2010, Inventor: Plettenburg et al., entitled: "Bi- and Polycyclic Substituted Isoquinoline and Isoquinolinone Derivatives".
Iwakubo, Masayuki et al., "Design and synthesis of Rho kinase inhibitors (II)," Bioorganic and Medicinal Chemistry (2007), vol. 15, pp. 350-364.
Alvarez, M. et al., "Product Class 5: Isoquinolines," Science of Synthesis (2005), vol. 15, pp. 661-838.
Alvarez, M. et al., "Product Class 6: Isoquinolinones," Science of Synthesis (2005), vol. 15, pp. 839-906.
Al, Shingo et al., "Rho-Rho kinase is involved in smooth muscle cell migration through myosin light chain phosphorylation-dependent and independent pathways," Atherosclerosis (2001), vol. 155, pp.321-327.
Bauer, Markus et al., "Dichotomous Regulation of Myosin Phosphorylation and ShapeChange by Rho-Kinase and Calcium in Intact Human Platelets," Blood (1999), vol. 94, pp. 1665-1672.
Chellaiah, Meenakshi A. et al., "Rho-dependent Rho Kinase Activation Increases CD44 Surface Expression and Bone Resorption in Osteoclasts," The Journal of Biological Chemistry (2003), vol. 278, pp. 29086-29097.
Chitaley, Kanchan et al., "Antagonism of Rho-kinase stimulates rat penile erection via a nitric oxide-independent pathway," Nature Medicine (2001), vol. 7, pp. 119-122.
Maruoka, Shuichiro et al., "Elastase Anti-elastase imbalance in the Pathogenesis of COPD," Nippon Rinsho (1999), vol. 57, pp. 1982-1987.
Degraffenreid, Michael R. et al., "An Efficient and Scalable One-Pot Double Michael Addition-Dieckmann Condensation for the Synthesis of 4,4-Disubstituted Cyclohexane β-Keto Esters," Journal of Organic Chemistry (2007), vol. 72, pp. 7455-7458.
Demiryürek, Seniz et al.,"Effects of fasudil, a Rho-kinase inhibitor, on myocardial preconditioning in anesthetized rats," European Journal of Pharmacology (2005), vol. 527, pp. 129-140.
Retzer, Michaela et al., "Mildly oxidised low density lipoprotein induces platelet shape change via Rho-kinase-dependent phosphorylation of myosin light chain and moesin," FEBS Letters (2000), vol. 466, pp. 70-74.
Kimura, Kazushi et al., "Regulation of the Association of Adducin with Actin Filaments by Rho-associated Kinase (Rho-kinase) and Myosin Phosphatase," The Journal of Biological Chemistry (1998), vol. 273, pp. 5542-5548.
Fukumoto, Y. et al., "Acute vasodilator effects of a Rho-kinase inhibitor, fasudil, in patients with severe pulmonary hypertension," Heart (2005), vol. 91, pp. 391-392.

Gingras, Denis et al., "Tyrosine phosphorylation of the vascular endothelial-growth-factor receptor-2 (VEGFR-2) is modulated by Rho proteins," Biochemical Journal (2000), vol. 348, pp. 273-280.
Gokina, Natalia I. et al., "Effects of Rho kinase inhibition on cerebral artery myogenic tone and reactivity," Journal of Applied Physiology (2005), vol. 98, pp. 1940-1948.
Yoshida, Yoshiki et al., "Studies on Anti-*Helicobacter pylori* Agents. Part 1: Benzyloxyisoquinoline Derivatives," Bioorganic and Medical Chemistry (1999), vol. 7, pp. 2647-2666.
Hara, Masahito et al., "Protein kinase inhibition by fasudilhydrochloride promotes neurological recovery after spinal cord injury in rats," Journal of Neurosurgery: Spine 1 (2000), vol. 93, pp. 94-101.
Hattori, Tsuyoshi et al., "Long-Term Inhibition of Rho-Kinase Suppresses Left Ventricular Remodeling After Myocardial Infarction in Mice," Circulation (2004), vol. 109, pp. 2234-2239.
Hitomi, Asako et al., "Hemorheological abnormalities in experimental cerebral ischemia and effects of protein kinase inhibitor on blood fluidity," Life Sciences (2000), vol. 67, pp. 1929-1939.
Honjo, Megumi et al., "Effects of Rho-Associated Protein Kinase Inhibitor Y-27632 on Intraocular Pressure and Outflow Facility," Investigative Ophthalmology and Visual Science (2001), vol. 42, pp. 137-144.
Inoue, Makoto et al., "Initiation of neuropathic pain requires lysophosphatidic acid receptor signaling," Nature Medicine (2004), vol. 10, pp. 712-718.
Itoh, Kazuyuki et al., "An essential part for Rho-associated kinase in the transcellular invasion of tumor cells," Nature Medicine (1999), vol. 5, pp. 221-225.
Kawaguchi, Atsuhiro et al., "The effect of a Rho kinase inhibitor Y-27632 on superoxide production, aggregation and adhesion in human polymorphonuclear leukocytes," European Journal of Pharmacology (2000), vol. 403, pp. 203-208.
Kim, Inkyeom et al., "Thin and Thick Filament Regulation of Contractility in Experimental Cerebral Vasospasm," Neurosurgery (2000), vol. 46, pp. 440-447.
Amano, Mutsuki et al., "Formation of Actin Stress Fibers and Focal Adhesions Enhanced by Rho-Kinase," Science (1997), vol. 275, pp. 1308-1311.
Kishi, Takuya et al., "Rho-Kinase Inhibitor Improves Increased Vascular Resistance and Impaired Vasodilation of the Forearm in Patients with Heart Failure," Circulation (2005), vol. 111, pp. 2741-2747.
Klages, Birgit et al., "Activation of $G_{12}/G_{13}$ Results in Shape Change and Rho/Rho-Kinase-mediated Myosin Light Chain Phosphorylation in Mouse Platelets," The Journal of Cell Biology (1999), vol. 144, pp. 745-754.
Lednicer, Daniel et al., "4-Amino-4-arylcyclohexanones and Their Derivatives, a Novel Class of Analgesics. 1. Modification of the Aryl Ring," Journal of Medicinal Chemistry (1980), vol. 23, pp. 424-430.
Noma, Kensuke et al., "Physiological role of ROCKs in the cardiovascular system," American Journal of Physiology—Cell Physiology (2006), vol. 290, pp. C661-C668.
Lin, Tong et al., "Rho-ROCK-LIMK—Cofilin Pathway Regulates Shear Stress Activation of Sterol Regulatory Element Binding Proteins," Circulation Research (2003), vol. 92, pp. 1296-1304.
Furukawa, Noboru et al., "Role of Rho-kinase in regulation of insulin action and glucose homeostasis," Cell Metabolism (2005), vol. 2, pp. 119-129.
Masumoto, Akihiro et al., "Suppression of Coronary Artery Spasm by the Rho-Kinase Inhibitor Fasudil in Patients With Vasospastic Angina," Circulation (2002), vol. 105, pp. 1545-1547.
Nakahara, Tsutomu et al., "Y-27632 potentiates relaxant effects of $β_2$—adrenoceptor agonists in bovine tracheal smooth muscle," European Journal of Pharmacology (2000), vol. 389, pp. 103-106.
Caron, Stéphane et al., "The Synthesis of a Selective $PDE_4$/TNFα Inhibitor," Organic Process Research and Development (2001), vol. 5, pp. 587-592.
Pacaud, P. et al., "Rho proteins and vacular diseases," Archives des Maladies du Coeur et des Vaisseaux (2005), vol. 98, pp. 249-254.
Pommereau, Antje et al., "Two Simple and Generic Antibody-Independent Kinase Assays: Comparison of a Bioluminescent and a Microfluidic Assay Format," Journal of Biomolecular Screening (2004), vol. 9, pp. 409-416.

Remingtron's Pharmaceutical Science 17th Edition (1985), p. 1418.

Retzer, Michaela et al., "Lysophosphatidic acid-induced platelet shape change proceeds via Rho/Rho kinase-mediated myosin light-chain and moesin phosphorylation," Cellular Signalling (2000), vol. 12, pp. 645-664.

Okada, Hiroshi et al., "Synthesis and Antitumor Activities of Prodrugs of Benzoylphenylureas," Chemical and Pharmaceutical Bulletin (1994), vol. 42, pp. 57-61.

Negoro, Nobuyuki et al., "The Kinase Inhibitor Fasudil (HA-1077) Reduces Intimal Hyperplasia through Inhibiting Migration and Enhancing Cell Loss of Vascular Smooth Muscle Cells," Biochemical and Biophysical Research Communications (1999), vol. 262, pp. 211-215.

Uchida, Shigeki et al., "The Suppression of Small GTPase Rho Signal Transduction Pathway Inhibits Angiogenesis in Vitro and in Vivo," Biochemical and Biophysical Research Communications (2000), vol. 269, pp. 633-640.

Uehata, Masayoshi et al., "Calcium sensitization of smooth muscle mediated by a Rho-associated protein kinase in hypertension," Nature (1997), vol. 389, pp. 990-994.

Yoshii, Akihiro et al., "Relaxation of Contracted Rabbit Tracheal and Human Bronchial Smooth Muscle by Y-27632 through Inhibition of $Ca^{2+}$ Sensitization," American Journal of Respiratory Cell and Molecular Biology (1999), vol. 20, pp. 1190-1200.

Setoguchi, Hidekazu et al., "Leukotriene $C_4$ enhances the contraction of porcine tracheal smooth muscle through the activation of Y-27632, a rho kinase inhibitor, sensitive pathway," British Journal of Pharmacology (2001), vol. 132, pp. 111-118.

Steioff, Kerstin et al., "Long term Rho-kinase inhibition ameliorates endothelial dysfunction in LDL-Receptor deficient mice," European Journal of Pharmacology (2005), vol. 512, pp. 247-249.

Shimokawa, Hiroaki et al., "Anti-anginal Effect of Fasudil, a Rho-Kinase Inhibitor, in Patients With Stable Effort Angina: A Multicenter Study," Journal of Cardiovascular Pharmacology (2002), vol. 40, pp. 751-761.

Wakino, Shu et al., "Therapeutic strategies targeting the Rho/Rho kinase pathway are a promising choice for the treatment of renal disease," Drug News and Perspectives (2005), vol. 18, pp. 639-643.

Demiryürek, Seniz et al., "Effects of fasudil, a Rho-kinase inhibitor, on myocardial preconditioning in anesthetized rats," European Journal of Pharmacology (2005), vol. 527, pp. 129-140.

Yamakawa, Tadashi et al., "Involvement of Rho-Kinase in Angiotensin II-Induced Hypertrophy of Rat Vascular Smooth Muscle Cells," Hypertension (2000), vol. 35, pp. 313-318.

Sandu, Oana A. et al., "Diabetes in the Goto-Kakizaki Rat is Accompanied by Impaired Insulin-Mediated Myosin-Bound Phosphatase Activation and Vascular Smooth Muscle Cell Relaxation," Diabetes (2000), vol. 49, pp. 2178-2189.

Satoh, Shin-Ichi et al., "Pharmacological profile of hydroxy fasudil as a selectiverho kinase inhibitor on ischemic brain damage," Life Sciences (2001), vol. 69, pp. 1441-1453.

Yamamoto, Yasuhiro et al., "The Protein Kinase Inhibitor Fasudil Protects Against Ischemic Myocardial Injury Induced by Endothelin-1 in the Rabbit," Journal of Cardiovascular Pharmacology (2000), vol. 35, pp. 203-211.

Sato, Motohiko et al., "Involvement of Rho-Kinase-Mediated Phosphorylation of Myosin Light Chain in Enhancement of Cerebral Vasospasm," Circulation Research (2000), vol. 87, pp. 195-200.

Tatsumi, S. et al., "Involvement of Rho-Kinase in Inflammatory and Neuropathic Pain Through Phosphorylation of Myristoylated Alanine-Rich C-Kinase Substrate (Marcks)," Neuroscience (2005), vol. 131, pp. 491-498.

Somlyo, Avril V. et al., "Rho-Kinase Inhibitor Retards Migration and in Vivo Dissemination of Human Prostate Cancer Cells," Biochemical and Biophysical Research Communications (2000), vol. 269, pp. 652-659.

Seasholtz, Tammy M. et al., "Rho and Rho Kinase Mediate Thrombin-Stimulated Vascular Smooth Muscle Cell DNA Synthesis and Migration," Circulation Research (1999), vol. 84, pp. 1186-1193.

Totsukawa, Go et al., "Distinct Roles of Rock (Rho-kinase) and MLCK in Spatial Regulation of MLC Phosphorylation for Assembly of Stress Fibers and Focal Adhesions in 3T3 Fibroblasts," the Journal of Cell Biology (2000), vol. 150, pp. 797-806.

Vicente-Manzanares, Miguel et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis," the Journal of Immunology (2002), vol. 168, pp. 400-410.

Vicente-Manzanares, Miguel et al., "The RhoA Effector mDia Is Induced During T Cell Activation and Regulates Actin Polymerization and Cell Migration in T Lymphocytes," The Journal of Immunology (2003), vol. 171, pp. 1023-1034.

Zhou, Yan et al., "Nonsteroidal Anti-Inflammatory Drugs Can Lower Amyloidogenic $A\beta_{42}$ by Inhibiting Rho," Science (2003), vol. 302, pp. 1215-1217.

Curran, T.T. et al., "The Preparation of Optically Active 2-Cyclopenten-1,4-Diol Derivatives from Furfurl Alcohol" Tetrahedron, pp. 1983-2004, vol. 53(6), Feb. 10, 1997.

SUBSTITUTED ISOQUINOLINES AND ISOQUINOLINONES AS RHO KINASE INHIBITORS

CONTINUING DATA

This application is a 371 of PCT/EP2009/004421 filed Jun. 19, 2009 which claims the benefit of U.S. Provisional Application No. 61/153,149 filed on Feb. 17, 2009.

The present invention relates to substituted isoquinoline and isoquinolinones, their preparation and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-1948), bronchial smooth muscle contraction (Yoshii et al. Am. J. Resp. Cell Mol. Biol. 1999, 20, 1190-1200), asthma (Setoguchi et al. Br. J. Pharmacol. 2001, 132, 111-118; Nakahara et al. Eur. J. Pharmac. 2000, 389, 103-106) and chronic obstructive pulmonary disease (COPD, Maruoka et al. Nippon Rinsho, 1999, 57, 1982-1987), hypertension, pulmonary hypertension (Fukumoto et al. Heart 2005, 91, 391-392, Mukai et al. Nature 1997, 389, 990-994) and ocular hypertension and regulation of intraoccular pressure (Honjo et al. Invest. Ophthalmol. Visual Sci. 2001, 42, 137-144), endothelial dysfunction (Steioff et al. Eur. J. Pharmacol. 2005, 512, 247-249), angina (Masumoto et al. Circulation 2002, 105, 1545-47, Shimokawa et al. J. Cardiovasc. Pharmacol. 2002, 40, 751-761), nephropathy, including hypertension-induced, non-hypertension-induced, and diabetic nephropathies, renal failure and peripheral arterial occlusive disease (PAOD) (Wakino et al. Drug News Perspect. 2005, 18, 639-643), myocardial infarction (Demiryurek et al. Eur. J. Pharmacol. 2005, 527, 129-140, Hattori et al. Circulation 2004, 109, 2234-2239), cardiac hypertrophy and failure (Yamakawa et al. Hypertension 2000, 35, 313-318; Liao et al. Am. J. Physiol. Cell Physiol. 2006, 290, C661-668; Kishi et al. Circulation 2005, 111, 2741-2747), coronary heart disease, artherosclerosis, restenosis (Pacaud et al. Arch. Mal. Coeur 2005, 98, 249-254; Retzer et al. FEBS Lett. 2000, 466, 70-74; Negoro et al. Biochem. Biophys. Res. Commun. 1999, 262, 211-215), diabetes, diabetic complications, glucose utilization and metabolic syndrome (Sandu et al. Diabetes 2000, 49, 2178-2189; Maeda et al. Cell Metab. 2005, 2, 119-129), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara et al. J. Neurosurg. 2000, 93, 94-101), cerebral ischemia (Uehara et al. Nature 1997, 389, 990-994; Satoh et al. Life Sci. 2001, 69, 1441-1453; Hitomi et al. Life Sci. 2000, 67, 1929-1939; Yamamoto et al. J. Cardiovasc. Pharmacol. 2000, 35, 203-211), cerebral vasospasm (Sato et al. Circ. Res. 2000, 87, 195-200; Kim et al. Neurosurgery 2000, 46, 440-447), pain, e.g. neuropathic pain (Tatsumi et al. Neuroscience 2005, 131, 491-498; Inoue et al. Nature medicine 2004, 10, 712-718), infection of digestive tracts with bacteria (WO 98/06433), cancer development and progression, neoplasia where inhibition of Rho kinase has been shown to inhibit tumor cell growth and metastasis (Itoh et al. Nature Medicine 1999, 5, 221-225; Somlyo et al. Biochem. Biophys. Res. Commun. 2000, 269, 652-659), angiogenesis (Uchida et al. Biochem. Biophys. Res. Commun. 2000, 269, 633-640; Gingras et al. Biochem. J. 2000, 348, 273-280), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa et al. FEBS Lett. 2000, 466, 70-74; Bauer et al. Blood 1999, 94, 1665-1672; Klages et al. J. Cell Biol. 1999, 144, 745-754; Retzer et al. Cell Signal 2000, 12, 645-648) and leukocyte aggregation (Kawaguchi et al. Eur. J. Pharmacol. 2000, 403, 203-208; Sanchez-Madrid et al. J. Immunol. 2003, 171, 1023-1034; Sanchez-Madrid, et al. J. Immunol. 2002, 168, 400-410), stem cell and induced pluripotent stem cell related biology, e.g. cell-cell interaction, proliferation, cell cycle progression, gene regulation, migration, actin cytoskeleton modulation, and related application, e.g. as viability, survival, recovery, growth, susceptibility toward apoptosis, differentiation, development, gene modulation, modulation of morphogenesis, hosting and invasion (Krawetz et al. BioEssay 2009, 31, 336-343; Claassen et al. Mol. Reprod. Dev. 2009, PMID: 19235204; Heng Tissue Cell 2009, PMID: 19261317; Arnsdorf et al. J. Cell. Sci. 2009, 122, 546-553, Kim et al. Stem Cells 2009, 27, 191-199), modulation of epithelial-mesenchymal transition (Royal et al. Mol. Biol. Cell 2000, 11, 1709-1725; Zondag et al. J. Cell Biol. 2000, 149, 775-782; Masszi et al. Am. J. Physiol. Renal. Physiol. 2003, 284, 911-924; Smallhorn et al. Development 2004, 131, 2641-2651; Wells et al. Cell Motil. Cytoskeleton 2005, 62, 180-194; Wu et al. Cancer Res. 2006, 66, 9527-9534; Fan et al. Mol Biol Cell. 2007, 18, 1083-1097; Cho et al. Cell Biol. Int. 2007, 31, 1225-1230; Giehl et al. Cells Tissues Organs. 2007, 185, 123-130; Rodrigues-Díez et al. Pharm. Res. 2008, 25, 2447-2461), and bone resorption (Chellaiah et al. J. Biol. Chem. 2003, 278, 29086-29097). Na/H exchange transport system activation (Kawaguchi et al. Eur. J. Pharmacol. 2000, 403, 203-208), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res. 2003, 92, 1296-304).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, nonhypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

Moreover, such a compound is also useful for curative approaches associated with stem cell or induced pluripotent stem cell treatment, improvement of recognition or for treatment or prevention of depression, epilepsy, fibroid heart, renal papillary necrosis, tubulo-interstitial dysfunction, multiple sclerosis, vessel stenosis for example carotid stenosis or lipid disorders.

WO 2001/64238 describes isoquinoline-5-sulfonamide derivatives optionally substituted by a $-(CH_2)_{1-6}-O-(CH_2)_{0-6}-$, a $-(CH_2)_{0-6}-S-(CH_2)_{0-6}-$ or a $-(CH_2)_{0-6}-$ linked heterocyclic group useful as neuroprotective agents.

WO 2004/106325 (Schering A G) describes prodrugs of the Rho-kinase inhibitor fasudil carrying an ether or ester group in the 1-position of the isoquinoline ring.

WO 2001/039726 generically describes $-O-(C_0-C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer. The isoquinoline derivatives may be substituted by OH in the 1-position and are preferably 5-substituted by X—[(C$_1$-C$_6$)alkylene)]$_{0-1}$-Y wherein X may be oxygen and Y may be an aryl or a heterocyclic group.

Hagihara et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I—X—Ar II" wherein X may be (CHR$_1$)$_m$—Z—(CHR$_1$)$_n$, e.g. Z—CH$_2$, wherein Z may be O, R$_1$ is hydrogen or alkyl, Ar I may be among others an optionally substituted isoquinolone and Ar II may be among others an optionally substituted C$_{3-7}$ monocyclic saturated heterocyclic system.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group (CR$^e$R$^f$)$_p$OR$^{43}$ wherein p may be zero, and R$^{43}$ is e.g. a (C$_3$-C$_{10}$)cycloalkyl residue optionally substituted by NR$^{51}$R$^{52}$, wherein R$^{51}$ and R$^{52}$ may be hydrogen, (C$_1$-C$_6$) alkyl etc.; or R$^{43}$ is a group R$^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxy in the 1-position and are optionally substituted in 6-position by a group (CR$^e$R$^f$)$_p$OR$^{43}$ wherein p may be zero, and R$^{43}$ is e.g. a (C$_3$-C$_{10}$)cycloalkyl residue optionally substituted by NR$^{51}$R$^{52}$, wherein R$^{51}$ and R$^{52}$ may be hydrogen, (C$_1$-C$_6$)alkyl etc.; or R$^{43}$ is a group R$^{81}$ defined as a 4-6 membered unsaturated or saturated monocyclic heterocylic ring with 1, 2, 3 or 4 heteroatoms; and are substituted by a directly bound optionally substituted aryl or heteroaryl ring in the 4-position.

WO2003/053330 (Ube) generically describes isoquinolone derivatives of the formula

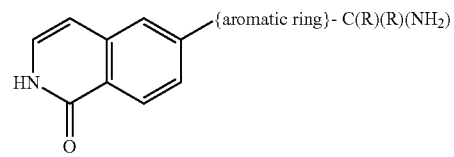

as Rho-kinase inhibitors.

WO 2007/012422 (Sanofi-Aventis) generically describes isoquinoline and isoquinolone derivatives of the formula

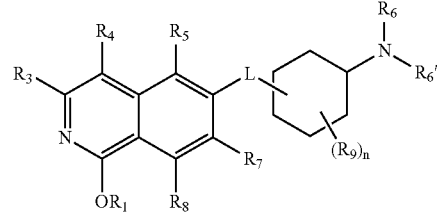

as Rho-Kinase inhibitors.

WO2008/077556 (Sanofi-Aventis) describes further 6-substituted isoquinoline and isoquinolone derivatives as Rho-Kinase inhibitors.

WO 2008/020081 (Organon) describes 6-substituted isoquinoline-1-one or isoquinoline 1-amine derivatives as Rho-kinase inhibitors.

Iwakubo et. al. (Bioorganic & Med. Chemistry Vol. 15, No. 1, 15. Nov. 2006, p. 350-364) describe a 5-substituted isoquinoline and indazol derived derivatives as Rho-kinase inhibitors.

In particular selectivity against other kinases has been identified as prerequisite for usage of kinase inhibitors as therapeutic agents. Fasudil for instance, a broadly profiled inhibitor of Rho kinase displays only modest selectivity against several other kinases, for example Protein Kinase A and Protein Kinase G (see for example Tamura et al., Biochimica et Biophysica Acta, Proteins and Proteomics (2005), 1754(1-2), 245-252. Also another inhibitor, Y-27632 only displays a 20-fold selectivity against Protein Kinase G.

Therefore, although several Rho-kinase inhibitors have been described there still remains the need for additional compounds useful in the treatment of Rho-kinase mediated diseases, in particular with improved selectivity.

An embodiment of the present invention is a compound of the formula (I)

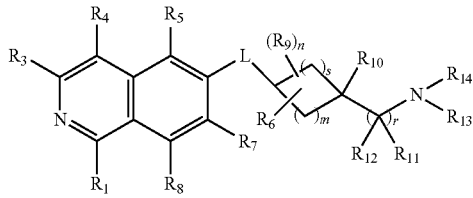

wherein
$R_1$ is H, OH or $NH_2$;
$R_3$ is H, halogen, CN, $(C_1-C_6)$alkyl, OH, $NH_2$, or NHR';
$R_4$ is H, halogen, hydroxy, CN, $(C_1-C_6)$alkyl, R', or $(C_1-C_6)$alkylene-R';
$R_5$ is H, halogen, CN, $(C_1-C_6)$alkyl, or R';
$R_7$ is H, halogen, CN, $(C_1-C_6)$alkyl, O—$(C_1-C_6)$alkyl, R', or $SO_2$—$NH_2$;
$R_8$ is H, halogen or $(C_1-C_6)$alkyl;
$R_9$ is
R',
OH,
halogen,
$(C_1-C_6)$alkyl,
O—$(C_1-C_6)$alkyl,
$(C_1-C_6)$alkylene-R',
$(C_2-C_6)$alkenyl,
$(C_2-C_6)$alkynyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$,
$(C_1-C_6)$alkylene-C(O)N[R']$_2$;
$(C_1-C_6)$alkylene-C(O)O—$(C_1-C_6)$alkyl,
COOH,
C(O)O—$(C_1-C_6)$alkyl,
C(O)OR'
C(O)$(C_1-C_6)$alkyl,
C(O)R',
C(O)$NH_2$,
C(O)—NH—$(C_2-C_6)$alkenyl,
C(O)—NH—$(C_2-C_6)$alkynyl,
C(O)NH—$(C_1-C_6)$alkyl,
C(O)NHR',
C(O)—NH$(C_1-C_6)$alkylene-R',
C(O)N[$(C_1-C_6)$alkyl]R'
C(O)N[$(C_1-C_6)$alkyl]$_2$,
C(O)—$(C_1-C_6)$alkylene-R', or
C(O)O$(C_1-C_6)$alkylene-R';
$R_6$ is absent;
or is one $(C_1-C_4)$alkylene bound to the cycloalkyl ring, in which the $(C_1-C_4)$alkylene forms a second bond to a different carbon atom of the cycloalkyl ring to form a bicyclic ring system,
wherein in the bicyclic ring system optionally one or two carbon atomes are replaced by a group independently selected from O, N—$R_{15}$, S, SO or $SO_2$;
or, if m and s are 2, m is 3 and s is 1, or m is 4 and s is 0,
$R_6$ is $CH_2$—CH—$(CH_2)_2$ which is bound with one $CH_2$ to the cycloalkyl ring and the two other $CH_2$ are bound to different carbon atoms of the cycloalkyl ring;
and, if m is 3 and s is 3,
$R_6$ are two methylene groups bound to different carbon atoms of the cycloalkyl ring, wherein the methylene groups or the $CH_2$—CH—$(CH_2)_2$ group are bound to carbon atoms of the cycloaalkyl ring such that they form an adamantane system of the formula

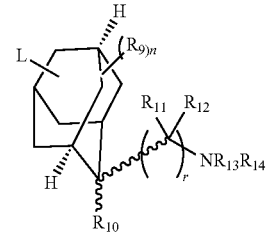

wherein L can be bound to any secondary or tertiary carbon atom and
wherein the bicyclic ring system or adamantane system is unsubstituted or optionally substituted by $R_9$.
$R_{10}$ is
H,
$(C_6-C_{10})$aryl,
O—$(C_6-C_{10})$aryl,
O—$(C_1-C_6)$alkylene-$(C_6-C_{10})$aryl, or
$(C_6-C_{10})$heteroaryl, wherein $(C_6-C_{10})$aryl or $(C_6-C_{10})$heteroaryl are unsubstituted or substituted.
$R_{11}$ is
H,
$(C_1-C_6)$alkyl,
$(C_1-C_6)$alkylene-R',
$(C_3-C_8)$cycloalkyl,
$(C_5-C_{10})$heteroaryl,
$(C_3-C_8)$heterocycloalkyl,
$(C_6-C_{10})$aryl;
or $R_{11}$ and $R_{12}$ together with carbon atom to which they are attached form a $(C_3-C_8)$cycloalkyl or a $(C_3-C_8)$-heterocycloalkyl ring;
$R_{12}$ is
$(C_1-C_6)$alkyl,
$(C_3-C_5)$cycloalkyl,
$(C_5-C_{10})$heteroaryl,
$(C_3-C_8)$heterocycloalkyl, or
$(C_6-C_{10})$aryl;
or $R_{12}$ is H, provided that r=2 and the other $R_{12}$ is not H;
or $R_{11}$ and $R_{12}$ together with carbon atom to which they are attached form a $(C_3-C_8)$cycloalkyl or a $(C_3-C_8)$-heterocycloalkyl ring;
$R_{13}$ and $R_{14}$ are independently of each other
H,
R',
$(C_1-C_6)$alkyl,
$(C_1-C_6)$alkylene-R',
$(C_1-C_6)$alkylene-O—$(C_1-C_6)$alkyl,
$(C_1-C_6)$alkylene-O—R',
$(C_1-C_6)$alkylene-CH[R']$_2$,
$(C_1-C_6)$alkylene-C(O)—R',
$(C_1-C_6)$alkylene-C(O)$NH_2$,
$(C_1-C_6)$alkylene-C(O)NH—R',
$(C_1-C_6)$alkylene-C(O)NH—$(C_1-C_6)$alkyl,
$(C_1-C_6)$alkylene-C(O)N[$(C_1-C_6)$alkyl]$_2$, ($C_1$-$C_6$)alkylene-C(O)N[R']$_2$,
($C_1$-$C_6$)alkylene-C(O)O—($C_1$-$C_6$)alkyl,
C(O)O—($C_1$-$C_6$)alkyl,
C(O)OR',
C(O)($C_1$-$C_6$)alkyl,
C(O)R',
C(O)NH—($C_1$-$C_6$)alkyl,
C(O)NHR',
—C(O)N[($C_1$-$C_6$)alkyl],
C(O)N[($C_1$-$C_6$)alkyl]$_2$,
C(O)—($C_1$-$C_6$)alkylene-R',
C(O)O($C_1$-$C_6$)alkylene-R', or
$R_{13}$ and $R_{14}$, together with the N-atom to which they are attached, form a ($C_3$-$C_8$) heterocycloalkyl;
$R_{15}$ is H or ($C_1$-$C_6$)alkyl;
n is 0, 1, 2, 3 or 4;
m is 1, 2, 3 or 4;
s is 0, 1, 2, or 3;
r is 1 or 2;
L is O(CH$_2$)$_p$, S(CH$_2$)$_p$, S(O)(CH$_2$)$_p$, SO$_2$(CH$_2$)$_p$, NH(CH$_2$)$_p$, N($C_1$-$C_6$)alkyl-(CH$_2$)$_p$, N($C_3$-$C_6$)cycloalkyl-(CH$_2$)$_p$; or N[($C_1$-$C_3$)alkylene-R']—(CH$_2$)$_p$;
p is 0, 1, 2, 3 or 4;
R' is
($C_3$-$C_8$)cycloalkyl,
($C_5$-$C_{10}$)heteroaryl,
($C_3$-$C_8$)heterocycloalkyl,
($C_6$-$C_{10}$)aryl;
wherein in residues $R_3$ to $R_{15}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{15}$ cycloalkyl or heterocycloalkyl is unsubstituted or optionally substituted one or more times by ($C_1$-$C_6$)alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{15}$ alkyl or alkylene is unsubstituted or optionally substituted one or more times by halogen;
wherein in residues $R_3$ to $R_{15}$ ($C_6$-$C_{10}$)aryl and ($C_5$-$C_{10}$)heteroaryl are unsubstituted or optionally substituted one or more times by a group independently selected from halogen, OH, NO$_2$, N$_3$, CN, C(O)—($C_1$-$C_6$)alkyl, C(O)—($C_6$-$C_{10}$)aryl, COOH, COO($C_1$-$C_6$)alkyl, CONH$_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, PO$_3$H$_2$, SO$_3$H, SO$_2$—NH$_2$, SO$_2$NH($C_1$-$C_6$)alkyl, SO$_2$N[($C_1$-$C_6$)alkyl]$_2$, S—($C_1$-$C_6$)alkyl; SO—($C_1$-$C_6$)alkyl, SO$_2$—($C_1$-$C_6$)alkyl, SO$_2$—N=CH—N[($C_1$-$C_6$)alkyl]$_2$, SF$_5$, C(NH)(NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—SO$_2$—($C_1$-$C_6$)alkyl, NH—SO$_2$—($C_6$-$C_{10}$)aryl, NH—SO$_2$—($C_5$-$C_{10}$heteroaryl, NH—SO$_2$—($C_3$-$C_8$)heterocycloalkyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—NH—($C_1$-$C_6$)alkyl], ($C_6$-$C_{10}$)aryl, ($C_1$-$C_6$)alkylene-($C_6$-$C_{10}$)aryl, O—($C_6$-$C_{10}$)aryl, O—($C_1$-$C_6$)alkylene-($C_6$-$C_{10}$)aryl, ($C_5$-$C_{10}$)heteroaryl, ($C_3$-$C_8$)heterocycloalkyl, ($C_1$-$C_6$)alkylene-($C_5$-$C_{10}$)heteroaryl, ($C_1$-$C_6$)alkylene-($C_3$-$C_8$)heterocycloalkyl, O—($C_1$-$C_6$)alkylene-($C_5$-$C_{10}$)heteroaryl, O—($C_1$-$C_6$)alkylene-($C_3$-$C_8$)heterocycloalkyl, wherein said ($C_6$-$C_{10}$)aryl, ($C_5$-$C_{10}$)heteroaryl, ($C_3$-$C_8$)heterocycloalkyl or ($C_3$-$C_8$)cycloalkyl may be substituted one to three times by a group independently selected from halogen, OH, NO$_2$, CN, O—($C_1$-$C_6$)alkyl, ($C_1$-$C_6$)alkyl, NH$_2$, NH($C_1$-$C_6$)alkyl, N[($C_1$-$C_6$)alkyl]$_2$, SO$_2$CH$_3$, COOH, C(O)O—($C_1$-$C_6$)alkyl, CONH$_2$, ($C_1$-$C_6$)alkylene-O—($C_1$-$C_6$)alkyl, ($C_1$-$C_6$)alkylene-O—($C_6$-$C_{10}$)aryl, or O—($C_1$-$C_6$)alkylene-($C_6$-$C_{10}$)aryl; or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to; and wherein aryl substituents of ($C_6$-$C_{10}$)aryl, ($C_5$-$C_{10}$)heteroaryl, ($C_3$-$C_8$)heterocycloalkyl or ($C_3$-$C_8$)cycloalkyl groups may not be further substituted by an aryl, heteroaryl, heterocycloalkyl, or ($C_3$-$C_8$)cycloalkyl containing group;
their stereoisomeric and/or tautomeric forms and/or their pharmaceutically acceptable salts thereof.

In another embodiment the present invention also relates to a compound of formula (I) and/or its pharmaceutically acceptable salt for use as a medicament. It also relates to the use of at least one compound of formula (I) and/or a pharmaceutically acceptable salt thereof for the treatment and/or prevention of Rho-Kinase mediated diseases such as hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy, infection of digestive tracts with bacteria, sepsis or cancer development and progression. The invention further relates to a medicament comprising an effective amount of at least one compound of formula (I) and/or a pharmacologically acceptable salt thereof. Another object of the present invention is a method of producing a compound of formula (I).

The term alkyl as used in ($C_1$-$C_2$)alkyl, ($C_1$-$C_4$)alkyl, or ($C_1$-$C_6$)alkyl and the corresponding alkylene substituents is understood as a hydrocarbon residue which can be linear, i.e. straight-chain, or branched and has 1, 2, 3, 4, 5, or 6 carbon atoms, respectively. This also applies if an alkyl group occurs as a substituent on another group, for example in an alkoxy group (O-alkyl), S-alkyl or a —O($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl or alkylene groups may optionally be halogenated once or more, e.g. alkyl groups may be fluorinated, e.g. perfluorinated. Examples of halogenated alkyl groups are CH$_2$F, CHF$_2$, CF$_3$ and CH$_2$CF$_3$, OCF$_3$, SCF$_3$, or —O—(CF$_2$)$_2$—O—.

The term ($C_2$-$C_6$)-alkenyl means a hydrocarbon residue whose carbon chain is straight-chain or branched and comprises 2 to 6 carbon atoms and has, depending on the chain length, 1, 2 or 3 double bonds, for example, vinyl, 1-propenyl, 2-propenyl(=allyl), 2-butenyl, 3-butenyl, 2-methyl-2-butenyl, 3-methyl-2-butenyl, 5-hexenyl or 1,3-pentadienyl. The double bond may where possible have the E or Z orientation.

The double bonds may be both internal and terminal.

$(C_2-C_6)$-alkynyl groups are hydrocarbon residue whose carbon chain is straight-chain or branched and comprises 2 to 6 carbon atoms and have, depending on the chain length, 1 or 2 triple bonds, for example, ethynyl, 1-propynyl, 2-propynyl (=propargyl) or 2-butynyl. The triple bonds may be both internal and terminal.

Halogen means fluoro (F), chloro (Cl), bromo (Br) or iodo (I).

The term $(C_1-C_8)$heteroalkyl or the corresponding $(C_1-C_8)$ heteroalkylene substituents are understood as $(C_1-C_8)$alkyl or $(C_1-C_8)$alkylene groups wherein at least one carbon atom, preferably one or two carbon atoms, more preferred one carbon atom, is replaced by a group selected from O, NH, or S and wherein the nitrogen and sulfur atoms may optionally be oxidized. The heteroatom may be placed at any position of the alkyl or alkylene group. Examples of $(C_1-C_8)$heteroalkyl groups include —$CH_2$—O—$CH_3$, —$CH_2$—$CH_2$—O—$CH_2$—$CH_3$, —$CH_2$—NH—$CH_2$—$CH_3$, —$CH_2$—N($CH_2$—$CH_3)_2$—$CH_2$—$CH_2$—$CH_2$—O—$CH_3$, —$CH_2$—$CH_2$—$CH_2$—S—$CH_3$, —$CH_2$—O—CH($CH_3)_2$, —$CH_2$—O—$CH_2$—$CH_2$—O—$CH_3$ or O—$CH_2$—$CH_3$.

$(C_3-C_8)$cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bonds (unsaturated cycloalkyl groups) like, for example, cyclopentenyl or cyclohexenyl, which can be bonded via any carbon atom.

A $(C_6-C_{10})$aryl group means an aromatic ring or a ring system which comprises two aromatic rings which are fused or otherwise linked or which comprises two fused aromatic rings wherein one ring is saturated or partly saturated, i.e contains at least one C—C single bond, for example a phenyl, naphthyl, biphenyl, tetrahydronaphthyl, alpha- or beta-tetralon-, indanyl- or indan-1-on-yl group. A preferred $(C_6-C_{10})$aryl group is phenyl.

$(C_3-C_8)$heterocycloalkyl group means a saturated (contains no double bonds) monocyclic carbon ring system containing 3, 4, 5, 6, 7 or 8 ring atoms in which one or more carbon atoms can be replaced by one or more heteroatoms such as, for example 1, 2 or 3 nitrogen atoms, 1 or 2 oxygen atoms, 1 or 2 sulfur atoms or combinations of different hetero atoms. The heterocycloalkyl residues can be bound at any positions, for example on the 1-position, 2-position, 3-position, 4-position, 5-position, 6-position, 7-position or 8-position. Also included are the corresponding N-oxides, sulfoxides or sulfones of these compounds.

Examples of $(C_3-C_8)$heterocycloalkyl groups are oxiranyl, oxetanyl, aziridinyl, tetrahydrofuranyl, tetrahydropyranyl, dioxolanyl, for example 1,3-dioxolanyl, dioxanyl, for example 1,4-dioxanyl, piperidinyl, pyrrolidinyl, imidazolidinyl, triazolidinyl, hexahydropyrimidinyl, piperazinyl, triazinanyl, for example, 1,3,5-triazinanyl, 1,2,3-triazinanyl or 1,2,4-triazinanyl, tetrahydrothiophenyl, tetrahydro-thiopyranyl, dithiolanyl, for example 1,3-dithiolanyl, dithianyl, thiazolidinyl, oxazolidinyl, oxathiolanyl, for example 1,3-oxathiolanyl, morpholinyl or thiomorpholinyl, diazepanyl, for example 1,4-diazepanyl.

A preferred $(C_3-C_8)$heterocycloalkyl group is morpholinyl, pyrrolidinyl, piperazinyl, piperidinyl, oxetanyl or tetrahydropyranyl.

$(C_5-C_{10})$heteroaryl means a mono- or bicyclic ring system in which one or more carbon atoms can be replaced by one or more heteroatoms such as, for example 1, 2, 3 or 4 nitrogen atoms, 1 or 2 oxygen atoms, 1 or 2 sulfur atoms or combinations of different hetero atoms. The heteroaryl residues can be bound at any position, for example on the 1-position, 2-position, 3-position, 4-position, 5-position, 6-position, 7-position or 8-position. $(C_5-C_{10})$heteroaryl groups may be an (1) aromatic monocyclic or bicyclic ring system or (2) a bicyclic ring system wherein one ring is aromatic and the second ring is at least partially saturated.

Also included are the corresponding N-oxides, sulfoxides or sulfones of these compounds.

Suitable $(C_5-C_{10})$heteroaryl groups are benzimidazolyl, benzofuryl, benzothienyl, azaindolyl, benzothiophenyl, benzoxazolyl, benzthiazolyl, benztriazolyl, benzisoxazolyl, benzisothiazolyl, carbolinyl, cinnolinyl, chromanyl, chromenyl, naphthyridinyl, phthalazinyl, pyridoimidazolyl, pteridinyl, purynyl, quinazolinyl, quinoxalinyl, quinolinyl, isoquinolinyl, tetrahydroisoquinolinyl, tetrahydroquinolinyl, indolinyl, indolizinyl, indolyl, furyl, furazanyl, thienyl, imidazolyl, imidazolinyl, 1H-indazolyl, pyrazolyl, oxazolyl, 1,2,3-oxadiazolyl, 1,2,4-oxadiazolyl, 1,2,5-oxadiazolyl, 1,3,4-oxadiazolyl, isoxazolyl, thiazolyl, isothiazolyl, pyridyl, triazolyl, pyrazinyl, pyrimidinyl, pyridazinyl, pyrazolinyl, pyrrolyl, 1,2,3-thiadiazolyl, 1,2,4-thiadiazolyl, 1,2,5-thiadiazolyl, 1,3,4-thiadiazolyl, tetrazolyl.

Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in $(C_5-C_{10})$heteroaryl residues can occur on free carbon atoms or on nitrogen atoms.

Preferred examples of $(C_5-C_{10})$heteroaryl residues are benzofuryl, quinolinyl, furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, pyridazinyl and tetrazolyl.

A preferred $(C_5-C_{10})$heteroaryl is a $(C_5-C_6)$heteroaryl group. Preferred $(C_5-C_6)$heteroaryl residues are furyl, thienyl, imidazolyl, pyrazolyl, oxazolyl, isoxazolyl, thiazolyl, isothiazolyl, pyridyl, triazolyl, oxadiazolyl, pyrazinyl, pyrimidinyl, and pyridazinyl. Preferred examples of $(C_5-C_6)$heteroaryl residues are 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2- or -5-yl, 2-, 4- or 5-thiazolyl, 3-, 4- or 5-isothiazolyl, 2-, 3- or 4-pyridyl, 2-, 4-, 5- or 6-pyrimidinyl, 3- or 4-pyridazinyl, or pyrazinyl.

In residues $R_3$ to $R_{15}$ $(C_6-C_{10})$aryl and $(C_5-C_{10})$heteroaryl residues are unsubstituted or, if not specified otherwise, optionally substituted one or more times, preferably one to three times, more preferably once, by a group independently selected from halogen, OH, $NO_2$, $N_3$, CN, C(O)—$(C_1-C_6)$alkyl, C(O)—$(C_6-C_{10})$aryl, COOH, COO$(C_1-C_6)$alkyl, $CONH_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, $PO_3H_2$, $SO_3H$, $SO_2$—$NH_2$, $SO_2NH(C_1-C_6)$alkyl, $SO_2N[(C_1-C_6)$alkyl]$_2$, S—$(C_1-C_6)$alkyl, SO—$(C_1-C_6)$alkyl, $SO_2$—$(C_1-C_6)$alkyl, $SO_2$—N=CH—N[$(C_1-C_6)$alkyl]$_2$, $SF_5$, C(NH)($NH_2$), $NH_2$, NH—$(C_1-C_6)$alkyl, N[$(C_1-C_6)$alkyl]$_2$, NH—C(O)—$(C_1-C_6)$alkyl, NH—C(O)O—$(C_1-C_6)$alkyl, NH—$SO_2$—$(C_1-C_6)$alkyl, NH—$SO_2$—$(C_6-C_{10})$aryl, NH—$SO_2$—$(C_5-C_{10})$heteroaryl, NH—$SO_2$—$(C_3-C_8)$heterocycloalkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heteroaryl, $(C_3-C_8)$heterocycloalkyl, $(C_1-C_6)$alkylene-$(C_5-C_{10})$heteroaryl, $(C_1-C_6)$alkylene-$(C_3-C_8)$heterocycloalkyl, O—$(C_1-C_6)$alkylene-$(C_5-C_{10})$heteroaryl, O—$(C_1-C_6)$alkylene-$(C_3-C_8)$heterocycloalkyl, wherein said $(C_6-C_{10})$aryl, $(C_5-C_{10})$heteroaryl, $(C_3-C_8)$heterocycloalkyl or $(C_3-C_8)$cycloalkyl may be substituted one to three times by a group independently selected from halogen, OH, NO$_2$, CN, O—$(C_1-C_6)$alkyl, $(C_1-C_6)$alkyl, NH$_2$, NH$(C_1-C_6)$alkyl, N[$(C_1-C_6)$alkyl]$_2$, SO$_2$CH$_3$, COOH, C(O)O—$(C_1-C_6)$alkyl, CONH$_2$, $(C_1-C_6)$alkylene-O—$(C_1-C_6)$alkyl, $(C_1-C_6)$alkylene-O—$(C_6-C_{10})$aryl, or O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to; and wherein aryl substituents of $(C_6-C_{10})$aryl, $(C_5-C_{10})$heteroaryl, $(C_3-C_8)$heterocycloalkyl or $(C_3-C_8)$cycloalkyl groups may not be further substituted by an aryl, heteroaryl, heterocycloalkyl, or $(C_3-C_8)$cycloalkyl containing group.

Preferred substituents for $(C_6-C_{10})$aryl and $(C_5-C_{10})$heteroaryl groups are OH, $(C_1-C_4)$alkyl, O—$(C_1-C_4)$alkyl, O-phenyl, phenyl, C(O)O—$(C_1-C_6)$alkyl, C(O)OH, C(O)—$(C_1-C_4)$alkyl, halogen, NO$_2$, SO$_2$NH$_2$, CN, SO$_2$—$(C_1-C_4)$alkyl, SO$_2$—N=CH—N[$(C_1-C_6)$alkyl]$_2$, NH—SO$_2$—$(C_1-C_4)$alkyl, NH$_2$, NH—C(O)—$(C_1-C_4)$alkyl, $(C_3-C_8)$cycloalkyl, $(C_1-C_4)$alkyl-OH, C(O)N[$(C_1-C_4)$alkyl]$_2$, C(O)NH$(C_1-C_6)$alkyl, C(O)NH$_2$, N[$(C_1-C_4)$alkyl]$_2$, $(C_1-C_4)$alkylene-N[$(C_1-C_4)$alkyl]$_2$, $(C_1-C_4)$alkylene-O—$(C_1-C_4)$alkyl, $(C_5-C_6)$heteroaryl, $(C_3-C_8)$heterocycloalkyl, $(C_1-C_4)$alkylene-$(C_6-C_{10})$aryl, wherein the $(C_6-C_{10})$aryl may be further substituted one to three times, preferably once, by halogen, $(C_1-C_4)$alkyl, O—$(C_1-C_4)$alkyl, $(C_1-C_4)$alkylene-O—$(C_1-C_6)$alkyl, $(C_6-C_{10})$aryl, O—$(C_1-C_6)$alkylene-$(C_6-C_{10})$aryl, or may be vicinally substituted by a O—$(C_1-C_4)$alkylene-O group whereby a 5-8-membered ring is formed together with the carbon atoms the oxygen atoms are attached to.

More preferred substituents for $(C_6-C_{10})$aryl and $(C_5-C_{10})$heteroaryl are OH, halogen, CN, phenyl, O-phenyl, NH—C(O)—$(C_1-C_4)$alkyl, C(O)—$(C_1-C_4)$alkyl, C(O)—O$(C_1-C_4)$alkyl, $(C_1-C_4)$alkyl, O—$(C_1-C_4)$alkyl, CONH$_2$, SO$_2$—NH$_2$, SO$_2$—$(C_1-C_4)$alkyl or SO$_2$—N=CH—N[$(C_1-C_4)$alkyl]$_2$, $(C_1-C_4)$alkylene-phenyl, $(C_1-C_4)$alkylene-O—$(C_1-C_4)$alkyl or $(C_5-C_6)$heteroaryl, wherein the phenyl is unsubstituted or optionally substituted one to three times, preferably once, by OH, halogen, $(C_1-C_4)$alkyl or O—$(C_1-C_4)$alkyl. Even more preferred substituents for $(C_6-C_{10})$aryl and $(C_5-C_{10})$heteroaryl are OH, halogen, CN, phenyl, O-phenyl, NH—C(O)—$(C_1-C_4)$alkyl especially NH—C(O)—CH$_3$, C(O)—$(C_1-C_4)$alkyl especially C(O)—CH$_3$, C(O)—O$(C_1-C_4)$alkyl especially C(O)—OCH$_3$, $(C_1-C_4)$alkyl especially CH$_3$ or CF$_3$, O—$(C_1-C_4)$alkyl especially O—CH$_3$, CONH$_2$, SO$_2$—NH$_2$, SO$_2$—$(C_1-C_4)$alkyl especially SO$_2$—CH$_3$ or SO$_2$—CF$_3$; or SO$_2$—N=CH—N[$(C_1-C_4)$alkyl]$_2$ especially SO$_2$—N=CH—N[(CH$_3$)$_2$], wherein the phenyl is unsubstituted or optionally substituted one to three times, preferably once, by OH, halogen, $(C_1-C_4)$alkyl or O—$(C_1-C_4)$alkyl.

More especially preferred substituents for $(C_6-C_{10})$aryl and $(C_5-C_{10})$heteroaryl groups are OH, CN, $(C_1-C_4)$alkyl especially CH$_3$ or CF$_3$, O$(C_1-C_4)$alkyl especially O—CH$_3$, halogen or phenyl, wherein the phenyl may be further substituted one to three times, preferably once, by OH, halogen, $(C_1-C_4)$alkyl especially CH$_3$ or CF$_3$, or O—$(C_1-C_4)$alkyl especially O—CH$_3$.

Most preferred substituents for $(C_6-C_{10})$aryl and $(C_5-C_{10})$heteroaryl groups are OH, CN, halogen, $(C_1-C_4)$alkyl especially CH$_3$ or CF$_3$, O$(C_1-C_4)$alkyl especially O—CH$_3$, or halogen.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

In residues $R_3$ to $R_{15}$ an alkyl or alkylene is unsubstituted or, if not specified otherwise, optionally substituted one or more times by halogen. If substituted, alkyl or alkylene is preferably substituted one to three times by halogen selected from chloro or bromo but may be substituted by fluoro once or more, e.g. being perfluorinated. Preferably halogen is fluoro. Preferably alkylene is not halogenated. More preferred an alkyl or alkylene is not halogenated.

In residues $R_3$ to $R_{15}$ alkyl or alkylene is unsubstituted or, if not specified otherwise, optionally substituted one or more times by a group selected independently from OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$. If substituted, the number of substituents is preferably between 1, 2, 3 or 4, more preferably 1 or 2 with 1 being even more preferred. Preferably an alkylene is not substituted by one of these groups. More preferably an alkyl or alkylene is not substituted by one of these groups. Preferably alkyl or alkylene in $R_3$, $R_4$, $R_5$, $R_7$ and $R_8$ are not substituted. In a further embodiment alkyl or alkylene in $R_4$ to $R_{15}$ is not substituted by one of these groups.

In residues $R_3$ to $R_{15}$ cycloalkyl or heterocycloalkyl is unsubstituted or, if not specified otherwise, optionally substituted one or more times by $(C_1-C_6)$alkyl, halogen, OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$. If substituted, the number of substituents is preferably between 1, 2, 3 or 4, more preferably 1 or 2 with 1 being even more preferred. Preferably cycloalkyl or heterocycloalkyl in $R_3$ to $R_9$ are not substituted. In a further embodiment cycloalkyl or heterocycloalkyl in $R_3$ to $R_{15}$ are not substituted. In a preferred embodiment a heterocycloalkyl is not substituted. In another embodiment cycloalkyl is not substituted.

The general and preferred substituents of $(C_6-C_{10})$aryl, $(C_5-C_{10})$heteroaryl, $(C_3-C_8)$heterocycloalkyl and $(C_3-C_8)$cycloalkyl groups as defined before may be combined with the general and preferred definitions of $R_1$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, n, s, m, r, p and L as described in the following embodiments of a compound of formula (I).

The following embodiments of a compound of formula (I) do further characterize and are part of the present invention.

In one embodiment of a compound of formula (I) $R_1$ is H and the compound is characterized by the formula (II)

(II)

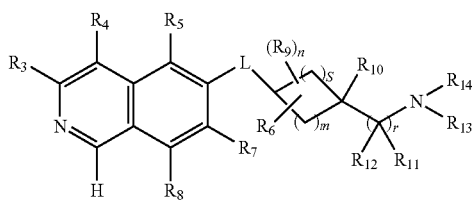

In another embodiment of the present invention $R_1$ is OH and the compound is characterized by the formula (IIIa)

(IIIa)

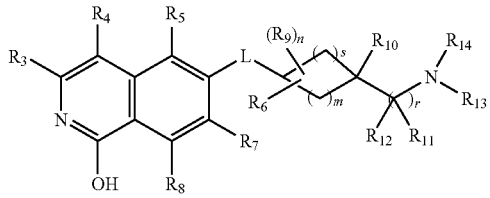

The isoquinoline derivative of formula (I), wherein $R_1$ is OH, includes the corresponding tautomeric 1-isoquinolone derivative which is characterized by the formula (IIIb)

(IIIb)

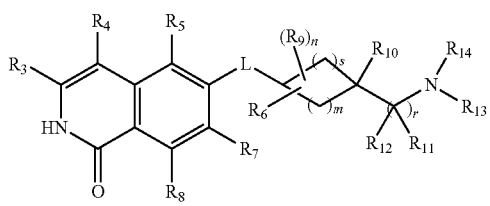

This tautomeric form is also an embodiment of the present invention.

In a further embodiment $R_1$ is $NH_2$ and the compound is characterized by the formula (IV)

(IV)

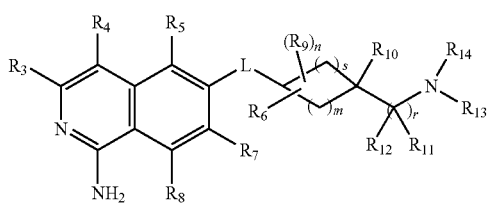

The following further embodiments equally refer to the compounds of formula (I), (II), (IIIa), (IIIb) and (IV).

In a preferred embodiment $R_1$ is H or OH; more preferably $R_1$ is OH.

In one embodiment $R_3$ is preferably H, halogen, $(C_1\text{-}C_6)$alkyl, or NHR'. In another more preferred embodiment $R_3$ is H, halogen, unsubstituted or substituted NH—$(C_5\text{-}C_6)$heteroaryl, unsubstituted or substituted NH—$(C_3\text{-}C_8)$heterocycloalkyl or unsubstituted or substituted NH-phenyl. In a even more preferred embodiment $R_3$ is unsubstituted or substituted NH—$(C_5\text{-}C_6)$heteroaryl containing one or more N atoms, or unsubstituted or substituted NH-phenyl. In a most preferred embodiment $R_3$ is H. Examples of NHR' substituents in $R_3$ are

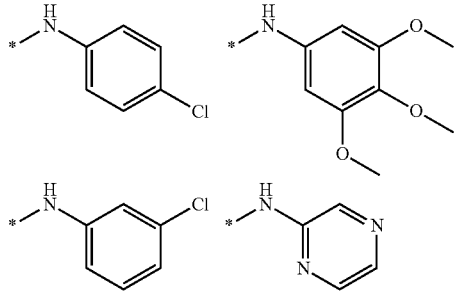

The asterisk (*) denotes where the bond is connected to the C-atom of the ring.

In a preferred embodiment $R_4$ is H, halogen, $(C_1\text{-}C_6)$alkyl, or $(C_1\text{-}C_2)$-alkylene-phenyl. In a more preferred embodiment $R_4$ is H, halogen or unsubstituted or substituted $(C_1\text{-}C_4)$alkyl or $(C_1\text{-}C_2)$-alkylene-phenyl, preferably unsubstituted $(C_1\text{-}C_4)$alkyl or $(C_1\text{-}C_2)$-alkylene-phenyl. Even more preferred $R_4$ is H or halogen, with H being most preferred.

In a preferred embodiment $R_5$ is H, CN, halogen, unsubstituted or substituted $(C_1\text{-}C_6)$alkyl, unsubstituted or substituted $(C_6\text{-}C_{10})$aryl, substituted or unsubstituted $(C_3\text{-}C_8)$cycloalkyl or unsubstituted or substituted $(C_5\text{-}C_{10})$heteroaryl. $(C_6\text{-}C_{10})$aryl is preferably phenyl. Examples of $R_5$ are hydrogen, fluoro, chloro, bromo, iodo, methyl, ethyl, phenyl, thienyl or pyridyl, nitrile, (p-methoxy)-phenyl, N-aniline, cyclopropyl, tetrazol, 4-methoxy-aniline. In a more preferred embodiment $(C_1\text{-}C_6)$alkyl, $(C_6\text{-}C_{10})$aryl, $(C_3\text{-}C_8)$cycloalkyl or $(C_5\text{-}C_{10})$heteroaryl are unsubstituted. In an even more preferred embodiment $R_5$ is H, halogen, methyl, ethyl, phenyl, thienyl, or pyridyl, more specifically H, halogen, methyl, or ethyl. Most preferred $R_5$ is H.

In a preferred embodiment $R_7$ is H, halogen, nitrile, unsubstituted or substituted $(C_1\text{-}C_6)$alkyl, unsubstituted or substituted O—$(C_1\text{-}C_6)$alkyl, or unsubstituted or substituted R'. In a more preferred embodiment $R_7$ is H, halogen, nitrile, unsubstituted or substituted $(C_1\text{-}C_4)$alkyl, unsubstituted or substituted O—$(C_1\text{-}C_4)$alkyl, unsubstituted or substituted phenyl, unsubstituted or substituted $(C_5\text{-}C_6)$heteroaryl, or unsubstituted or substituted $(C_3\text{-}C_6)$cycloalkyl. Preferably, alkyl, phenyl or $(C_5\text{-}C_6)$heteroaryl are unsubstituted.

In an even more preferred embodiment $R_7$ is H, fluoro, chloro, bromo, methyl, ethyl, methoxy, phenyl, nitrile, cyclopropyl, or thienyl. More preferably $R_7$ is H, fluoro, chloro, bromo, methyl or methoxy, in particular H, methyl or chloro. Most preferred $R_7$ is chloro.

In a preferred embodiment $R_8$ is H, Cl, F, methyl or ethyl. In a more preferred embodiment $R_8$ is H.

In a preferred embodiment $R_9$ is R', OH, halogen, $(C_1\text{-}C_6)$alkyl, $(C_1\text{-}C_6)$alkylene-R', $(C_2\text{-}C_6)$alkenyl, $(C_1\text{-}C_6)$alkylene-C(O)NH—R', $(C_1\text{-}C_6)$alkylene-C(O)NH—$(C_1\text{-}C_6)$alkyl, COOH, $CONH_2$, C(O)NH—$(C_1\text{-}C_6)$alkyl, C(O)NHR', C(O)—NH—$(C_1\text{-}C_6)$alkynyl, C(O)—NH$(C_1\text{-}C_6)$alkylene-R', or $C(O)N[(C_1\text{-}C_6)alkyl]_2$; wherein alkyl, alkylene and R'' are unsubstituted or substituted. In a more preferred embodiment $R_9$ is OH, halogen, $(C_1\text{-}C_6)$alkyl, $(C_1\text{-}C_6)$alkylene-R', $(C_2\text{-}C_6)$alkenyl, COOH, $CONH_2$, C(O)NH—$(C_1\text{-}C_6)$alkyl, C(O)NHR', or $C(O)N[(C_1\text{-}C_6)alkyl]_2$, wherein alkyl, alkylene and R' are unsubstituted or substituted. More preferably $R_9$ is OH, halogen, $(C_1\text{-}C_6)$alkyl, COOH, $CONH_2$, or O—CH$_3$, wherein alkyl is unsubstituted or substituted. In an even more preferred embodiment R$_9$ is unsubstituted or substituted (C$_1$-C$_6$)alkyl, preferably R$_9$ is unsubstituted (C$_1$-C$_6$) alkyl.

R$_9$ may be bound to any carbon atom of the ring including the position where the linker group L is bound.

As examples for these embodiments, R$_9$ is methyl, ethyl, propyl, isopropyl,

The asterisk (*) denotes where the bond is connected to the C-atom of the ring.

In a preferred embodiment R$_{10}$ is
H,
(C$_6$-C$_{10}$)aryl,
O—(C$_6$-C$_{10}$)aryl,
O—(C$_1$-C$_2$)alkylene-(C$_6$-C$_{10}$)aryl, or
(C$_5$-C$_6$)heteroaryl,
wherein (C$_6$-C$_{10}$)aryl or (C$_5$-C$_6$)heteroaryl are unsubstituted or substituted. Preferably (C$_6$-C$_{10}$)aryl is phenyl.

In a more preferred embodiment R$_{10}$ is H, phenyl, O-phenyl, or (C$_5$-C$_6$)heteroaryl, wherein phenyl or (C$_5$-C$_6$)heteroaryl is unsubstituted or substituted.

In a more preferred embodiment R$_{10}$ is H or phenyl optionally substituted 1, 2 or 3 times, preferably once, by a group independently selected from C(O)NH$_2$, OH, CN, halogen, (C$_1$-C$_6$)alkyl or O—(C$_1$-C$_6$)alkyl, wherein alkyl is unsubstituted or optionally substituted once or more by halogen.

In an even more preferred embodiment R$_{10}$ is H or phenyl optionally substituted independently by a group selected from (C$_1$-C$_6$)alkyl, F, Cl, Br, OMe or CF$_3$.

In a most preferred embodiment R$_{10}$ is H. In still another most preferred embodiment R$_{10}$ is phenyl. Examples for embodiments of R$_{10}$ residues are In a preferred embodiment R$_{11}$ is
H,
(C$_1$-C$_6$)alkyl,
(C$_3$-C$_8$)cycloalkyl, or
(C$_5$-C$_6$)heteroaryl, preferably H or (C$_1$-C$_6$)alkyl, wherein (C$_1$-C$_6$)alkyl, (C$_3$-C$_8$)cycloalkyl, or (C$_5$-C$_{10}$)heteroaryl are unsubstituted or substituted, preferably unsubstituted.

In a more preferred embodiment R$_{11}$ is H or (C$_1$-C$_6$)alkyl, wherein (C$_1$-C$_6$)alkyl is unsubstituted or substituted, preferably unsubstituted. Even more preferred R$_{11}$ is H or methyl. Most preferably R$_{11}$ is H.

In a preferred embodiment R$_{12}$ is
(C$_1$-C$_6$)alkyl, wherein optionally one or more hydrogen are substituted by fluoro;
(C$_3$-C$_8$)cycloalkyl,
(C$_5$-C$_6$)heteroaryl, or
(C$_6$-C$_{10}$)aryl, wherein (C$_3$-C$_8$)cycloalkyl, (C$_5$-C$_6$)heteroaryl and (C$_6$-C$_{10}$)aryl are unsubstituted or substituted, preferably (C$_3$-C$_8$)cycloalkyl, and (C$_5$-C$_6$)heteroaryl are unsubstituted. Preferably (C$_6$-C$_{10}$)aryl is phenyl which is unsubstituted or optionally substituted once or twice by a group selected independently of each other from halogen, (C$_1$-C$_4$)alkyl or O—(C$_1$-C$_4$)alkyl, wherein (C$_1$-C$_4$)alkyl may optionally be substituted by fluoro.

In a preferred embodiment R$_{12}$ is methyl, ethyl, propyl, isopropyl, isobutyl, cyclopropyl, trifluoromethyl, thiazolyl or phenyl unsubstituted or substituted by (C$_1$-C$_4$)alkyl or halogen. More preferred, R$_{12}$ is methyl, ethyl, propyl, isopropyl, isobutyl, cyclopropyl, or is phenyl optionally substituted by methyl or halogen.

In another embodiment R$_{10}$ is H, R$_{11}$ is H and R$_{12}$ is phenyl optionally substituted 1, 2 or 3 times, preferably once, by a group independently selected from halogen, (C$_1$-C$_6$)alkyl or O—(C$_1$-C$_6$)alkyl, wherein alkyl is unsubstituted or optionally substituted once or more by halogen.

In another embodiment R$_{10}$ is phenyl optionally substituted 1, 2 or 3 times, preferably once, by a group independently selected from halogen, (C$_1$-C$_6$)alkyl or O—(C$_1$-C$_6$) alkyl, wherein alkyl is unsubstituted or optionally substituted once or more by halogen; R$_{11}$ is H and R$_{12}$ is unsubstituted ($C_3$-$C_8$)cycloalkyl or ($C_1$-$C_6$)alkyl, wherein in the alkyl optionally one or more hydrogen are substituted by fluoro; ($C_3$-$C_8$)cycloalkyl, or phenyl.

In a further embodiment $R_{11}$ and $R_{12}$, together with the carbon atom to which they are attached, form a ($C_3$-$C_8$)cycloalkyl ring, which is unsubstituted or substituted, preferably unsubstituted. More preferred the ring is cyclopropyl.

In a further embodiment $R_{11}$ and $R_{12}$, together with the carbon atom to which they are attached, form a ($C_3$-$C_8$)heterocycloalkyl ring, which is unsubstituted or substituted. Preferably the formed heterocyclyl group is oxetanyl, morpholinyl, piperidinyl, pyrrolidinyl or piperazinyl. More preferably the heterocyclyl group is morpholinyl or piperazinyl. The formed heterocycloalkyl group is preferably unsubstituted.

In one embodiment of a compound of formula (I) $R_{13}$ and $R_{14}$ are independently of each other
H,
R',
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R',
C(O)($C_1$-$C_6$)alkyl,
C(O)R',
C(O)($C_1$-$C_6$)alkyene-R',
C(O)N[($C_1$-$C_6$)alkyl]$_2$, wherein
R', ($C_1$-$C_6$)alkyl and ($C_1$-$C_6$)alkylene are unsubstituted or substituted.

In a further embodiment $R_{13}$ and $R_{14}$, together with the N-atom to which they are attached, form a ($C_3$-$C_8$)-heterocycloalkyl ring, which is unsubstituted or substituted. Preferably, a ($C_3$-$C_8$)-heterocycloalkyl is unsubstituted.

In a preferred embodiment of a compound of formula (I) $R_{13}$ and $R_{14}$ are independently of each other
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl,
($C_1$-$C_4$)alkylene-O—($C_1$-$C_6$)alkyl,
C(O)($C_1$-$C_6$)alkyl, or
$R_{13}$ and $R_{14}$, together with the N-atom to which they are attached, form a ($C_3$-$C_8$) heterocycloalkyl group,
wherein ($C_1$-$C_6$)alkyl, ($C_3$-$C_8$)cycloalkyl, ($C_1$-$C_4$)alkylene, ($C_5$-$C_{10}$)heteroaryl, ($C_3$-$C_8$)heterocycloalkyl, ($C_6$-$C_{10}$)aryl are unsubstituted or substituted.

Preferably the formed heterocyclyl group in $R_{13}$ and $R_{14}$ is morpholinyl, piperidinyl, pyrrolidinyl or piperazinyl. More preferably the heterocyclyl group is morpholinyl or piperazinyl.

In a more preferred embodiment of a compound of formula (I)
$R_{13}$ is H, ($C_1$-$C_6$)alkyl, ($C_3$-$C_8$)cycloalkyl, or ($C_1$-$C_4$)alkylene-($C_3$-$C_8$)cycloalkyl; and
$R_{14}$ is
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
$C_1$-$C_4$)alkylene-($C_6$-$C_{10}$)aryl,
($C_1$-$C_4$)alkylene-O—($C_1$-$C_6$)alkyl, or
C(O)($C_1$-$C_6$)alkyl.

wherein ($C_1$-$C_6$)alkyl, ($C_3$-$C_8$)cycloalkyl, ($C_1$-$C_4$)alkylene, ($C_3$-$C_8$)heterocycloalkyl, ($C_6$-$C_{10}$)aryl are unsubstituted or substituted.

In an even more preferred embodiment of a compound of formula (I)
$R_{13}$ is H or ($C_1$-$C_6$)alkyl; and
$R_{14}$ is
H,
($C_1$-$C_6$)alkyl,
($C_3$-$C_8$)cycloalkyl,
($C_1$-$C_4$)alkylene-($C_3$-$C_8$)cycloalkyl,
($C_1$-$C_4$)alkylene-($C_5$-$C_{10}$)heteroaryl,
($C_1$-$C_4$)alkylene-($C_3$-$C_8$)heterocycloalkyl,
($C_1$-$C_4$)alkylene-($C_6$-$C_{10}$)aryl, or
($C_1$-$C_4$)alkylene-O—($C_1$-$C_6$)alkyl.
wherein ($C_1$-$C_6$)alkyl, ($C_3$-$C_8$)cycloalkyl, ($C_1$-$C_4$)alkylene, ($C_3$-$C_8$)heterocycloalkyl, ($C_6$-$C_{10}$)aryl are unsubstituted or substituted.

More preferably $R_{13}$ is H, ($C_1$-$C_6$)alkyl and
$R_{14}$ is H, ($C_1$-$C_6$)alkyl or ($C_3$-$C_8$)cycloalkyl, wherein ($C_1$-$C_6$) alkyl or ($C_3$-$C_8$)cycloalkyl are unsubstituted or substituted, preferably unsubstituted.

In a further embodiment $R_{13}$ is H and
$R_{14}$ is H, ($C_1$-$C_6$)alkyl or ($C_3$-$C_8$)cycloalkyl
wherein ($C_1$-$C_6$)alkyl or ($C_3$-$C_8$)cycloalkyl are unsubstituted.

Most preferred $R_{13}$ and $R_{14}$ are H.

As examples for the before mentioned embodiments, $R_{13}$ or $R_{14}$ are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

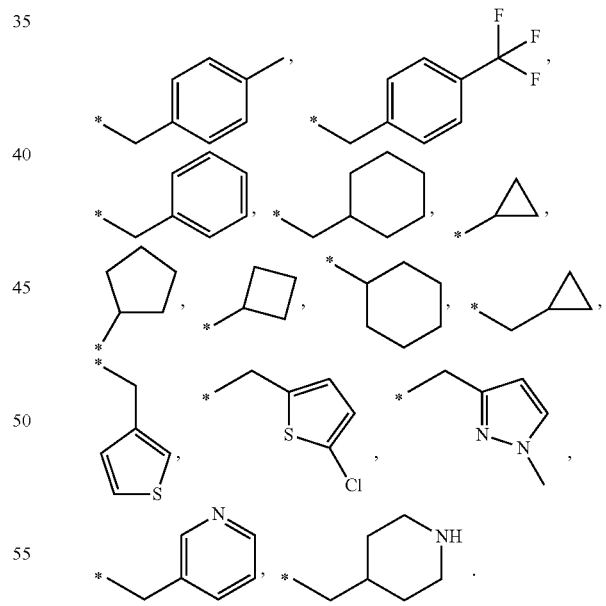

The asterisk (*) denotes where the bond is connected to the N-atom of the amine.

In one embodiment $R_{15}$ is H or ($C_1$-$C_6$)alkyl, which is unsubstituted or optionally substituted, more preferably $R_{15}$ is H or ($C_1$-$C_4$)alkyl, most preferably H. Preferably, the alkyl is unsubstituted.

In one embodiment of a compound of formula (I) $R_6$ is absent or the bicyclus or the adamantane formed with $R_6$ is selected from the group of

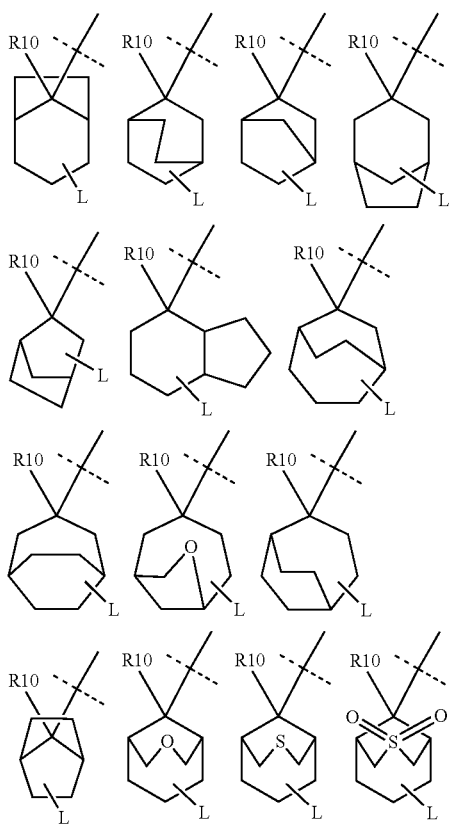

(the bond with the dotted line indicates the position of the —(CR$_{11}$R$_{12}$)$_r$NR$_{13}$R$_{14}$ residue)
or

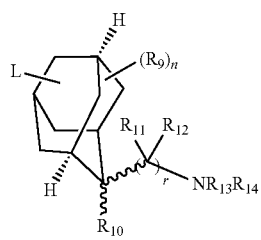

which is unsubstituted or optionally substituted by R$_9$. In a preferred embodiment the bicyclus or adamantane is unsubstituted (n is 0) or is substituted once (n=1).

Preferably the unsubstituted or substituted adamantane has the following structure

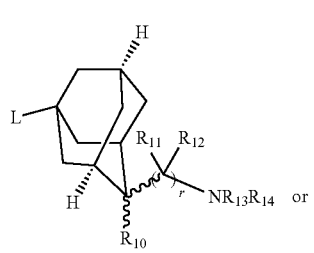

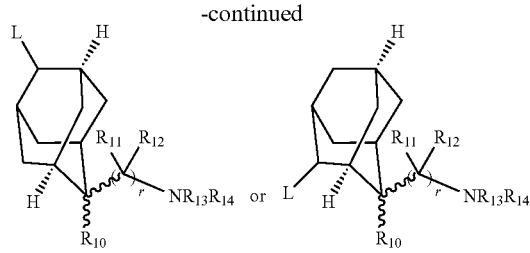

The cis and trans isomers in these adamantane residues such as for example in the structures

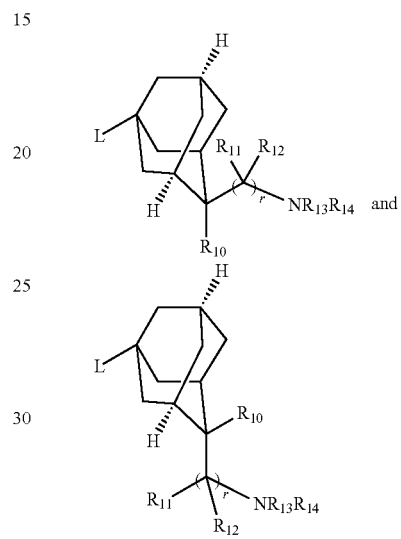

are included.

In one embodiment of a compound of formula (I) R$_6$ is absent, i.e. no bicyclus or adamantane is formed.

In one embodiment m is 2 and s is 2 resulting in a residue within a compound of formula (I) of the formula

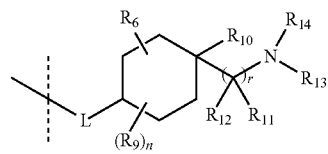

in all their stereochemical forms.

In another embodiment m is 3 and s is 1 resulting in a residue within a compound of formula (I) of the formula

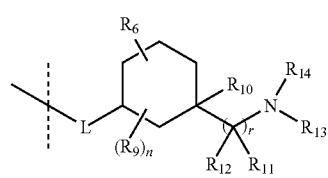

In a further embodiment m is 2 and s 1. In still another embodiment m is 3 and s is 0. In yet another embodiment m is 4 and s is 0.

In one embodiment of a compound of formula (I) n is 0, 1, or 2. More preferred, n is 0 or 1. Most preferred n is 0.

In a preferred embodiment r is 1.

In another embodiment L is $O(CH_2)_p$. In a further embodiment L is $S(CH_2)_p$, $S(O)(CH_2)_p$ or $SO_2(CH_2)_p$. In another embodiment L is $NH(CH_2)_p$, $N[(C_1-C_6)alkyl](CH_2)_p$, $N[(C_3-C_6)cycloalkyl](CH_2)_p$, $N[(C_1-C_3)alkylene-aryl](CH_2)_p$ or $N[(C_1-C_3)alkylene-(C_5-C_6)heteroaryl](CH_2)_p$ with $NH(CH_2)_p$, $N(C_1-C_6)alkyl-(CH_2)_p$ being more preferred. A preferred $N(C_1-C_6)alkyl$ is $N(C_1-C_4)alkyl$, more preferably $NCH_3$ or $NCH_2CH_3$ with $NCH_3$ being more preferred. In a preferred embodiment L is $O(CH_2)_p$. In another preferred embodiment L is $S(CH_2)_p$. In a further embodiment L is $NH(CH_2)_p$. Most preferred L is O, S or NH with O being especially preferred.

Preferably p is 0, 1, 2, or 3, more preferred 0 or 1, with 0 being most preferred;

More preferably, m is 2 and s is 2 and L is O, S or NH, preferably O.

In a further embodiment the present invention relates to a compound of formula (I) selected from the group consisting of 6-[4-(1-Amino-propyl)-4-(4-fluoro-phenyl)-cyclohexyloxy]-7-chloro-2H-isoquinolin-1-one,
6-[4-(1-Amino-cyclopropyl)-4-phenyl-cyclohexyloxy]-7-chloro-2H-isoquinolin-1-one,
6-{[4-(1-aminopropyl)-4-phenylcyclohexyl]oxy}-7-chloroisoquinolin-1(2H)-one,
6-[4-(1-Amino-butyl)-4-phenyl-cyclohexyloxy]-7-chloro-2H-isoquinolin-1-one,
6-[4-(1-Amino-butyl)-4-(4-fluoro-phenyl)-cyclo-hexyloxy]-7-chloro-2H-isoquinolin-1-one,
6-[4-(1-Amino-propyl)-4-(4-bromo-phenyl)-cyclohexyloxy]-7-chloro-2H-isoquinolin-1-one,
6-[4-(1-Amino-propyl)-4-(2-bromo-phenyl)-cyclohexyloxy]-7-chloro-2H-isoquinolin-1-one,
6-[4-(1-Amino-propyl)-4-(4-trifluoromethyl-phenyl)-cyclohexyloxy]-7-chloro-2H-isoquinolin-1-one,
6-[4-(1-Amino-propyl)-4-(2-fluoro-phenyl)-cyclohexyloxy]-7-chloro-2H-isoquinolin-1-one,
6-[4-(1-Amino-propyl)-4-(2-chloro-phenyl)-cyclohexyloxy]-7-chloro-2H-isoquinolin-1-one,
6-[4-(1-Amino-propyl)-4-phenyl-cyclohexyloxy]-7-methyl-2H-isoquinolin-1-one,
6-[4-(1-Amino-ethyl)-4-(4-fluoro-phenyl)-cyclohexyloxy]-7-chloro-2H-isoquinolin-1-one,
6-[4-(Amino-phenyl-methyl)-4-(4-fluoro-phenyl)-cyclohexyloxy]-7-chloro-2H-isoquinolin-1-one,
6-[4-(1-Amino-2-methyl-propyl)-4-phenyl-cyclohexyloxy]-7-chloro-2H-isoquinolin-1-one,
6-[4-(1-Amino-3-methyl-butyl)-4-phenyl-cyclohexyloxy]-7-chloro-2H-isoquinolin-1-one,
6-[4-(Amino-phenyl-methyl)-4-phenyl-cyclo-hexyloxy]-7-chloro-2H-isoquinolin-1-one,
6-[4-(1-Amino-1-methyl-ethyl)-4-(4-fluoro-phenyl)-cyclohexyloxy]-7-chloro-2H-isoquinolin-1-one,
6-[4-(1-Amino-cyclopropyl)-4-(2-fluoro-phenyl)-cyclohexyloxy]-7-chloro-2H-isoquinolin-1-one,
6-[4-(1-Amino-ethyl)-4-phenyl-cyclohexyloxy]-7-chloro-2H-isoquinolin-1-one,
6-[4-(1-Amino-1-methyl-ethyl)-4-phenyl-cyclo-hexyloxy]-7-chloro-2H-isoquinolin-1-one,
6-(4-[amino(cyclopropyl)methyl]-4-phenyl-cyclohexyl}oxy)-7-chloroisoquinolin-1(2H)-one,
6-[4-(1-Amino-propyl)-4-(4-isopropyl-phenyl)-cyclohexyloxy]-7-chloro-2H-isoquinolin-1-one,
6-[4-(1-Amino-propyl)-4-(3-methoxy)-phenyl)-cyclohexyloxy]-7-chloro-2H-isoquinolin-1-one,
6-[4-(1-Amino-propyl)-4-(3-bromo-phenyl)-cyclohexyloxy]-7-chloro-2H-isoquinolin-1-one,
6-[4-(1-Amino-2-methyl-propyl)-4-(4-fluoro-phenyl)-cyclohexyloxy]-7-chloro-2H-isoquinolin-1-one, or
6-[4-(1-Amino-propyl)-4-phenyl-cyclohexyloxy]-4-bromo-7-chloro-2H-isoquinolin-1-one;
their stereoisomeric and/or tautomeric forms and/or their pharmaceutically acceptable salts thereof.

In a further embodiment a compound of formula (I) is selected from the group consisting of cis-6-[4-(1-Amino-propyl)-4-(4-fluoro-phenyl)-cyclohexyloxy]-7-chloro-2H-isoquinolin-1-one,
trans-6-[4-(1-amino-propyl)-4-(4-fluoro-phenyl)-cyclohexyloxy]-7-chloro-2H-isoquinolin-1-on,
cis-6-[4-(1-Amino-cyclopropyl)-4-phenyl-cyclohexyloxy]-7-chloro-2H-isoquinolin-1-one,
cis-6-{[4-(1-aminopropyl)-4-phenylcyclohexyl]oxy}-7-chloro-2H-isoquinolin-1-one,
trans-6-[4-(1-amino-propyl)-4-phenyl)-cyclohexyloxy]-7-chloro-2H-isoquinolin-1-one,
cis-6-[4-(1-Amino-butyl)-4-phenyl-cyclohexyloxy]-7-chloro-2H-isoquinolin-1-one,
trans-6-[4-(1-Amino-butyl)-4-phenyl-cyclohexyloxy]-7-chloro-2H-isoquinolin-1-one,
cis-6-[4-(1-Amino-butyl)-4-(4-fluoro-phenyl)-cyclo-hexyloxy]-7-chloro-2H-isoquinolin-1-one,
trans-6-[4-(1-Amino-butyl)-4-(4-fluoro-phenyl)-cyclohexyloxy]-7-chloro-2H-isoquinolin-1-one,
cis-6-[4-(1-Amin-propyl)-4-(4-bromo-phenyl)-cyclohexyloxy]-7-chloro-2H-isoquinolin-1-one,
cis-6-[4-(1-Amino-propyl)-4-(2-bromo-phenyl)-cyclohexyloxy]-7-chloro-2H-isoquinolin-1-one,
cis-6-[4-(1-Amino-propyl)-4-(4-trifluoromethyl-phenyl)-cyclo-hexyloxy]-7-chloro-2H-isoquinolin-1-one,
cis-6-[4-(1-Amino-propyl)-4-(2-fluoro-phenyl)-cyclohexyloxy]-7-chloro-2H-isoquinolin-1-one,
cis-6-[4-(1-Amino-propyl)-4-(2-chloro-phenyl)-cyclohexyloxy]-7-chloro-2H-isoquinolin-1-one,
cis-6-[4-(1-Amino-propyl)-4-phenyl-cyclohexyloxy]-7-methyl-2H-isoquinolin-1-one,
cis-6-[4-(1-Amino-ethyl)-4-(4-fluoro-phenyl)-cyclo-hexyloxy]-7-chloro-2H-isoquinolin-1-one,
trans-6-[4-(1-Amino-ethyl)-4-(4-fluoro-phenyl)-cyclohexyloxy]-7-chloro-2H-isoquinolin-1-one,
cis-6-[4-(1-Amino-propyl)-4-(3-bromo-phenyl)-cyclohexyloxy]-7-chloro-2H-isoquinolin-1-one,
trans-6-[4-(1-Amino-propyl)-4-(3-bromo-phenyl)-cyclohexyloxy]-7-chloro-2H-isoquinolin-1-one,
cis-6-[4-(1-Amino-propyl)-4-(3-methoxy)-phenyl)-cyclohexyloxy]-7-chloro-2H-isoquinolin-1-one,
trans-6-[4-(1-Amino-propyl)-4-(3-methoxy-phenyl)-cyclohexyloxy]-7-chloro-2H-isoquinolin-1-one,
trans-6-[4-(Amino-phenyl-methyl)-4-(4-fluoro-phenyl)-cyclohexyloxy]-7-chloro-2H-isoquinolin-1-one,
trans-6-[4-(1-Amino-2-methyl-propyl)-4-phenyl-cyclohexyloxy]-7-chloro-2H-isoquinolin-1-one,
trans-6-[4-(1-Amino-3-methyl-butyl)-4-phenyl-cyclohexyloxy]-7-chloro-2H-isoquinolin-1-one,
trans-6-[4-(Amino-phenyl-methyl)-4-phenyl-cyclo-hexyloxy]-7-chloro-2H-isoquinolin-1-one,
trans-6-[4-(1-Amino-1-methyl-ethyl)-4-(4-fluoro-phenyl)-cyclohexyloxy]-7-chloro-2H-isoquinolin-1-one,
cis-6-[4-(1-Amino-cyclopropyl)-4-(2-fluoro-phenyl)-cyclo-hexyloxy]-7-chloro-2H-isoquinolin-1-one,
cis-6-[4-(1-Amino-ethyl)-4-phenyl-cyclohexyloxy]-7-chloro-2H-isoquinolin-1-one, cis-6-[4-(1-Amino-1-methyl-ethyl)-4-phenyl-cyclo-hexyloxy]-7-chloro-2H-isoquinolin-1-one,
cis-6-(4-[amino(cyclopropyl)methyl]-4-phenyl-cyclohexyl}oxy)-7-chloro-2H-isoquinolin-1-one,
cis-6-[4-(1-Amino-propyl)-4-(4-isopropyl-phenyl)-cyclohexyloxy]-7-chloro-2H-isoquinolin-1-one,
cis-6-[4-(1-Amino-2-methyl-propyl)-4-(4-fluoro-phenyl)-cyclohexyloxy]-7-chloro-2H-isoquinolin-1-one, and
cis-6-[4-(1-Amino-propyl)-4-phenyl-cyclohexyloxy]-4-bromo-7-chloro-2H-isoquinolin-1-one,
and their stereoisomeric and/or tautomeric forms and/or their pharmaceutically acceptable salts thereof.

In a further embodiment a compound of formula (I) is selected from the group of
trans-6-[4-((S)-Amino-phenyl-methyl)-4-phenyl-cyclohexyloxy]-7-chloro-2H-isoquinolin-1-one,
trans-6-[4-((R)-Amino-phenyl-methyl)-4-phenyl-cyclohexyloxy]-7-chloro-2H-isoquinolin-1-one,
cis-6-[4-((S)-1-Amino-propyl)-4-phenyl-cyclohexyloxy]-7-chloro-2H-isoquinolin-1-one,
cis-6-[4-((R)-1-Amino-propyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((S)-1-Amino-ethyl)-4-phenyl-cyclohexyloxy]-7-chloro-2H-isoquinolin-1-one,
cis-6-[4-((R)-1-Amino-ethyl)-4-phenyl-cyclohexyloxy]-7-chloro-2H-isoquinolin-1-one,
6-{4-[(S)-Amino-(4-fluoro-phenyl)-methyl]-cyclohexyloxy}-7-chloro-2H-isoquinolin-1-one,
6-{4-[(R)-Amino-(4-fluoro-phenyl)-methyl]-cyclohexyloxy}-7-chloro-2H-isoquinolin-1-one,
cis-6-[4-((R)-1-Amino-propyl)-4-phenyl-cyclohexyloxy]-7-chloro-2H-isoquinolin-1-one, and
cis-6-[4-((S)-1-Amino-propyl)-4-phenyl-cyclohexyloxy]-7-chloro-2H-isoquinolin-1-one,
their tautomeric forms and/or pharmaceutically acceptable salts thereof.

In a further embodiment a compound of formula (I) is selected from the group consisting of
cis-6-[4-(1-Amino-propyl)-4-pyridin-2-yl-cyclohexyloxy]-7-chloro-2H-isoquinolin-1-one,
cis-6-[4-(1-Amino-propyl)-4-(2,4-difluoro-phenyl)-cyclohexyloxy]-7-chloro-2H-isoquinolin-1-one,
cis-6-[4-(1-Amino-propyl)-4-(4-fluoro-2-methyl-phenyl)cyclohexyloxy]-7-chloro-2H-isoquinolin-1-one,
cis-6-[4-(1-Amino-propyl)-4-(3,5-difluoro-phenyl)-cyclohexyloxy]-7-chloro-2H-isoquinolin-1-one,
cis-6-[4-(1-Amino-propyl)-4-(3,4-difluoro-phenyl)-cyclohexyloxy]-7-chloro-2H-isoquinolin-1-one,
cis-6-[4-(1-Amino-propyl)-4-o-tolyl-cyclohexyloxy]-7-chloro-2H-isoquinolin-1-one,
cis-6-[4-(1-Amino-propyl)-4-(2-trifluoromethoxy-phenyl)-cyclohexyloxy]-7-chloro-2H-isoquinolin-1-one,
cis-6-[4-(1-Amino-propyl)-4-(4-fluoro-3-methoxy-phenyl)-cyclohexyloxy]-7-chloro-2H-isoquinolin-1-one,
cis-6-[4-(1-Amino-propyl)-4-(3-ethoxy-phenyl)-cyclohexyloxy]-7-chloro-2H-isoquinolin-1-one,
cis-6-[4-(1-Amino-propyl)-4-(3-methoxy-4-methyl-phenyl)-cyclohexyloxy]-7-chloro-2H-isoquinolin-1-one,
cis-6-[4-(1-Amino-propyl)-4-(3,4-difluoro-phenyl)-cyclohexyloxy]-7-methyl-2H-isoquinolin-1-one,
cis-6-[4-(1-Amino-propyl)-4-(3,5-difluoro-phenyl)-cyclohexyloxy]-7-fluoro-2H-isoquinolin-1-one,
cis-6-[4-(1-Amino-propyl)-4-(3,4-difluoro-phenyl)-cyclohexyloxy]-7-fluoro-5-methyl-2H-isoquinolin-1-one,
cis-6-[4-(1-Amino-propyl)-4-(3,5-difluoro-phenyl)-cyclohexyloxy]-7-methoxy-2H-isoquinolin-1-one,
cis-6-[4-(1-Amino-propyl)-4-(2-methoxy-phenyl)-cyclohexyloxy]-7-chloro-2H isoquinolin-1-one
cis-6-[4-(1-Amino-propyl)-4-(4-trifluoro-methoxy-phenyl)-cyclohexyloxy]-7-chloro-2H-isoquinolin-1-one,
cis-6-[4-(1-Amino-1-methyl-ethyl)-4-(4-fluoro-phenyl)-cyclohexyloxy]-7-chloro-2H-isoquinolin-1-one,
cis-6-[4-(1-Amino-propyl)-4-(3,5-difluoro-phenyl)-cyclohexyloxy]-4-benzyl-7-chloro-2H-isoquinolin-1-one,
cis-6-[4-(1-Amino-propyl)-4-(3,5-difluoro-phenyl)-cyclohexyloxy]-5-chloro-2H-isoquinolin-1-one,
cis-6-[4-(1-Amino-propyl)-4-(3,5-difluoro-phenyl)-cyclohexyloxy]-5,7-dimethyl-2H-isoquinolin-1-one,
cis-6-[4-(Amino-cyclopropyl-methyl)-4-(4-fluoro-phenyl)-cyclohexyloxy]-7-chloro-2H-isoquinolin-1-one,
cis-6-[4-(1-Amino-propyl)-4-(3-trifluoromethyl-phenyl)-cyclohexyloxy]-7-chloro-2H-isoquinolin-1-one,
cis-6-[4-(1-Amino-propyl)-4-(3-trifluoromethoxy-phenyl)-cyclohexyloxy]-7-chloro-2H-isoquinolin-1-one,
cis-6-[4-(1-Amino-propyl)-4-(3-trifluoromethoxy-phenyl)-cyclohexyloxy]-7-methyl-2H-isoquinolin-1-one,
cis-6-[4-(1-Amino-propyl)-4-(3-trifluoromethyl-phenyl)-cyclohexyloxy]-7-methyl-2H-isoquinolin-1-one,
cis-6-[4-(1-Amino-propyl)-4-phenyl-cyclohexyloxy]-7-fluoro-2H-isoquinolin-1-one,
cis-6-[4-(1-Amino-propyl)-4-phenyl-cyclohexyloxy]-7-fluoro-5-methyl-2H-isoquinolin-1-one,
cis-6-[4-(1-Amino-propyl)-4-phenyl-cyclohexyloxy]-4-benzyl-7-chloro-2H-isoquinolin-1-one,
cis-4-[1-(1-Amino-propyl)-4-(7-chloro-1-oxo-1,2-dihydro-isoquinolin-6-yloxy)-cyclohexyl]-benzonitrile,
cis-3-[1-(1-Amino-propyl)-4-(7-chloro-1-oxo-1,2-dihydro-isoquinolin-6-yloxy)-cyclohexyl]benzonitrile,
6-[cis-4-(1-Amino-propyl)-4-(3-methanesulfonyl-phenyl)-cyclohexyloxy]-7-chloro-2H-isoquinolin-1-one,
6-[(1S,4S,5S)-5-(1-Amino-propyl)-5-phenyl-bicyclo[2.2.1]hept-2-yloxy]-7-chloro-2H-isoquinolin-1-one,
6-[(1R,4R,5R)-5-(1-Amino-propyl)-5-phenyl-bicyclo[2.2.1]hept-2-yloxy]-7-chloro-2H-isoquinolin-1-one,
cis-6-[4-(1-Benzylamino-propyl)-4-phenyl-cyclohexyloxy]-7-methyl-2H-isoquinolin-1-one,
cis-6-[4-(1-Diethylamino-propyl)-4-phenyl-cyclohexyloxy]-7-methyl-2H-isoquinolin-1-one,
cis-7-Methyl-6-[4-(1-propylamino-propyl)-4-(3-trifluoromethyl-phenyl)-cyclohexyloxy]-2H-isoquinolin-1-one,
cis-6-[4-(1-Benzylamino-propyl)-4-phenyl-cyclohexyloxy]-7-chloro-2H-isoquinolin-1-one,
cis-7-Chloro-6-[4-(1-isobutylamino-propyl)-4-phenyl-cyclohexyloxy]-2H-isoquinolin-1-one,
cis-6-[4-(1-Butylamino-propyl)-4-phenyl-cyclohexyloxy]-7-chloro-2H-isoquinolin-1-one,
cis-7-Chloro-6-{4-[1-(cyclopropylmethyl-amino)-propyl]-4-phenyl-cyclohexyloxy}-2H-isoquinolin-1-one,
cis-6-[4-(2-Amino-propyl)-4-(4-fluoro-phenyl)-cyclohexyloxy]-7-chloro-2H-isoquinolin-1-one,
cis-6-[4-(2-Amino-butyl)-4-(4-fluoro-phenyl)-cyclohexyloxy]-7-chloro-2H-isoquinolin-1-one,
cis-6-[4-(1-Amino-2-fluoro-ethyl)-4-(4-fluoro-phenyl)-cyclohexyloxy]-7-chloro-2H-isoquinolin-1-one, cis-6-[4-(1-Amino-3-methoxy-propyl)-4-(4-fluoro-phenyl)-cyclohexyloxy]-7-chloro-2H-isoquinolin-1-one,
6-[3-(1-Amino-propyl)-3-(4-fluoro-phenyl)-cyclobutyloxy]-7-chloro-2H-isoquinolin-1-one, and
6-[3-(1-Amino-propyl)-3-(4-fluoro-phenyl)-cyclopentyloxy]-7-chloro-2H-isoquinolin-1-one,
and their stereoisomeric and/or tautomeric forms and/or their pharmaceutically acceptable salts thereof.

In a further embodiment a compound of formula (I) is selected from the group consisting of
cis-1-[4-(7-Chloro-isoquinolin-6-yloxy)-1-(3,4-difluoro-phenyl)-cyclohexyl]-propylamine,
cis-1-[4-(7-Bromo-isoquinolin-6-yloxy)-1-(3,4-difluoro-phenyl)-cyclohexyl]-propylamine,
cis-1-[1-(3,5-Difluoro-phenyl)-4-(5,7-dimethyl-isoquinolin-6-yloxy)-cyclohexyl]-propylamine,
cis-1-[1-(3,5-Difluoro-phenyl)-4-(7-fluoro-5-methyl-isoquinolin-6-yloxy)-cyclohexyl]-propylamine,
cis-1-[1-(3,4-Difluoro-phenyl)-4-(7-fluoro-isoquinolin-6-yloxy)-cyclohexyl]-propylamine,
cis-1-[4-(7-Chloro-isoquinolin-6-yloxy)-1-(3,5-difluoro-phenyl)-cyclohexyl]-propylamine,
cis-1-[4-(5-Chloro-isoquinolin-6-yloxy)-1-(3,5-difluoro-phenyl)-cyclohexyl]-propylamine,
cis-1-[4-(7-Chloro-isoquinolin-6-yloxy)-1-phenyl-cyclohexyl]-propylamine,
cis-1-[4-(5,7-Dimethyl-isoquinolin-6-yloxy)-1-phenyl-cyclohexyl]-propylamine,
cis-1-[4-(7-Fluoro-isoquinolin-6-yloxy)-1-phenyl-cyclohexyl]-propylamine,
cis-1-[4-(5-Chloro-isoquinolin-6-yloxy)-1-phenyl-cyclohexyl]-propylamine,
cis-1-[4-(7-Fluoro-5-methyl-isoquinolin-6-yloxy)-1-phenyl-cyclohexyl]-propylamine,
cis-1-[4-(7-Bromo-isoquinolin-6-yloxy)-1-phenyl-cyclohexyl]-propylamine,
cis-1-[4-(7-Methyl-isoquinolin-6-yloxy)-1-phenyl-cyclohexyl]-propylamine,
cis-6-[4-(1-Amino-propyl)-4-phenyl-cyclohexyloxy]-7-chloro-isoquinolin-1-ylamine,
[4-(1-Amino-propyl)-4-(4-methoxy-phenyl)-cyclohexyl]-isoquinolin-6-yl-amine, and
1-Amino-[4-(1-amino-propyl)-4-(4-methoxy-phenyl)-cyclohexyl]-isoquinolin-6-yl-amine,
and their stereoisomeric and/or tautomeric forms and/or their pharmaceutically acceptable salts thereof.

In a further embodiment the present invention relates to a compound of formula (I) selected from the group consisting of
6-[4-(1-Amino-1-phenyl-ethyl)-cyclohexyloxy]-7-chloro-2H-isoquinolin-1-one,
6-{-4-[Amino-(4-methoxy-phenyl)-methyl]-cyclohexyloxy}-7-chloro-2H-isoquinolin-1-one,
6-{4-[Amino-(4-fluoro-phenyl)-methyl]-cyclohexyloxy}-7-chloro-2H-isoquinolin-1-one,
6-[4-(Amino-p-tolyl-methyl)-cyclohexyloxy]-7-chloro-2H-isoquinolin-1-one, or
6-[4-(Amino-phenyl-methyl)-cyclohexyloxy]-7-chloro-2H-isoquinolin-1-one,
their stereoisomeric and/or tautomeric forms and/or their pharmaceutically acceptable salts thereof.

In a further embodiment a compound of formula (I) is selected from the group consisting of
6-{-4-[1-Amino-1-(4-fluoro-phenyl)-ethyl]-cyclohexyloxy}-7-chloro-2H-isoquinolin-1-one,
6-{4-[1-Amino-1-(4-methoxy-phenyl)-ethyl]-cyclohexyloxy}-7-chloro-2H-isoquinolin-1-one,
6-{4-[1-Amino-1-cyclopentyl-ethyl]-cyclohexyloxy}-7-chloro-2H-isoquinolin-1-one,
6-{4-[1-Amino-1-ethyl-propyl]-cyclohexyloxy}-7-chloro-2H-isoquinolin-1-one,
6-{4-[1-Amino-1-cyclopropyl-ethyl]-cyclohexyloxy}-7-chloro-2H-isoquinolin-1-one,
6-{4-[1-Amino-1-n-propyl-ethyl]-cyclohexyloxy}-7-chloro-2H-isoquinolin-1-one,
6-[4-(1-Amino-propyl)-cyclohexyloxy]-7-chloro-2H-isoquinolin-1-one, and
6-[4-(Amino-cyclopropyl-methyl)-cyclohexyloxy]-7-chloro-2H-isoquinolin-1-one,
their stereoisomeric and/or tautomeric forms and/or their pharmaceutically acceptable salts thereof.

In any embodiments of the present invention one or more or all of the groups contained in the compounds of formula (I) can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formula (I) in all stereoisomeric forms and mixtures of stereoisomeric forms in all ratios, and their pharmaceutically acceptable salts.

Isoquinoline substitution pattern is numbered according to IUPAC rules:

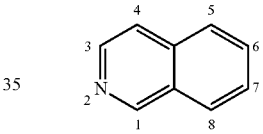

The term isoquinolone and isoquinolinone are used synonymously. All references to "compound(s) of formula (I)" herein refer to compound(s) of the formula (I), (II) (IIIa), (IIIb) and (IV) as described above, and their pharmaceutically acceptable salts, and/or to their stereoisomeric forms, polymorphs and solvates. Physiologically functional derivatives as described herein are also included.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The present invention also includes physiologically functional derivatives of a compound of formula (I). A physiologically functional derivative as used herein refers to any physiologically tolerated derivative of a compound of the formula (I) of the invention, for example an N-oxide, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to compounds of the formula (I) in the form of their stereoisomeric forms, which include racemates, enantiomerically enriched mixtures, pure enantiomers and diastereomers and mixtures in any ratio thereof.

The compounds of the invention may also exist in various polymorphous forms, for example as amorphous and crystalline polymorphous forms. All polymorphous forms of the compounds of the invention belong within the framework of the invention and are a further aspect of the invention.

If radicals or substituents may occur more than once in the compounds of the formula (I), they may all, independently of one another, have the stated meaning and be identical or different.

The present invention also relates to the compounds of the formula (I) and/or their pharmaceutically acceptable salts and/or their prodrugs for use as pharmaceuticals (or medicaments), to the use of the compounds of the formula (I) and/or their pharmaceutically acceptable salts and/or their prodrugs for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

In a further embodiment the invention also relates to the use of a compound of formula (I) and/or a pharmaceutically acceptable salt thereof for the treatment and/or prevention of hypertension, pulmonary hypertension, fibroid liver, liver failure, nephropathy, renal failure, chronic obstructive pulmonary disease (COPD), cerebral vasospasm, pain, spinal cord injury, erectile dysfunction, blood vessel restenosis, or cancer development and progression.

In a further embodiment the invention also relates to the use of a compound of formula (I) and/or a pharmaceutically acceptable salt thereof for curative approaches associated with stem cell or induced pluripotent stem cell treatment, improvement of recognition or for treatment or prevention of depression, epilepsy, fibroid heart, renal papillary necrosis, tubulo-interstitial dysfunction, multiple sclerosis, vessel stenosis for example carotid stenosis or lipid disorders.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i.e. one or more pharmaceutically acceptable carrier substances (or vehicles) and/or additives (or excipients).

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I, for example by introduction of substituents or modification of functional groups.

Compounds of formula (I) may be made in the following manner:

Compounds of the general formula (I) can be assembled from a suitably substituted isoquinoline moiety and a suitably substituted cycloalkyl amine moiety.

Isoquinolines and isoquinolones like (i) or (ii), bearing a useful residue for coupling in 6-position, can be obtained by a wide variety of methods, for example reviewed in Alvarez et al. Science of Synthesis 2005, 15, 661-838 and 839-906 and references cited therein. Isoquinolines can also be converted to isoquinolones by methods described in the literature e.g. WO 2007/012421 or WO 2007/012422, like conversion of a suitable isoquinoline into the corresponding N-oxide with an oxidating agent like hydrogen peroxide or metachloro perbenzoic acid and subsequent conversion into the corresponding 1-chloro derivative by a chlorinating agent like phosphorous oxy chloride, followed by displacement of the chlorine by an alcohol under basic condition like sodium methoxide in methanol or conversion into the corresponding 2H-isoquinolone by for example treatment with ammonium acetate in acetic acid at elevated temperature. Also the N-oxide can be directly converted into the corresponding 1-alkoxy derivative by reacting it with a suitable chloroformiate in an alcoholic solvent like methanol in presence of a base like triethylamine. It is understood, that the hydroxyl-group in 6-position of (ii) can be liberated at a suitable stage of the synthesis e.g. from treatment of a corresponding 6-methoxy derivative with lewis acids like aluminium chloride or boron tribromide. It is furthermore understood, that 2H-isoquinolones can be converted into suitably protected 1-alkoxy isoquinolones by a variety of methods e.g. treatment of the corresponding 2H-isoquinolones with alkylating agents like benzyl bromide or methyl iodide in the presence of a suitable base like silver carbonate or triethyl amine in a suitable solvent like toluene or THF, or conversion of the said 2H-isoquinolones into their 1-chloro derivatives by treatment with a chlorinating agent like phosphorous oxychloride, followed by displacement of the chlorine by an alcohol e.g. under basic conditions like sodium methoxide in methanol. It is understood, that residues $R_3$, $R_4$, $R_5$, $R_7$, and/or $R_8$ can either be incorporated in the starting materials for the synthesis of the respective isoquinoline or isoquinolone or can be introduced at a suitable later stage e.g. by halogenation like bromination or chlorination and subsequent replacement of said halogen by methods well precedented in the literature like for example Suzuki or Hartwig Buchwald couplings using appropriate catalysts and coupling partners like boronic acids, amines or anilines.

One possible synthesis for a cycloalkyl amine substituted isoquinolinone (v) with L=O is described below in an exemplary fashion, but does not limit the present invention. The cycloalkyl amine substituted isoquinolinones (for example compound v) can be synthesized via a variety of methods. The following general scheme 1 illustrates some of the possible ways to access the isoquinolinones, but does not limit the present invention.

Scheme 1

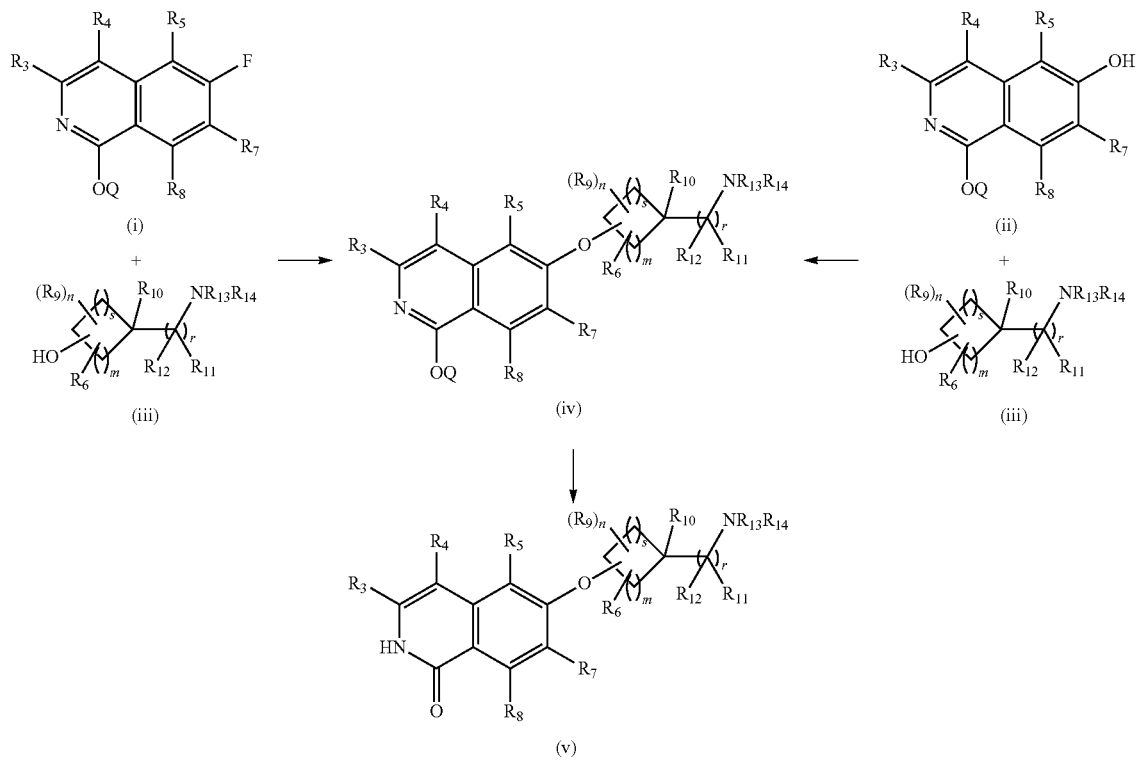

6-Fluoro-isoquinolones (i), for example substituted by $R_3$, $R_4$, $R_5$, $R_7$, and/or $R_8$ being for instance independently from each other substituents like hydrogen, alkyl, alkoxy or halide, can be reacted with suitable $R_{13}/R_{14}$ substituted amino alcohols wherein $R_{13}/R_{14}$ are independently from each other for example hydrogen, alkyl or a protecting group like for example Boc or Cbz in the presence of base such as DBU, cesium carbonate, or sodium hydride at temperatures ranging from ambient to 100° C. to give the corresponding derivatives (iv). Optionally, this conversion can already be performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

Alternatively, the amino alcohols can be coupled to 6-hydroxy-isoquinolones, such as (ii), under inversion of the hydroxyl bearing carbon center of compounds like (iii), either protected with a suitable protecting group Q or unprotected, via a Mitsunobu reaction using triphenylphosphine and dialkylazodicarboxylates such as diethylazodicarboxylate or diisopropylazodicarboxylate in a suitable solvent like tetrahydrofuran, or toluene. The products like (iv) obtained via these methods can then either be liberated to give compounds of type (v) or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step, like for example acidic removal of Boc-groups. Furthermore an amino group can be acylated by reacting it with a suitable acid chloride in the presence of a base like triethyl amine or Hünig's base or by reacting it with a suitable carboxylic acid in the presence of a base like triethylamine or Hünig's base and a coupling reagent like EDC, PyBOP or TOTU.

In case of use of protected isoquinolones, cleavage of the used protection groups is required to liberate the desired isoquinolone (v). This liberation, however, can be performed before or after the reductive amination step, depending on the nature of the used aldehyde/ketone and the protection group used.

Isoquinolone derivatives like (v) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The cycloalkyl amine moieties like for example (iii) can by synthesized via a variety of methods. The following general schemes illustrate some of the possible ways to access the amines, but do not limit the present invention. It is within the abilities of a person skilled in the art to replace the exemplary compounds shown in the schemes and exemplary reagent given in the text by appropriate alternative compounds or reagents or to omit or add synthetic steps when appropriate.

The synthesis of a cycloalkyl aminoalcohol (iii) is described exemplary in schemes 2 and 3 but does not limit the scope of substituents in the present invention. A cycloalkyl amine moiety (iii) with a secondary or tertiary amine subunit can for example be accessed starting from a suitably substituted cycloalkylnitrile (vi), which can be substituted with functionalities as alkyl, alkoxy, or acetals. To introduce an residue $R_{10}$, if wanted, the nitrile can get functionalized in alpha-position by reaction with suitable electrophiles like described in the literature (Organic Process Research & Development, 5(6), 587-592; 2001), using for example a suitable fluorinated aryl compound and a suitable base like KHMDS, LiHMDS or sodium hydride in an inert solvent like toluene. Alternatively, a suitable nucleophile like aryl lithium reagents can be reacted with a suitable ketone (xvi) to give the corresponding alcohol, which can be converted into the corresponding nitrile (vii) by treatment with reagents like TMSCN.

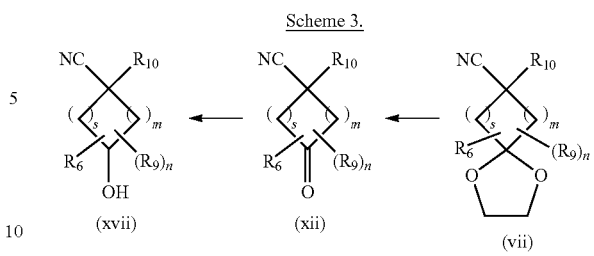

Scheme 3.

The functionalized nitrile (vii or xvii) can then for example be directly reacted with suitable nucleophiles for the intro-

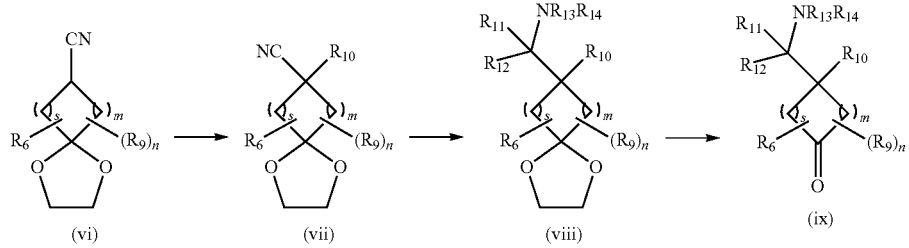

Scheme 2

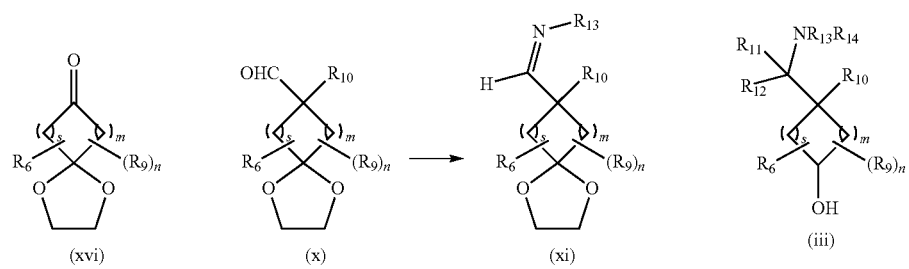

Another option is construction of the cycloalkyl moiety for example by Dieckmann condensations like described in the literature (Lednicer et al, J. Med. Chem. 1980, 23(4), 424-30; DeGraffenreid et al., J. Org. Chem. 2007, 72(19), 7455-7458) to give ketones like (xii), that can be converted into their acetals (vii) by treatment with diols like ethylene diol, or can be directely converted into the corresponding alcohols using suitable reductive agents like sodium borohydride in a suitable solvent like methanol, ethanol or THF. The obtained nitrile can then be for example further converted as described in schemes 2 and 4.

duction of functional groups $R_{11}$ and $R_{12}$, for example lithium organyls or Grignard reagents to give compounds like (viii or iii). A suitable N-protecting group like t-butyloxycarbonyl or benzyloxycarbonyl may or may not be attached after this step depending on the nature of the starting nitrile and the complexity of the reactions to follow. For $R_{11}=R_{12}$, lithium organyls can be used as nucleophiles activated by addition of lewis acids like titanium isopropoxylate and cerium chloride.

For $R_{11}$ is H, the intermediate imine formed on addition of the nucleophiles can be isolated and reduced by suitable reductive agents like cyanoborohydrides or borohydrides in solvents such as tetrahydrofuran or alcohols. Alternatively, the nitrile (vii) can be reduced to the aldehyde (x) by suitable hydride donor reagents like diisobutylaluminiumhydride in cold organic solvents such as diethylether or toluene and converted to appropriate imines (xi) like benzylimines or N-tert-butanesulfinyl imines via a lewis acid catalysed reaction with suitably functionalized amines. These imines (xi) can then be reacted with suitable nucleophilic reagents like lithium organyls, Grignard reagents or trimethylsilanes in combination with tetraalkyl fluorides to introduce a variety of substituents like alkyl, cycloalkyl or heterocyclyl groups. The keto functionality can then be liberated by methods known to the person skilled in art, for example by treatment with aqueous acids like acetic acid or hydrochloric acid in acetone mixtures, and subsequently reduced to the corresponding alcohols (iii), generally as cis/trans mixtures, by suitable reducing agents like borohydrides in alcohols, tetrahydrofuran or toluene at deep temperatures.

This liberation, however, can also be performed after the nitrile functionalization step (Scheme 4), depending on the nature of the used nitrile and the substitution pattern. If the ketone is reduced before the nitrile gets functionalized, generally only one isomer (cis or trans) is obtained in high selectivity. For the conversion of nitriles from type (xiii) to the amines (iii) the use of a suitable protecting group on the alcohol functionality may prove beneficial. Suitable protecting groups are known to the person skilled in art and may be ethers, like tetrahydropyrane, methoxymethyl or silyl ethers.

Scheme 4

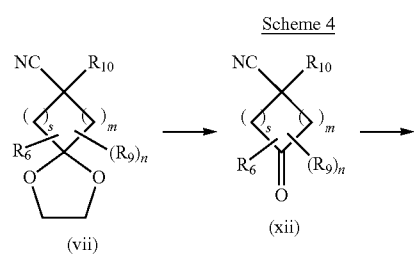

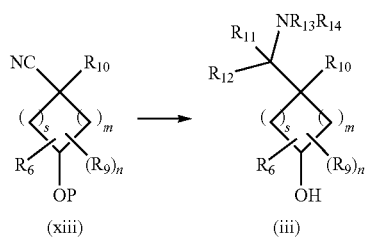

To obtain cycloalkyl amino moieties other than cycloalkyl aminoalcohols, various methods can be applied. The following general scheme (scheme 4) illustrates some of the possible ways to access these amines, but does not limit the present invention.

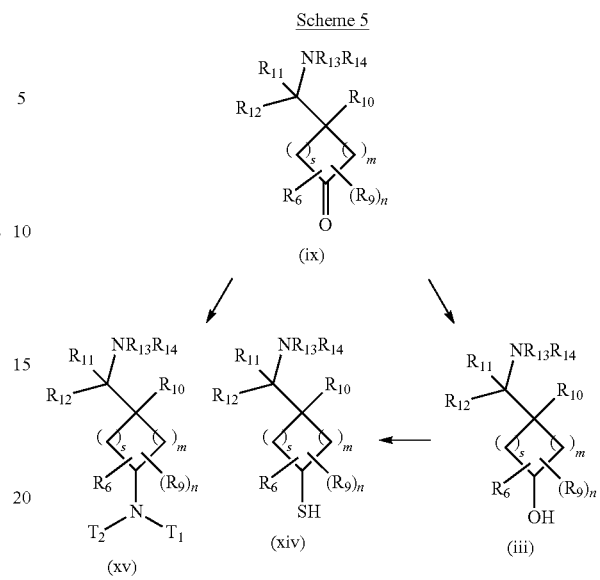

For instance, the hydroxy functionality of a compound (iii) can be converted to a thiol via a Mitsunobu reaction using thioacetate and subsequent basic cleavage with a suitable base, leading to amino moieties of type (xiv). These thiols can—after coupling to suitable isoquinolinones under useful reaction conditions like for example in a similar fashion as described above in scheme 1 for the coupling of (iii)—then be used to obtain compounds of formula (I) with the linker unit L=S—or optionally be oxidized via methods known to the person skilled in the art to the corresponding sulfoxides and sulfones (for obtaining compounds of formula (I) with the linker unit L=SO and $SO_2$). The corresponding amines can be accessed via a reductive amination step starting from ketones such as compound (ix or xii) using suitable amines in the presence of a reducing agent like sodium triacetoxy borohydride, sodium borohydride or sodium cyanoborohydride in the presence of a water withdrawing agent like molecular sieves or a suitable ortho ester.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a pharmaceutically acceptable salt or a prodrug of a compound of the formula (I) can then be carried out by known processes.

In general, a reaction mixture containing a final compound of the formula (I) or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

EXAMPLES

The following examples illustrate the various embodiments of the present invention and are part of the present invention.

Cis and trans nomenclature in the title of the respective compounds refer to the relative configuration of the —[CR$_{11}$R$_{12}$]$_r$NR$_{13}$R$_{14}$ residue and the L-residue at the cycloalkyl ring. This convention is maintained for the respective precursors.

cis-4-Hydroxy-1-phenylcyclohexanecarbonitrile (1)

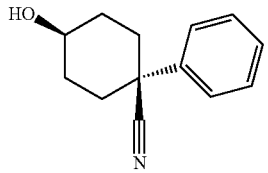 [SMILES: N#C[C@]1(c2ccccc2)CC[C@H](O)CC1]

To a suspension of 4-cyano-4-phenylcyclohexanone (25 g, 125 mmol) in absolute ethanol (1 L) was added sodium borohydride (9.5 g, 251 mmol) portionwise over 30 minutes. The resulting mixture was stirred at room temperature for 2 hours, ice was then added and the crude mixture stirred for another hour. Ethanol was evaporated under reduced pressure, and the resulting aqueous layer was extracted with dichloromethane. The organic layer was dried over sodium sulphate, filtered and concentrated under reduced pressure. The crude product cis-4-hydroxy-1-phenylcyclohexanecarbonitrile (25 g, containing approx. 10% of the trans isomer) was used in the next step without any further purification. R$_t$=3.99 min (Method 8). Detected mass: 202 (M+H$^+$).

cis-4-Cyano-4-phenylcyclohexyl acetate (2)

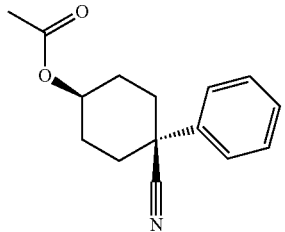 [SMILES: CC(=O)O[C@H]1CC[C@](C#N)(c2ccccc2)CC1]

To a solution of cis-4-hydroxy-1-phenylcyclohexanecarbonitrile (1, 0.2 g, 1 mmol) in anhydrous pyridine (10 mL) were added acetic anhydride (0.1 mL, 1.2 mmol) and 4-dimethylaminopyridine (0.024 g, 0.2 mmol). The reaction mixture was stirred at room temperature for 12 hours, and then evaporated to dryness. A saturated aqueous solution of sodium bicarbonate was added to the crude product and the mixture was extracted with dichloromethane. The organic layer was dried over sodium sulphate, filtered and evaporated to dryness. The crude product was purified by silica gel chromatography (eluting with 0 to 40% ethyl acetate in cyclohexane) to give 3.39 g of cis-4-cyano-4-phenylcyclohexyl acetate (containing approx. 10% of trans isomer). R$_t$=7.34 min (Method 9). Detected mass: 266 (M+Na$^+$).

cis-4-(1-Aminocyclopropyl)-4-phenylcyclohexyl acetate (3)

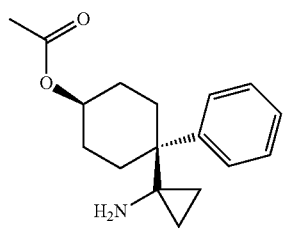 [SMILES: CC(=O)O[C@H]1CC[C@@](c2ccccc2)(C2(N)CC2)CC1]

A 250-mL three necked round bottom flask equipped with a temperature probe and an argon line was charged with cis-4-cyano-4-phenylcyclohexyl acetate (2, 3.39 g, 13.9 mmol) and anhydrous tetrahydrofuran (140 mL). The resulting solution was cooled to −75° C. and titanium (IV) isopropoxide (4.5 mL, 15.3 mmol) was added dropwise while the reaction temperature remained below −70° C. Once the addition was completed, ethylmagnesium bromide (3M in diethyl ether) (10.2 mL, 30.6 mmol) was added dropwise. The mixture was stirred at −70° C. for 10 minutes and then allowed to slowly warm to room temperature, while stirring was continued for another 30 minutes. At this stage, boron trifluoride etherate (3.5 mL, 28 mmol) was added, and stirring was continued for 1 hour. Water (14 mL) was added, followed by 10% aqueous HCl (140 mL) and diethyl ether (100 mL). A 10% aq. NaOH solution was added to the resulting clear mixture until the pH became basic. The product was extracted with diethyl ether. The combined organic extracts were dried over anhydrous sodium sulphate. After evaporation of the solvent, the product was purified by flash chromatography on silica gel (eluting with 0 to 100% ethyl acetate in cyclohexane) to yield 0.65 g of cis-4-(1-aminocyclopropyl)-4-phenylcyclohexyl acetate. R$_t$=2.72 min (Method 7). Detected mass: 274 (M+H$^+$).

cis-4-(1-Aminocyclopropyl)-4-phenylcyclohexanol (4)

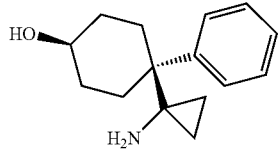

To a solution of cis-4-(1-aminocyclopropyl)-4-phenylcyclohexyl acetate (3, 0.54 g, 2 mmol) in anhydrous methanol (20 mL) was added sodium methoxide (0.5 N in methanol) (8.7 mL, 4.3 mmol). After stirring for 72 hours at room temperature, the reaction mixture was cooled to 0° C., a 1M solution of hydrochloric acid in diethyl ether (10 mL) was added, and the resulting white precipitate was filtered off. The filtrate was concentrated under reduced pressure, and the resulting crude product was triturated with a methanol/diethyl ether mixture. The beige solid was isolated by filtration to give 400 mg of cis-4-(1-aminocyclopropyl)-4-phenylcyclohexanol as the hydrochloride. $R_t$=2.33 min (Method 8). Detected mass: 232 (M+H$^+$).

cis-4-(1-Aminocyclopropyl)-4-(2-fluorophenyl)cyclohexanol (5)

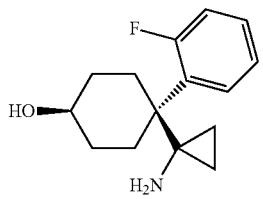 [SMILES: NC1([C@]2(c3ccccc3F)CC[C@H](O)CC2)CC1]

Utilizing the procedures described for the synthesis of 4, 0.219 g of cis-4-(1-aminocyclopropyl)-4-(2-fluorophenyl) cyclohexanol (5) was obtained as the hydrochloride (contaminated with 4% of trans isomer) starting from 4-cyano-4-(2-fluorophenyl)cyclohexanone. $R_t$=0.66 min (Method 7). Detected mass: 250 (M+H$^+$).

cis-4-(1-Aminopropyl)-4-phenylcyclohexanol (6)

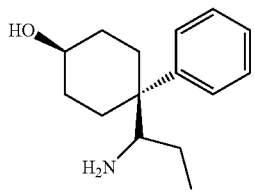 [SMILES: CCC(N)[C@]1(c2ccccc2)CC[C@H](O)CC1]

To a solution of cis-4-hydroxy-1-phenylcyclohexanecarbonitrile (1, 1.0 g, 4.97 mmol) in anhydrous toluene (100 mL) was added dropwise a solution of ethylmagnesium bromide (3M in diethyl ether, 10 mL, 30 mmol). The reaction mixture was refluxed overnight, then poured onto ice. The resulting mixture was extracted with diethyl ether, the organic layer was dried over sodium sulphate, filtered and concentrated under reduced pressure. To a solution of this crude product in absolute ethanol (100 mL) was added sodium borohydride (0.257 g, 7.5 mmol). The reaction mixture was stirred at room temperature for 2 hours, aqueous 1N HCl was then added until pH=1.3. Ethanol was evaporated under reduced pressure, the resulting aqueous phase was washed with diethyl ether, then neutralized with a saturated aqueous sodium bicarbonate solution and eventually extracted with diethyl ether and chloroform, subsequently. The combined organic layers were dried over anhydrous sodium sulphate, filtered and evaporated to dryness. The crude product was dissolved in 15 mL of methanol and HCl (4N in dioxane) (0.9 mL) was added dropwise. The suspension was stirred for 30 min, then evaporated to dryness to yield 0.858 g of cis-4-(1-aminopropyl)-4-phenylcyclohexanol (6) as the hydrochloride (contaminated with 10% of trans isomer). $R_t$=2.59 min (Method 8). Detected mass: 234 (M+H$^+$).

cis-4-(Methoxymethoxy)-1-phenylcyclohexanecarbonitrile (7)

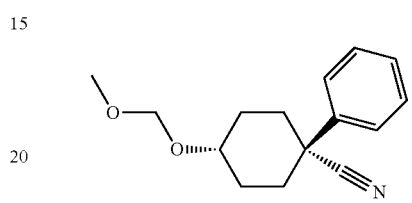

A stirred solution of potassium tert-butoxide (1.6 M in tert-butanol, 37.3 mL, 37.3 mmol) was cooled to 0° C. and anhydrous DMF (6 mL) was added before the mixture began to freeze. A solution of cis-4-hydroxy-1-phenylcyclohexanecarbonitrile (1, 3 g, 14.9 mmol) in anhydrous DMF (30 mL) was added to the reaction mixture. A solution of chloromethyl methyl ether (2.83 mL, 37.3 mmol) was then added dropwise at 2-4° C. and the mixture was gradually allowed to warm to room temperature while stirring was continued overnight. The mixture was poured onto cold aqueous sodium bicarbonate solution, then extracted with diethyl ether. The organic layer was dried over sodium sulphate and evaporated. The crude product was purified by chromatography on silica gel to yield 2.2 g of the title compound. $R_t$=7.01 min (Method 9). Detected mass: 246 (M+H$^+$)

cis-4-(1-Amino-1-methylethyl)-4-phenylcyclohexanol (8)

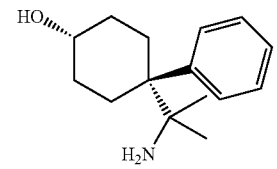 [SMILES: CC(C)(N)[C@]1(c2ccccc2)CC[C@H](O)CC1]

A suspension of commercial anhydrous cerium chloride (Alfa Aesar, 2 g, 8.15 mmol) in anhydrous THF (12 mL) was heated to 45° C. for 3 h under vigourous stirring. The slurry was cooled to room temperature and treated with cis-4-(methoxymethoxy)-1-phenylcyclohexanecarbonitrile (7, 1 g, 4.08 mmol). After cooling to −10° C., a 1.5 M solution of MeLi.LiBr (6.79 mL, 10.2 mmol) in diethyl ether was added dropwise over 20 minutes, then the resulting brown slurry was stirred for an additional 20 min. The reaction was quenched by addition of concentrated NH$_4$OH (2.6 mL) over 10 min. The yellow suspension obtained was allowed to warm to room temperature, stirred for 30 min, diluted with THF and then filtered. The wet cake was rinsed several times with THF. The combined filtrates were then concentrated to almost dryness, diluted with dichloromethane and washed with 0.1 N NaOH. The organic layer was dried with sodium sulphate and evaporated.

The crude mixture was suspended in a mixture of methanol (20 mL) and aqueous 2N HCl (20 mL) then stirred overnight at room temperature. After evaporation of methanol and filtration, the filtrate was concentrated to dryness to yield 0.38 g of a crude mixture of the title compound (8). $R_t$=2.43 min (Method 9). Detected mass: 234 (M+H$^+$).

6,7-difluoro-5-methyl-isoquinoline (43)

a) [1-(3,4-Difluoro-2-methylphenyl)-methylidene]-2,2-dimethoxyamine (40)

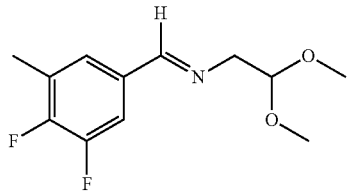

3,4-difluoro-2-methylbenzaldehyde (26 g, 166 mmol) was dissolved in toluene (182 mL) and reacted with 2-aminoacetaldehyde dimethylacetal (19.3 g, 183 mmol) and toluene sulphonic acid (3.2 g) for 2 hours in a Dean-Stark apparatus. The solution was allowed to cool down, extracted with saturated sodium bicarbonate solution, water and brine, dried over sodium sulphate and evaporated to dryness to give 40.4 g of a dark yellow oil which was used without further purification.

b) 3,4-Difluoro-2-methylbenzyl-2,2-dimethoxyethylamine (41)

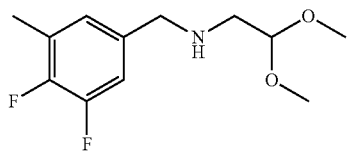

[1-(3,4-Difluoro-2-methylphenyl)-methylidene]-2,2-dimethoxyamine (40, 40.4 g) was dissolved in ethanol (225 mL). Sodium borohydride (4.8 g, 124 mmol) was added portionwise. Stirring was continued overnight. For workup, acetic acid was added until no gas evolution could be observed. Then the solution was evaporated to dryness, taken up in dichloromethane and washed with saturated sodium bicarbonate solution and twice with water. The organic layer was washed with brine, dried over magnesium sulphate and evaporated to dryness. The crude product obtained (37.8 g) was used without purification.

c) N-(3,4-Difluoro-2-methylbenzyl)-N-(2,2-dimethoxyethyl)-4-methylphenyl-sulphonylamine (42)

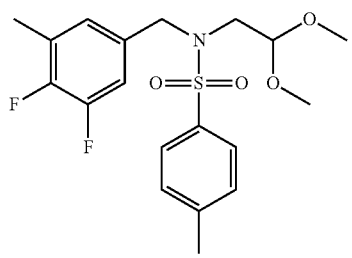

3,4-Difluoro-2-methylbenzyl-2,2-dimethoxyethylamine (41, 37.8 g) was dissolved in dichloromethane (100 mL). Pyridine (42 mL) was added. At 0° C. a solution of p-toluenesulphonyl chloride (36.8 g, 193 mmol) in dichloromethane was added dropwise. The reaction was allowed to warm to room temperature and stirring continued until conversion was complete. For workup, the reaction mixture was diluted with dichloromethane (100 mL) and extracted twice with 1.5M hydrochloric acid, twice with sodium bicarbonate solution and once with brine. The organic layer was dried over magnesium sulphate, evaporated to dryness to give crude product as an orange oil (68.3 g). This was used without further purification.

d) 6,7-difluoro-5-methyl-isoquinoline (43)

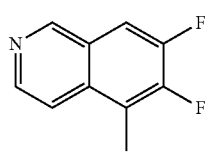

Aluminium trichloride (112 g, 838 mmol) was suspended in dichloromethane (250 mL) at 0° C. A solution of N-(3,4-difluoro-2-methylbenzyl)-N-(2,2-dimethoxyethyl)-4-methylphenyl-sulphonylamine (42, 68.3 g) in dichloromethane (250 mL) was added. The reaction mixture was heated at 50° C. for 2 hours, before being cooled to 0° C. and poured on ice. The organic layer was separated, and the aqueous layer extracted twice more with dichloromethane/isopropanol (3:1). The combined organic phase was extracted twice with saturated sodium bicarbonate solution and dried over magnesium sulphate, before filtration and evaporation gave 63.5 g of crude dark brown semi-solid product. This was purified by chromatography on silica gel. Elution with ethyl acetate/heptane (5%:95% to 35%:65%) gave 11.3 g of the title compound 43 as a tan-coloured solid. $R_t$=0.86 min (Method 10). Detected mass: 180.1 (M+H$^+$).

The Isoquinolines in the following table were obtained by following a similar reaction sequence as used for synthesis of 43.

| Comp. No. | Starting compound | Product | Chemical Name | [M + H⁺] | $R_t$ [min] | Method |
|---|---|---|---|---|---|---|
| 44 | 3,5-dimethyl-4-fluoro-benzaldehyde | | 5,7-dimethyl-6-fluoro-isoquinoline | 176.1 | 1.06 | 10 |
| 45 | 3,4-difluoro-benzaldehyde | | 6,7-difluoro-isoquinoline | 166.1 | 1.07 | 2 |
| 46 | 3-bromo-4-fluoro-benzaldehyde | | 7-bromo-6-fluoro-isoquinoline | 226.0 228.3 | 0.91 | 4 |
| 47 | 4-fluoro-3-methoxy-benzaldehyde | | 6-fluoro-7-methoxy-isoquinoline | 178.1 | 0.90 | 10 |
| 48 | 4-fluoro-3-methyl-benzaldehyde | | 6-fluoro-7-methyl-isoquinoline | 161.9 | 0.90 | 10 |

7-Chloro-6-fluoro-isoquinoline 2-oxide (9)

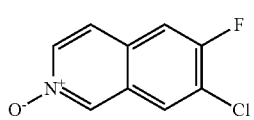

50 g of 7-chloro-6-fluoro-isoquinoline (prepared according to WO 2007/012422) were dissolved in dichloromethane and cooled to 5° C. 69.6 g of m-chloro-perbenzoic acid (70%) were added portionwise. The mixture was stirred at room temperature. When conversion was complete, the mixture was diluted with 1.5 L of dichloromethane and washed three times with saturated sodium bicarbonate solution. The organic layer was dried over sodium sulphate and evaporated to dryness to give 47.6 g of the desired product 9. $R_t$=0.98 min (Method 5). Detected mass: 198.1 (M+H⁺).

7-Chloro-6-fluoro-1-methoxy-isoquinoline (10)

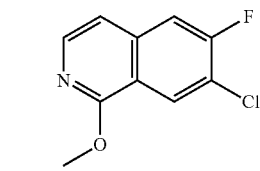

10 g of 7-Chloro-6-fluoro-isoquinoline 2-oxide (9) were dissolved in 100 mL of dry methanol. 12 mL of ethyl chloroformate were added dropwise at −10° C. The mixture was allowed to stir for 15 minutes and then 28 mL of triethylamine, dissolved in 55 mL of methanol, were added dropwise at −20° C. over 1 h.

100 mL of 2N aqueous sodium hydroxide solution were added and the formed precipitate was filtered. Additional product was precipitated by addition of 2N sodium hydroxide solution and water to the mother liquor. The combined solids were dried to give 7.8 g of the desired product (10). $R_t$=3.75 min (Method 1). Detected mass: 212.0 (M+H$^+$).

The following compounds were obtained in a similar fashion as described for the synthesis of 10, starting from the respective isoquinolines.

| Comp. No. | Starting compound | Product | Chemical Name | [M + H$^+$] | $R_t$/ [min] | Method |
|---|---|---|---|---|---|---|
| 49 | 5-Chloro-6-fluoro-isoquinoline | | 5-Chloro-6-fluoro-1-methoxy-iso-quinoline | 212.0 | 1.78 | 10 |
| 50 | 45 | | 6,7-difluoro-1-methoxy-iso-quinoline | 196.1 | 3.53 | 1 |
| 51 | 43 | | 6,7-Difluoro-1-methoxy-5-methyl-isoquinoline | 210.1 | 3.85 | 2 |
| 52 | 48 | | 6-fluoro-1-methoxy-7-methyl-iso-quinoline | 192.1 | 3.44 | 2 |
| 53 | 44 | | 6-Fluoro-1-methoxy-5,7-dimethyl-iso quinoline | 206.1 | 3.74 | 2 |
| 54 | 47 | | 6-Fluoro-1,7-dimethoxy-isoquinoline | 208.1 | 3.1 | 2 |

1-Benzyloxy-7-chloro-6-fluoro-isoquinoline (38)

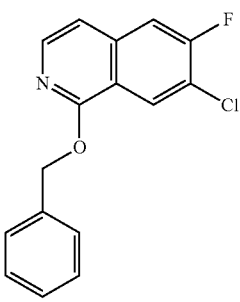 [SMILES: Fc1cc2ccnc(OCc3ccccc3)c2cc1Cl]

7-Chloro-6-fluoro-2H-isoquinolin-1-one (prepared according to WO 2007/012422; 52.2 g) was dissolved in THF (1 L). After addition of silver carbonate (145.5 g) and benzyl bromide (40.6 mL), the mixture was stirred at room temperature overnight. Another 6.2 mL of benzyl bromide were added and the mixture was stirred at 70° C. for 2 h. After cooling down to room temperature, the reaction mixture was diluted by addition of 1 L of ethyl acetate and filtered over celite. The filter cake was washed thoroughly, the organic layer was evaporated and subjected to silica gel chromatography (n-heptanes: methyl tert. butyl ether) to give 27.8 g of the title compound (38). $R_t$=3.73 min (Method 1). Detected mass: 288.1 (M+H$^+$).

1-Benzyloxy-4-benzyl-7-chloro-6-fluoro-isoquinoline (55)

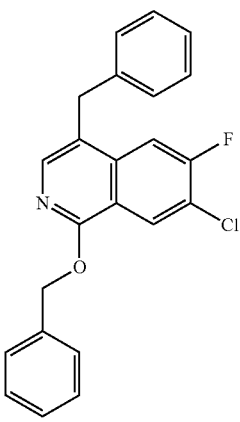 [SMILES: Fc1cc2c(Cc3ccccc3)cnc(OCc3ccccc3)c2cc1Cl]

As a side product of the preparation of 1-benzyloxy-7-chloro-6-fluoro-isoquinoline (38), 8.45 g of 1-benzyloxy-4-benzyl-7-chloro-6-fluoro-isoquinoline (55) could be isolated by silica gel chromatography. $R_t$=4.04 min (Method 1). Detected mass: 378.1 (M+H$^+$).

1-Benzyloxy-7-methyl-6-fluoro-isoquinoline (39)

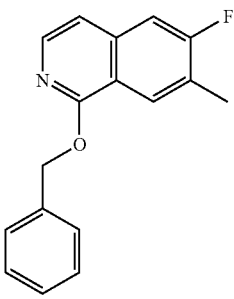 [SMILES: Cc1cc2c(OCc3ccccc3)nccc2cc1F]

1-Benzyloxy-7-methyl-6-fluoro-isoquinoline (39) has been prepared according to the procedure described for the synthesis of (38) starting from 7-methyl-6-fluoro-2H-isoquinolin-1-one (prepared according to the protocol described in WO 2007/012421 or WO 2007/012422). $R_t$=4.00 min (Method 1). Detected mass: 268.1 (M+H$^+$).

1-(4-Fluoro-phenyl)-4-oxo-cyclohexanecarbonitrile (12)

a) 5-Cyano-5-(4-fluoro-phenyl)-2-oxo-cyclohexanecarboxylic acid methyl ester (11)

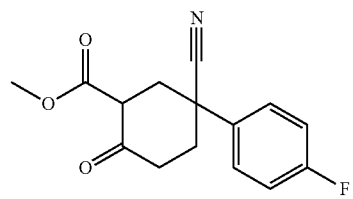 [SMILES: COC(=O)C1CC(C#N)(c2ccc(F)cc2)CCC1=O]

70 mL of methylacrylate and 50 g of 4-fluorophenylacetonitrile were dissolved in a mixture of 200 mL of THF and 50 mL of dry methanol. 150 mL of sodium methylate (30% in methanol) were added dropwise, while temperature was maintained below 40° C. The mixture was stirred at room temperature for 15 h and heated for another 4 h at 50° C. When the reaction was complete, the mixture was allowed to cool to room temperature and poured onto a cold 2N aqueous hydrochloric acid solution. The aqueous layer was extracted three times with ethyl acetate and the combined organic layer was washed with water and brine, dried over magnesium sulphate and evaporated to give 101.5 g of the desired product. $R_t$=1.59 min (Method 5). Detected mass: 276.2 (M+H$^+$).

b) 1-(4-Fluoro-phenyl)-4-oxo-cyclohexanecarbonitrile (12)

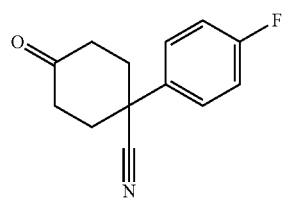 [SMILES: N#CC1(c2ccc(F)cc2)CCC(=O)CC1]

101.5 g of 5-Cyano-5-(4-fluoro-phenyl)-2-oxo-cyclohexanecarboxylic acid methyl ester (11) were dissolved in 680 mL of ethanol and 171 mL of concentrated aqueous hydrochloric acid were added. The mixture was heated to reflux for 40 h, then evaporated. The residue was taken up in water and extracted with dichloromethane. The organic layer was washed with brine, dried over magnesium sulphate and evaporated to give 95.2 g of crude product, that was purified by silica gel filtration (heptanes:ethyl acetate) to yield 50.4 g of the desired product 12. $R_t$=1.26 min (Method 1). Detected mass: 218.2 (M+H$^+$).

1-(4-Methoxy-phenyl)-4-oxo-cyclohexanecarbonitrile (56)

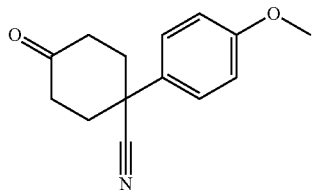 [SMILES: COc1ccc(C2(C#N)CCC(=O)CC2)cc1]

56 was obtained from methylacrylate and 4-methoxyphenylacetonitrile in a similar fashion as described for synthesis of (12). $R_t$=4.24 min (Method 3). Detected mass: 230.1 (M+H$^+$).

1-Cyano-1-(3-fluorophenyl)cyclohexan-4-one (58)

a) 1-Cyano-1-(3-fluorophenyl)-3-methoxycarbonyl-cyclohexan-4-one (57)

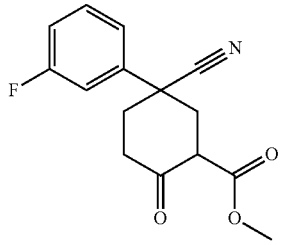 [SMILES: COC(=O)C1CC(C#N)(c2cccc(F)c2)CCC1=O]

Potassium t-butoxide (62.3 g, 555 mmol) was added dropwise to a solution of 3-fluorophenylacetonitrile (56, 25 g, 185 mmol) in THF (500 mL). The reaction mixture was stirred overnight. The reaction mixture was acidified with hydrochloric acid (3M) and extracted with dichloromethane. The organic extracts were evaporated to yield 57.2 g of an orange oil. $R_t$=3.39 min (Method 3). Detected mass: 275.1 (M+H$^+$).

b) 1-Cyano-1-(3-fluorophenyl)cyclohexan-4-one (58)

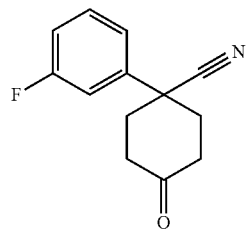 [SMILES: N#CC1(c2cccc(F)c2)CCC(=O)CC1]

A mixture of 1-cyano-1-(3-fluorophenyl)-3-methoxycarbonylcyclohexan-4-one (57, 51 g, 185 mmol), water (54.8 mL) and DMSO (840 mL) was heated and stirred at 150° C. for 3 hours, followed by stirring at room temperature overnight. The reaction mixture was evaporated and purified by chromatography on silica gel. Elution with ethyl acetate/heptane (5%:95% to 30%:70%) gave 28 g of desired material as a solid product. $R_t$=3.89 min (Method 3). Detected mass: 218.2 (M+H$^+$).

The following cyclohexanones were prepared using the same procedure as described for 58, starting from the respective phenylacetonitrils.

| Comp. No. | Starting compound | Product | Chemical Name | [M + H$^+$] | $R_t$/[min] | Method |
|---|---|---|---|---|---|---|
| 59 | 4-bromo-phenyl acetonitrile | 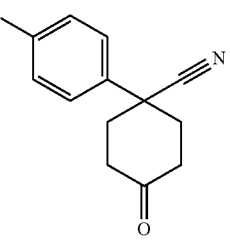 | 1-cyano-1-(4-bromophenyl)cyclo-hexan-4-one | 277.9 | 4.79 | 3 |
| 60 | 2-chloro-phenyl acetonitrile | 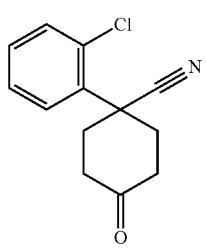 [SMILES: N#CC1(c2ccccc2F)CCC(=O)CC1] | 1-cyano-1-(2-chlorophenyl)cyclo-hexan-4-one | 275.2 (M + CH$_3$CN + H$^+$) | 1.87 | 4 |

| Comp. No. | Starting compound | Product | Chemical Name | [M + H⁺] | R$_t$/ [min] | Method |
|---|---|---|---|---|---|---|
| 61 | 3-methoxy-phenyl acetonitrile | | 1-cyano-1-(3-methoxyphenyl)cyclo-hexan-4-one | 229.1 | 4.31 | 6 |
| 62 | 4-isopropyl-phenyl acetonitrile | | 1-cyano-1-(4-isopropylphenyl)cyclo-hexan-4-one | 285.3 (M + CH$_3$CN + H⁺) | 2.23 | 4 |
| 63 | 2-methoxy-phenyl acetonitrile | | 1-cyano-1-(2-methoxyphenyl)cyclo-hexan-4-one | 230.2 | 3.81 | 6 |
| 64 | 2-fluoro-phenyl acetonitrile | | 1-cyano-1-(2-fluorophenyl)cyclohexan-4-one | 259.3 (M + CH$_3$CN + H⁺) | 1.79 | 4 |

1-Cyano-1-(2,4-difluorophenyl)cyclohexanone (65)

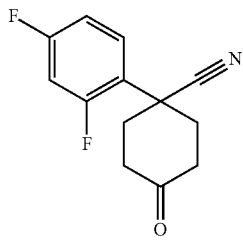 [SMILES: N#CC1(c2ccc(F)cc2F)CCC(=O)CC1]

Potassium t-butoxide (55 g, 489 mmol) was added to a stirred solution of 2,4-difluorophenylacetonitrile (25 g, 163 mmol) and methyl acrylate (28.1 g, 29.4 mL, 326 mmol) in THF (475 mL) at room temperature. After one hour stirring, water (2.4 L) was added and the mixture stirred for 2 hours at 68° C. After cooling the mixture was extracted with methyl tert butyl ether. After drying over sodium sulphate the organic phase was evaporated to give 34.7 g of an orange oil which was purified by chromatography on silica gel. Elution with ethyl acetate/heptane (5%:95% to 35%:65%) gave the desired product after evaporation as 19 g of a colourless crystalline solid. R$_t$=3.84 min (Method 3). Detected mass: 236.3 (M+H⁺).

The following cyclohexanones were prepared using the same procedure as described for 65, starting from the respective phenylacetonitrils:

| Comp. No. | Starting compound | Product | Chemical Name | [M + H⁺] | $R_t$ [min] | Method |
|---|---|---|---|---|---|---|
| 66 | 3-bromo-phenyl acetonitrile | | 1-cyano-1-(3-bromophenyl) cyclohexan-4-one | 278.1 | 4.26 | 18 |
| 67 | 2-bromo-phenyl acetonitrile | | 1-cyano-1-(2-bromophenyl) cyclohexan-4-one | 302.2 (M + Na⁺) | 4.45 | 6 |
| 68 | Pyrid-2-yl acetonitrile | | 1-cyano-1-(pyrid-2-yl) cyclohexan-4-one | 201.1 | 1.75 | 1 |
| 69 | 4-fluor-2-methylphenyl acetonitrile | | 1-cyano-1-(4-fluoro-2-methylphenyl) cyclohexan-4-one | 232.3 | 4.02 | 6 |
| 70 | 3,5-difluoro-phenyl acetonitrile | | 1-cyano-1-(3,5-difluorophenyl) cyclohexan-4-one | 236.1 | 4.02 | 6 |
| 71 | 3,4-difluoro-phenyl acetonitrile | | 1-cyano-1-(3,4-difluorophenyl) cyclohexan-4-one | 236.2 | 3.98 | 6 |

-continued

| Comp. No. | Starting compound | Product | Chemical Name | [M + H+] | $R_t$/[min] | Method |
|---|---|---|---|---|---|---|
| 72 | 2-methyl phenyl acetonitrile | | 1-cyano-1-(2-methylphenyl)cyclohexan-4-one | 214.3 | 3.92 | 6 |
| 73 | 2-trifluoro methoxy phenyl acetonitrile | | 1-cyano-1-(2-trifluoromethoxy-phenyl)cyclo-hexan-4-one | 284.1 | 2.26 | 20 |
| 74 | 4-fluoro-3-methoxy phenyl acetonitrile | | 1-cyano-1-(4-fluoro-3-methoxy-phenyl)cyclohexan-4-one | 248.2 | 3.89 | 6 |
| 75 | 3-ethoxy phenyl acetonitrile | | 1-cyano-1-(3-ethoxyphenyl)cyclohexan-4-one | 244.3 | 4.19 | 6 |
| 76 | 3-methoxy-4-methylphenyl acetonitrile | | 1-cyano-1-(3-methoxy-4-methylphenyl)cyclohexan-4-one | 244.0 | 4.53 | 6 |

| Comp. No. | Starting compound | Product | Chemical Name | [M + H⁺] | $R_t$/ [min] | Method |
|---|---|---|---|---|---|---|
| 77 | 4-trifluoro methoxy phenyl acetonitrile | 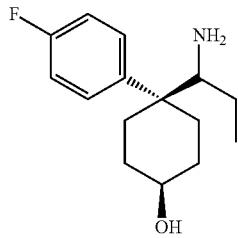 | 1-cyano-1-(4-trifluoromethoxy-phenyl)cyclohexan-4-one | 284.2 | 4.36 | 6 | cis-4-Hydroxy-1-(4-fluoro-phenyl)cyclohexanecarbonitrile (13)

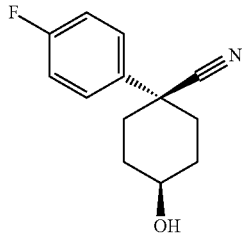 [SMILES: N#C[C@]1(c2ccc(F)cc2)CC[C@H](O)CC1]

20 g of 1-(4-Fluoro-phenyl)-4-oxo-cyclohexanecarbonitrile (12) were dissolved in 300 mL of dry ethanol and cooled to −20° C. 3.83 g of sodium borohydride were added and the mixture was allowed to slowly warm to room temperature. When conversion was complete, 150 mL of water were added and the pH was adjusted to 2 by addition of 2N hydrochloric acid. The mixture was extracted with ethyl acetate three times and the combined organic layer was extracted with brine, dried over magnesium suphate and evaporated to dryness. The resulting residue was crystallized from n-heptanes:ethyl acetate to give 11.9 g of the desired product. $R_t$=2.78 min (Method 1). Detected mass: 220.1 (M+H⁺).

cis-4-(tert-Butyl-dimethyl-silanyloxy)-1-(4-fluoro-phenyl)-cyclohexane-carbonitrile (78)

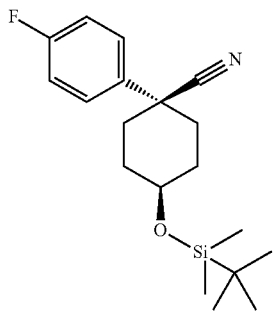 [SMILES: CC(C)(C)[Si](C)(C)O[C@H]1CC[C@](C#N)(c2ccc(F)cc2)CC1]

30 g of cis-4-Hydroxy-1-(4-fluoro-phenyl)-cyclohexanecarbonitrile (13) were dissolved in 350 mL of dry dichloromethane. 39.8 mL of 2,6-lutidine were added and the mixture was cooled to 0° C. 37.7 mL of tert.-butyldimethylsilyl trifluoromethansulfonate were added and the mixture was stirred at room temperature overnight. The reaction mixture was diluted with dichloromethane, extracted twice with water, 0.1N hydrochloric acid and once with saturated sodium bicarbonate and brine, dried over magnesium sulphate, evaporated to dryness and purified by silica gel chromatography to give 43.8 g of the desired product. $R_t$=3.21 min (Method 12). Detected mass: 334.2 (M+H⁺).

cis-4-(1-amino-propyl)-4-(4-fluoro-phenyl)cyclohexanol (14)

Under argon, 2 g of cis-4-hydroxy-1-(4-fluoro-phenyl)cyclohexanecarbonitrile (13) were dissolved with cooling in a 1M solution of ethyl magnesium bromide in THF (or diethyl ether, alternatively). The reaction mixture was refluxed for 14 h, cooled to room temperature and diluted with 600 mL of THF. The mixture was quenched by addition of a minimal amount of methanol, filtered over celite and evaporated to dryness. The resulting foam was dissolved in 300 mL of ethanol and 690 mg of sodium borohydride were added portionwise under cooling. The mixture was allowed to stir until the reaction was complete, evaporated to dryness and the resulting residue was partitioned between 1N aqueous HCl and ethyl acetate. The organic layer was extracted once with 1N HCl and the combined aqueous layers were washed with ethyl acetate and subsequently adjusted to pH 12 by addition of 5N sodium hydroxide solution. The aqueous layer was extracted twice with dichloromethane, the combined dichloromethane layers were washed with brine, dried over sodium sulphate and evaporated to give 1.72 g of the desired product. $R_t$=2.25 min (Method 1). Detected mass: 252.2 (M+H⁺).

Alternatively, 14 can be obtained employing 78 in a similar reaction:

18.3 g of 78 were dissolved in 183 mL of dry toluene and 36.6 mL of a solution of ethyl magnesium bromide (3M in diethylether) were added. The mixture was stirred at 80° C. for 16 h, diluted with THF, cooled to 5° C. and quenched by addition of a few mL of ethanol. The mixture was filtered over celite, the solution evaporated to dryness and the residue was taken up in 100 mL of ethanol. 4.15 g of sodium borohydride was added portionwise and stirring was continued overnight. The mixture was evaporated to dryness, the mixture was taken up in dichloromethane and extracted with 2N HCl and brine. The organic layer was evaporated, the residue was taken up in methyl tert.butyl ether and extracted several times with 2N HCl. The combined HCl layers were adjusted to pH 12 by addition of 5N sodium hydroxide and extracted with dichloromethane. The dichloromethane layer was dried over MgSO$_4$ and evaporated to give 13.0 g of the desired product.

cis-4-(1-Amino-1-methyl-ethyl)-4-(4-fluoro-phenyl) cyclohexanol (79)

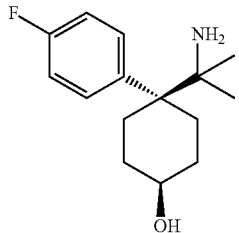 [SMILES: CC(C)(N)[C@]1(c2ccc(F)cc2)CC[C@H](O)CC1]

300 mg of 78 were dissolved in 10 mL of dry diethyl ether. Then, 0.3 mL of methyl magnesium bromide (3M in diethyl ether) were added. The mixture was cooled to 0° C. and 0.85 mL of a solution of methyl lithium (1.6 M) were added. After 1 h, 255 mg of titanium(IV) isopropoxide were added. 10 minutes later 1.4 mL of a solution of methyl lithium (1.6 M) in diethylether were added. The mixture was stirred overnight. Then 5 mL of 2N sodium hydroxide were added slowly at 0° C., 30 mL of methyl tert.butyl ether were added and the NaOH layer was extracted several times with methyl tert.butyl ether. The combined organic layer was dried and evaporated. The resulting residue was dissolved in 5 mL of methyl tert.butyl ether, cooled to 0° C. and 5 mL of 2N hydrochloric acid were added. Stirring was continued overnight, the ether layer was extracted again with 2N hydrochloric acid and the combined aqueous layer was cooled to 0° C. and 4 mL of 5N sodium hydroxide solution were added. The aqueous layer was extracted several times with dichloromethane, the combined dichloromethane layers were dried and evaporated to give 80 mg of the desired product. R$_t$=2.33 min (Method 3). Detected mass: 217.2 (M+H$^+$)

8-(4-Fluoro-phenyl)-1,4-dioxa-spiro[4.5]decane-8-carbonitrile (15)

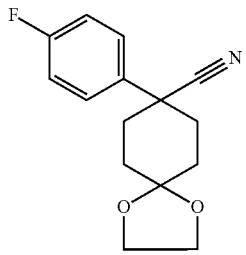 [SMILES: N#CC1(c2ccc(F)cc2)CCC2(CC1)OCCO2]

15 g of 1-(4-Fluoro-phenyl)-4-oxo-cyclohexanecarbonitrile (12) were dissolved in 500 mL of toluene, then 900 mg of p-toluene sulfonic acid were added and the reaction mixture was heated in a Dean-Stark apparatus for 6 h. The mixture was allowed to cool to room temperature and washed twice with saturated aqueous sodium bicarbonate solution and brine, dried over magnesium sulphate and evaporated to dryness to yield 17.9 g of the desired product. R$_t$=1.47 min (Method 5). Detected mass: 262.2 (M+H$^+$).

{1-[8-(4-Fluoro-phenyl)-1,4-dioxa-spiro[4.5]dec-8-yl]-butyl}-carbamic acid tert-butyl ester (16)

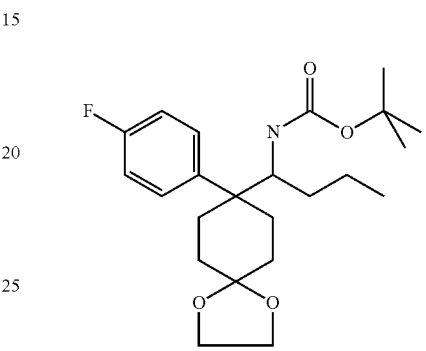

1.5 g of 8-(4-Fluoro-phenyl)-1,4-dioxa-spiro[4.5]decane-8-carbonitrile (15) were dissolved in 2.9 mL of a 2M solution of propylmagnesium chloride in diethylether. The mixture was heated under reflux overnight. Another equivalent of propylmagnesium chloride solution was added and heating was continued for another day. The mixture was diluted by diethyl ether (THF could be used alternatively) and a minimal amount of saturated sodium sulphate solution was added. The mixture was filtered over celite and the precipitate was washed with diethyl ether. 490 mg of sodium borohydride was added to the combined organic layer and the mixture was allowed to stir until conversion was complete. A mixture of 2N HCl, brine and water (1:3:6) was added. The phases were separated, the organic layer was extracted twice with the mixture of 2N HCl, brine and water (1:3:6). The combined aqueous layer was adjusted to alkaline pH by addition of 2M sodium hydroxide solution and extracted twice with dichloromethane. The combined dichloromethane layer was washed with brine, and dried over sodium sulphate.

5 mL of triethylamine and 5.86 g of di-tert.-butyl dicarbonate were added to the dichloromethane layer and the mixture was stirred at room temperature overnight. The mixture was washed with 1N sodium hydroxide, a mixture of 2N hydrochloric acid, brine and water (1:3:6) and brine, dried over sodium sulphate and evaporated to dryness. The crude product was purified by silica gel chromatography (heptanes:ethyl acetate) to give 1.22 g of the desired product. $R_t$=5.18 min (Method 3). Detected mass: 815.4 (2M+H$^+$).

{1-[1-(4-Fluoro-phenyl)-4-oxo-cyclohexyl]-butyl}-carbamic acid tert-butyl ester (17)

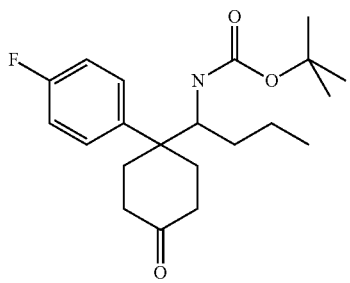 [SMILES: CCCC(NC(=O)OC(C)(C)C)C1(c2ccc(F)cc2)CCC(=O)CC1]

1.22 g of {1-[8-(4-fluoro-phenyl)-1,4-dioxa-spiro[4.5]dec-8-yl]-butyl}-carbamic acid tert-butyl ester (16) were dissolved in 42 mL of acetone and 3 mL of 1N hydrochloric acid were added. The mixture was stirred at room temperature until conversion was complete. 40 mL of saturated aqueous sodium bicarbonate solution were added and the reaction mixture was extracted with ethyl acetate three times. The combined organic layer was extracted with brine, dried over sodium sulphate and evaporated to dryness to give 966 mg of crude (17), that was sufficiently pure for further conversion. $R_t$=1.72 min (Method 5). Detected mass: 308.2 (M-Isobutene+H$^+$).

trans-{1-[1-(4-Fluoro-phenyl)-4-hydroxy-cyclohexyl]-butyl}-carbamic acid tert-butyl ester (18)

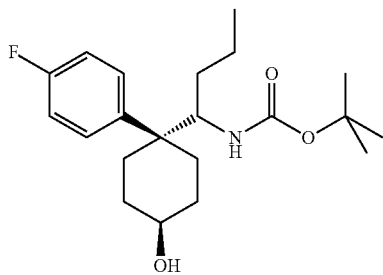 [SMILES: CCCC(NC(=O)OC(C)(C)C)[C@]1(c2ccc(F)cc2)CC[C@@H](O)CC1]

0.97 g of {1-[1-(4-Fluoro-phenyl)-4-oxo-cyclohexyl]-butyl}-carbamic acid tert-butyl ester (17) were dissolved in 14 mL of ethanol and 119 mg of sodium borohydride were added at −20° C. The mixture was allowed to warm to room temperature and stirred overnight. The mixture was evaporated, the residue was dissolved in ethyl acetate and washed twice with 2N hydrochloric acid and once with brine. The organic layer was dried over sodium sulphate and evaporated to dryness to give the crude product, that was purified by silica gel chromatography (heptanes:ethyl acetate) to give 619 mg of (18). $R_t$=3.46 min (Method 1). Detected mass: 366.3 (M+H$^+$).

trans-4-(1-Amino-butyl)-4-(4-fluoro-phenyl)cyclohexanol (19)

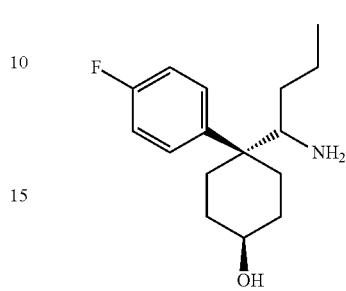

619 mg of trans-{1-[1-(4-Fluoro-phenyl)-4-hydroxy-cyclohexyl]-butyl}-carbamic acid tert-butyl ester (18) were dissolved in 2 mL of isopropanol and 2 mL of 2N aqueous hydrochloric acid were added. The mixture was stirred overnight. Water was added and the isopropanol was removed in vacuo. The residue was taken up in water and lyophilized for another two times to give 1.64 g of (19) as the hydrochloride. $R_t$=2.27 min (Method 1). Detected mass: 266.2 (M+H$^+$).

[1-Methyl-1-(4-oxo-cyclohexyl)-ethyl]-carbamic acid tert-butyl ester (20)

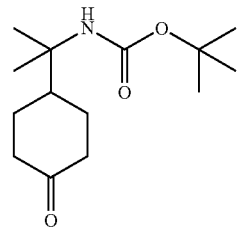 [SMILES: CC(C)(C)OC(=O)NC(C)(C)C1CCC(=O)CC1]

A suspension of commercial anhydrous cerium chloride (ABCR, 8.8 g) in anhydrous THF (62 mL) was heated for 4 h at 60° C. under vigourous stirring. The slurry was cooled to room temperature and treated with 3 g of 4-cyanocyclohexanone cyclic ethylene acetal. After cooling to −20° C., 35 mL of a 1.5 M solution of MeLi.LiBr in diethyl ether were added dropwise. The mixture was allowed to stir for 1 h at −10° C., then 20 mL of THF were added and the reaction was quenched by addition of concentrated NH$_4$OH (10 mL) over 10 min. The mixture was allowed to warm to room temperature, stirred for 30 min, diluted with methyl tert. butyl ether and then filtered. The filter cake was rinsed several times with methyl tert. butyl ether. The combined filtrates were then concentrated in vacuo.

The crude product was dissolved in dichloromethane and extracted twice with 0.1N HCl. The combined HCl layers were washed with dichloromethane, cooled and the pH was adjusted to 12 by addition of 5 N sodium hydroxide solution. The aqueous layer was extracted twice with dichloromethane. The dichloromethane layers were combined, washed with brine, and dried over sodium sulphate.

1.82 g of triethylamine and 2.74 g of di-tert.-butyl dicarbonate were added. The mixture was stirred for two days at room temperature, washed with 1N sodium hydroxide solution, twice with 0.1 N hydrochloric acid and water, and once with brine, dried over sodium sulphate and evaporated to dryness to give 3.0 g of crude product.

The crude product was dissolved in 100 mL of acetone and 10 mL of 1N HCl were added and stirred at room temperature. Additional HCl was added and stirring was continued until conversion was complete. Sodium hydroxide solution and methyl-tert.-butyl ether was added, the aqueous layer was separated and extracted with methyl-tert.-butyl ether. The combined ether layers were dried over sodium sulphate and evaporated to dryness to give 2.4 g of (20). $R_t$=3.08 min (Method 1). Detected mass: 256.2 (M+H$^+$).

[1-Methyl-1-(4-hydroxy-cyclohexyl)-ethyl]carbamic acid tert-butyl ester (21)

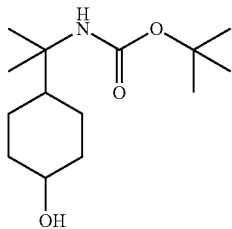 [SMILES: CC(C)(C)OC(=O)NC(C)(C)C1CCC(O)CC1]

2.91 g of [1-Methyl-1-(4-oxo-cyclohexyl)-ethyl]-carbamic acid tert-butyl ester (20) were dissolved in 60 mL of ethanol and 473 mg of sodium borohydride were added at −20° C. The mixture was allowed to warm to room temperature and stirred for 3.5 h. The mixture was evaporated, the residue was dissolved in ethyl acetate and washed twice with 2N hydrochloric acid and once with brine. The organic layer was dried over sodium sulphate and evaporated to dryness to give 2.74 g of (21). $R_t$=1.27 min (Method 5). Detected mass: 194 (M-Isobutene-H$_2$O+H$^+$).

4-(1-Amino-1-methyl-ethyl)-cyclohexanol (22)

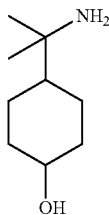

580 mg of [1-Methyl-1-(4-hydroxy-cyclohexyl)-ethyl]-carbamic acid tert-butyl ester (21) were dissolved in 10 mL of isopropanol and 10 mL of 2N hydrochloric acid were added. The mixture was stirred overnight. Water was added and the isopropanol was removed in vacuo. The residue was taken up in water and lyophilized for another two times from water to give 515 mg of (22) as the hydrochloride. $R_t$=0.18 min (Method 5). Detected mass: 158.2 (M+H$^+$).

Example 1 cis-6-[4-(1-Amino-propyl)-4-(4-fluoro-phenyl)-cyclohexyloxy]-7-chloro-2H-isoquinolin-1-one a) cis-1-[4-(7-Chloro-1-methoxy-isoquinolin-6-yloxy)-1-(4-fluoro-phenyl)-cyclohexyl]-propylamine (23)

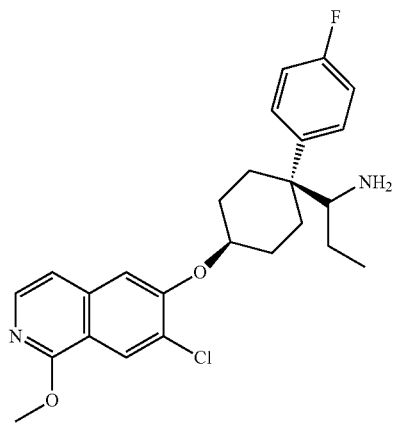 [SMILES: CCC(N)[C@]1(c2ccc(F)cc2)CC[C@H](Oc2cc3ccnc(OC)c3cc2Cl)CC1]

1.7 g of cis-4-(1-Amino-propyl)-4-(4-fluoro-phenyl)-cyclohexanol (14) were dissolved under argon in 50 mL of dry dimethyl acetamide. 513 mg of sodium hydride (95%) were added portionwise under cooling and the mixture was allowed to stir for 10 minutes. 1.57 g of 7-Chloro-6-fluoro-1-methoxy-isoquinoline (10) were added and the mixture was heated at 50° C. for 3 h. Stirring was continued overnight at room temperature. The reaction mixture was cooled in an ice bath and 50 mL of water were added carefully. The mixture was extracted four times with dichloromethane:isopropanol (3:1) and the combined organic layer was washed three times with water and once with brine, dried over sodium sulphate and evaporated to dryness. Water was added and the mixture was lyophilized. The crude product was subjected to silica gel chromatography (dichloromethane:methanol) to give 1.66 g of the desired product. $R_t$=3.45 min (Method 1). Detected mass: 443.2 (M+H$^+$).

b) cis-6-[4-(1-Amino-propyl)-4-(4-fluoro-phenyl)-cyclohexyloxy]-7-chloro-2H-isoquinolin-1-one (Example 1)

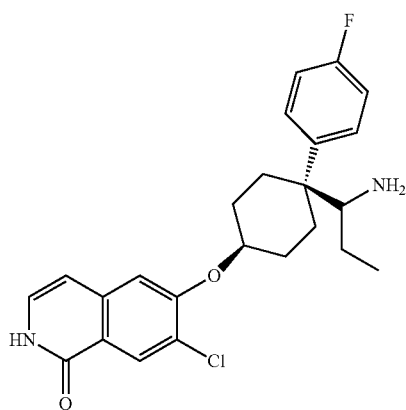

1.66 g of cis-1-[4-(7-Chloro-1-methoxy-isoquinolin-6-yloxy)-1-(4-fluoro-phenyl)-cyclohexyl]-propylamine (23) were dissolved in 16 mL of a mixture of isopropanol and 1N hydrochloric acid (1:1) and heated in a microwave oven for 20 minutes at 120° C. Water was added, the isopropanol removed in vacuo and the remaining solution was lyophilized. The residue was taken up in water and lyophilized for another two times from water to give 1.64 g of the desired product Example 1 as the hydrochloride. $R_t$=2.67 min (Method 1). Detected mass: 429.2 (M+H$^+$).

Example 2 cis-6-[4-(1-Amino-cyclopropyl)-4-phenyl-cyclohexyloxy]-7-chloro-2H-isoquinolin-1-one a) cis-1-[4-(1-Benzyloxy-7-chloro-isoquinolin-6-yloxy)-1-phenyl-cyclohexyl]-cyclopropylamine (24)

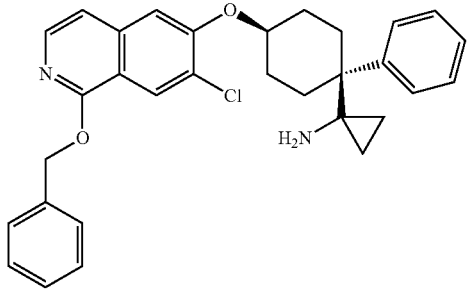 [SMILES: NC1([C@]2(c3ccccc3)CC[C@H](Oc3cc4ccnc(OCc5ccccc5)c4cc3Cl)CC2)CC1]

To a solution of dry cis-4-(1-aminocyclopropyl)-4-phenyl-cyclohexanol (4, 0.2 g, 0.75 mmol) in anhydrous N,N-dimethylacetamide (5 mL) at 0° C. was added portionwise sodium hydride (60% in mineral oil, 0.12 g, 3 mmol). The reaction mixture was stirred for 10 min at room temperature, 1-(benzyloxy)-7-chloro-6-fluoroisoquinoline (38, 0.28 g, 0.97 mmol) was then added and stirring was continued overnight. The suspension was poured onto ice, the resulting precipitate was filtered and dried. The crude product was purified by chromatography on silica gel (eluting with 0 to 5% methanol in dichloromethane containing 1% ammonia) to yield 0.252 g of the desired product. $R_t$=6.21 min (Method 9). Detected mass: 499 (M+H$^+$).

b) cis-6-[4-(1-Amino-cyclopropyl)-4-phenyl-cyclohexyloxy]-7-chloro-2H-isoquinolin-1-one (Example 2)

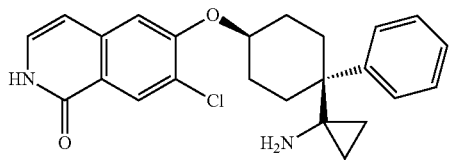 [SMILES: NC1([C@]2(c3ccccc3)CC[C@H](Oc3cc4cc[nH]c(=O)c4cc3Cl)CC2)CC1]

To a solution of cis-1-[4-[[7-chloro-1-(phenylmethoxy)-6-isoquinolinyl]oxy]-1-phenylcyclohexyl]-cyclopropanamine (24, 0.24 g, 0.48 mmol) in isopropanol (2.5 mL) was added a solution of 4N aqueous hydrochloric acid (2.5 mL, 10 mmol) followed by 2.5 mL of isopropanol, 2.5 mL of 4N aqueous hydrochloric acid (10 mmol) and eventually 2.5 mL of methanol. The resulting suspension was stirred overnight, evaporated under reduced pressure and co-evaporated with a methanol/toluene mixture. The crude product was triturated with methanol/diethyl ether to afford 0.18 g of the title compound as its hydrochloride. $R_t$=4.83 min (Method 9). Detected mass: 409 (M+H$^+$).

Example 3 cis-6-{[4-(1-aminopropyl)-4-phenylcyclohexyl]oxy}-7-chloro-2H-isoquinolin-1-one a) cis-1-(4-{[1-(benzyloxy)-7-chloroisoquinolin-6-yl]oxy}phenylcyclohexyl)-propanamine (25)

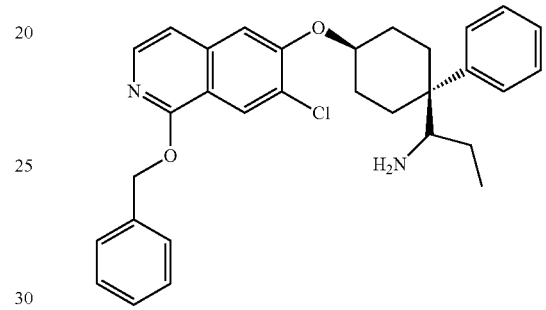

To a solution of cis-4-(1-aminopropyl)-4-phenylcyclohexanol (6, 0.39 g, 1.48 mmol) in anhydrous N,N-dimethylacetamide (10 mL) was added portionwise sodium hydride (60% in mineral oil, 0.24 g, 5.92 mmol). The reaction mixture was stirred for 10 min at room temperature, then 1-(benzyloxy)-7-chloro-6-fluoroisoquinoline (38, 0.42 g, 1.48 mmol) was added and stirring was continued for 72 hours. The suspension was poured onto ice, the resulting aqueous layer was extracted with chloroform. The organic layers were dried over sodium sulphate, filtered and concentrated under reduced pressure. The crude product was purified by chromatography on silica gel (eluting with 0 to 10% methanol in dichloromethane) to yield 0.604 g of cis-1-(4-{[1-(benzyloxy)-7-chloroisoquinolin-6-yl]oxy}-1-phenylcyclohexyl)propanamine (25). $R_t$=4.18 min (Method 8). Detected mass: 501 (M+H$^+$).

b) cis-6-{[4-(1-aminopropyl)-4-phenylcyclohexyl]oxy}-7-chloro-2H-isoquinolin-1-one (Example 3)

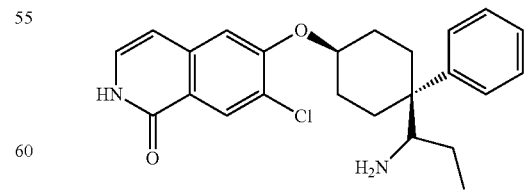

To a solution of cis-1-(4-{[1-(benzyloxy)-7-chloroisoquinolin-6-yl]oxy}-1-phenylcyclohexyl)propanamine (25, 0.604 g, 1.21 mmol) in isopropanol (6.3 mL) was added a solution of 1N aqueous hydrochloric acid (7 mL, 7 mmol).

The resulting suspension was stirred overnight and evaporated under reduced pressure. The crude product was purified by reversed phase column chromatography (eluting with 0 to 30% $CH_3CN$ in water) to afford the title compound (0.32 g). $R_t$=5.00 min (Method 9). Detected mass: 411 (M+H$^+$).

The following examples were prepared in a similar fashion as described for Example 1, starting from a suitably protected isoquinolinone and the respective aminoalcohol.

Aminoalcohols were synthesized from the corresponding benzonitriles and grignard reagents: trans-aminoalcohols were obtained in a similar fashion as described in the reaction sequence to yield (19), cis-aminoalcohols were obtained in a similar fashion as described in the reaction sequence to yield (14). Dimethylated aminoalcohols were obtained in a similar fashion as described for (22). All described products were obtained as the hydrochloride salts.

| Ex. No. | Isoquinoline | Product | Chemical Name | [M + H$^+$] | $R_t$/ [min] | Method |
|---|---|---|---|---|---|---|
| 4 | 10 | | cis-6-[4-(1-Amino-butyl)-4-phenyl-cyclo hexyloxy]-7-chloro-2H-isoquinolin-1-one | 425.2 | 2.61 | 1 |
| 5 | 10 | | cis-6-[4-(1-Amino-butyl)-4-(4-fluoro-phenyl)-cyclo-hexyloxy]-7-chloro-2H-isoquinolin-1-one | 443.2 | 2.66 | 1 |
| 6 | 10 | | cis-6-[4-(1-Amin-propyl)-4-(4-bromo-phenyl)-cyclo hexyloxy]-7-chloro-2H-isoquinolin-1-one | 489.1 | 2.69 | 1 |

| Ex. No. | Isoquinoline | Product | Chemical Name | [M + H⁺] | R_f [min] | Method |
|---|---|---|---|---|---|---|
| 7 | 10 | | cis-6-[4-(1-Amino-propyl)-4-(2-bromo-phenyl)-cyclohexyloxy]-7-chloro-2H-isoquinolin-1-one | 489.1 | 2.64 | 1 |
| 8 | 10 | | cis-6-[4-(1-Amino-propyl)-4-(4-trifluoromethyl-phenyl)-cyclo-hexyloxy]-7-chloro-2H-isoquinolin-1-one | 479.2 | 2.74 | 1 |
| 9 | 10 | | cis-6-[4-(1-Amino-propyl)-4-(2-fluoro-phenyl)-cyclohexyloxy]-7-chloro-2H-isoquinolin-1-one | 429.2 | 2.52 | 1 |
| 10 | 10 | | cis-6-[4-(1-Amino-propyl)-4-(2-chloro-phenyl)-cyclohexyloxy]-7-chloro-2H-isoquinolin-1-one | 445.1 | 2.71 | 1 |

-continued

| Ex. No. | Isoqui- noline | Product | Chemical Name | [M + H⁺] | R$_t$/ [min] | Method |
|---|---|---|---|---|---|---|
| 11 | 39 | | cis-6-[4-(1-Amino-propyl)-4-phenyl-cyclohexyloxy]-7-methyl-2H-isoquinolin-1-one | 391.2 | 2.56 | 1 |
| 12 | 38 | | trans-6-[4-(1-Amino-butyl)-4-(4-fluoro-phenyl)-cyclohexyloxy]-7-chloro-2H-isoquinolin-1-one | 443.2 | 2.63 | 1 |
| 13 | 38 | | trans-6-[4-(1-Amino-ethyl)-4-(4-fluoro-phenyl)-cyclohexyloxy]-7-chloro-2H-isoquinolin-1-one | 415.2 | 2.48 | 1 |
| 14 | 38 | | trans-6-[4-(1-Amino-butyl)-4-phenyl-cyclohexyloxy]-7-chloro-2H-isoquinolin-1-one | 425.2 | 2.67 | 1 |

-continued

| Ex. No. | Isoquinoline | Product | Chemical Name | [M + H⁺] | R$_f$/ [min] | Method |
|---|---|---|---|---|---|---|
| 15 | 38 | | cis-6-[4-(1-Amino-ethyl)-4-(4-fluoro-phenyl)-cyclohexyloxy]-7-chloro-2H-isoquinolin-1-one | 415.2 | 2.48 | 1 |
| 16 | 10 | | trans-6-[4-(1-Amino-propyl)-4-(3-bromo-phenyl)-cyclohexyloxy]-7-chloro-2H-isoquinolin-1-one | 489.2 | 2.77 | 2 |
| 17 | 10 | | trans-6-[4-(1-Amino-propyl)-4-(3-methoxy-phenyl)-cyclohexyloxy]-7-chloro-2H-isoquinolin-1-one | 441.2 | 2.65 | 2 |
| 18 | 10 | | trans-6-[4-(Amino-phenyl-methyl)-4-(4-fluoro-phenyl)-cyclohexyloxy]-7-chloro-2H-isoquinolin-1-one | 477.2 | 2.67 | 1 |

-continued

| Ex. No. | Isoquinoline | Product | Chemical Name | [M + H⁺] | R$_t$/[min] | Method |
|---|---|---|---|---|---|---|
| 19 | 10 | 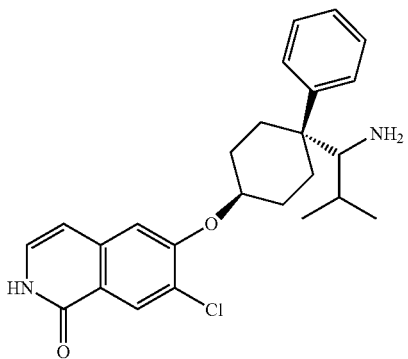 [SMILES: CC(C)C(N)[C@]1(c2ccccc2)CC[C@@H](Oc2cc3cc[nH]c(=O)c3cc2Cl)CC1] | trans-6-[4-(1-Amino-2-methyl-propyl)-4-phenyl-cyclohexyloxy]-7-chloro-2H-isoquinolin-1-one | 425.3 | 3.33 | 6 |
| 20 | 10 | 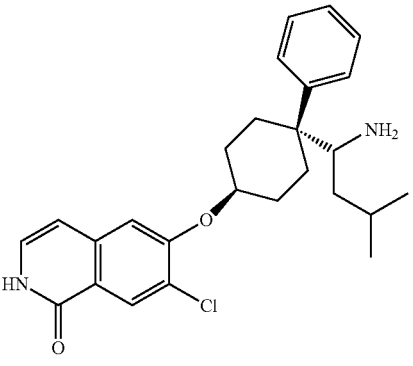 [SMILES: CC(C)CC(N)[C@]1(c2ccccc2)CC[C@@H](Oc2cc3cc[nH]c(=O)c3cc2Cl)CC1] | trans-6-[4-(1-Amino-3-methyl-butyl)-4-phenyl-cyclohexyloxy]-7-chloro-2H-isoquinolin-1-one | 439.4 | 2.74 | 1 |
| 21 | 10 | 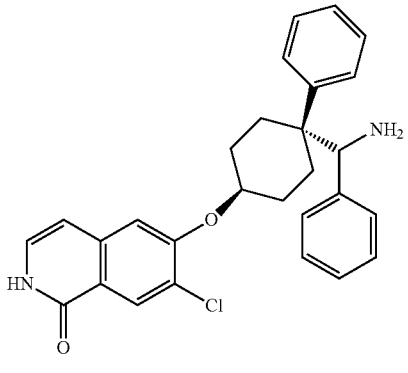 [SMILES: NC(c1ccccc1)[C@]1(c2ccccc2)CC[C@@H](Oc2cc3cc[nH]c(=O)c3cc2Cl)CC1] | trans-6-[4-(Amino-phenyl-methyl)-4-phenyl-cyclohexyloxy]-7-chloro-2H-isoquinolin-1-one | 458.2 | 2.78 | 1 |
| 22 | 38 | 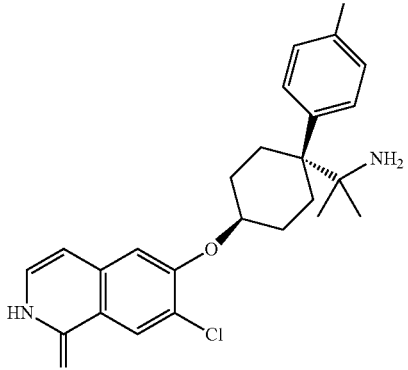 | trans-6-[4-(1-Amino-1-methyl-ethyl)-4-(4-fluoro-phenyl)-cyclohexyloxy]-7-chloro-2H-isoquinolin-1-one | 429.1 | 2.64 | 1 |

-continued

| Ex. No. | Isoquinoline | Product | Chemical Name | [M + H⁺] | R$_t$/ [min] | Method |
|---|---|---|---|---|---|---|
| 23 | 38 | | cis-6-[4-(1-Amino-cyclopropyl)-4-(2-fluoro-phenyl)-cyclohexyloxy]-7-chloro-2H-isoquinolin-1-one | 427 | 3.29 | 8 |
| 24 | 38 | | cis-6-[4-(1-Amino-ethyl)-4-phenyl-cyclohexyloxy]-7-chloro-2H-isoquinolin-1-one | 397 | 3.19 | 8 |
| 25 | 38 | | cis-6-[4-(1-Amino-1-methyl-ethyl)-4-phenyl-cyclo-hexyloxy]-7-chloro-2H-isoquinolin-1-one | 411 | 0.62 | 7 |
| 26 | 38 | | cis-6-(4-[amino(cyclopropyl)methyl]-4-phenyl-cyclohexyl}oxy)-7-chloro-2H-isoquinolin-1-one | 423 | 5.10 | 9 |
| 27 | 10 | | cis-6-[4-(1-Amino-propyl)-4-(4-isopropyl-phenyl)-cyclohexyloxy]-7-chloro-2H-isoquinolin-1-one | 453.2 | 1.20 | 5 |
| 28 | 10 | | cis-6-[4-(1-Amino-propyl)-4-(3-methoxy)-phenyl)-cyclohexyloxy]-7-chloro-2H-isoquinolin-1-one | 441.2 | 1.07 | 5 |

-continued

| Ex. No. | Isoquinoline | Product | Chemical Name | [M + H⁺] | R_f [min] | Method |
|---|---|---|---|---|---|---|
| 29 | 10 | | cis-6-[4-(1-Amino-propyl)-4-(3-bromo-phenyl)-cyclohexyloxy]-7-chloro-2H-isoquinolin-1-one | 503.1 | 1.34 | 5 |
| 30 | 10 | | cis-6-[4-(1-Amino-2-methyl-propyl)-4-(4-fluoro-phenyl)-cyclohexyloxy]-7-chloro-2H-isoquinolin-1-one | 443.2 | 2.66 | 1 |
| 31 | 10 | | trans-6-[4-(1-amino-propyl)-4-(4-fluoro-phenyl)-cyclohexyloxy]-7-chloro-2H-isoquinolin-1-one | 429.2 | 2.57 | 1 |
| 32 | 38 | | trans-6-[4-(1-amino-propyl)-4-phenyl)-cyclohexyloxy]-7-chloro-2H-isoquinolin-1-one | 411.2 | 2.69 | 1 |

| Ex. No. | Isoquinoline | Product | Chemical Name | [M + H⁺] | R$_t$/ [min] | Method |
|---|---|---|---|---|---|---|
| 55 | 10 | 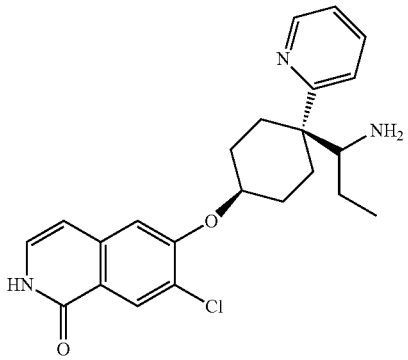 [SMILES: CCC(N)[C@]1(c2ccccn2)CC[C@H](Oc2cc3cc[nH]c(=O)c3cc2Cl)CC1] | cis-6-[4-(1-Amino-propyl)-4-pyridin-2-yl-cyclohexyloxy]-7-chloro-2H-isoquinolin-1-one | 412.2 | 1.77 | 13 |
| 56 | 10 | 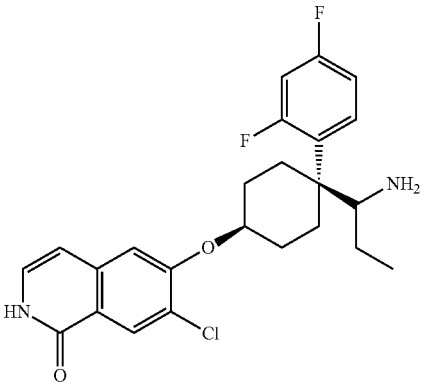 [SMILES: CCC(N)[C@]1(c2ccc(F)cc2F)CC[C@H](Oc2cc3cc[nH]c(=O)c3cc2Cl)CC1] | cis-6-[4-(1-Amino-propyl)-4-(2,4-difluoro-phenyl)-cyclohexyloxy]-7-chloro-2H-isoquinolin-1-one | 447.1 | 1.84 | 12 |
| 57 | 10 | 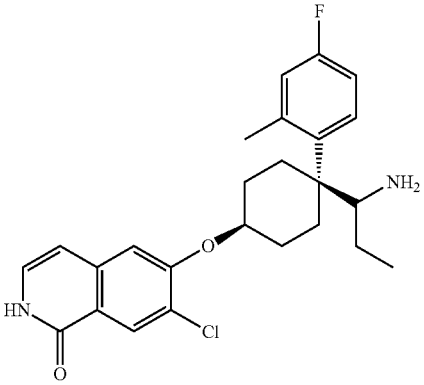 [SMILES: CCC(N)[C@]1(c2ccc(F)cc2C)CC[C@H](Oc2cc3cc[nH]c(=O)c3cc2Cl)CC1] | cis-6-[4-(1-Amino-propyl)-4-(4-fluoro-2-methyl-phenyl)cyclohexyloxy]-7-chloro-2H-isoquinolin-1-one | 443.1 | 1.89 | 12 |
| 58 | 10 | 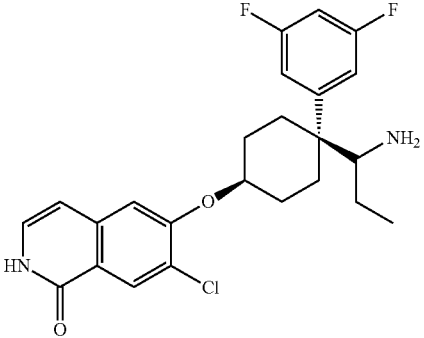 [SMILES: CCC(N)[C@]1(c2cc(F)cc(F)c2)CC[C@H](Oc2cc3cc[nH]c(=O)c3cc2Cl)CC1] | cis-6-[4-(1-Amino-propyl)-4-(3,5-difluoro-phenyl)-cyclohexyloxy]-7-chloro-2H-isoquinolin-1-one | 447.1 | 1.86 | 12 |

-continued

| Ex. No. | Isoquinoline | Product | Chemical Name | [M + H⁺] | R_f [min] | Method |
|---|---|---|---|---|---|---|
| 59 | 10 | | cis-6-[4-(1-Amino-propyl)-4-(3,4-difluoro-phenyl)-cyclohexyloxy]-7-chloro-2H-isoquinolin-1-one | 447.1 | 1.87 | 12 |
| 60 | 10 | | cis-6-[4-(1-Amino-propyl)-4-o-tolyl-cyclohexyloxy]-7-chloro-2H-isoquinolin-1-one | 425.1 | 1.82 | 12 |
| 61 | 10 | | cis-6-[4-(1-Amino-propyl)-4-(2-trifluoromethoxy-phenyl)-cyclohexyloxy]-7-chloro-2H-isoquinolin-1-one | 495.2 | 1.97 | 12 |
| 62 | 10 | | cis-6-[4-(1-Amino-propyl)-4-(4-fluoro-3-methoxy-phenyl)-cyclohexyloxy]-7-chloro-2H-isoquinolin-1-one | 459.3 | 1.28 | 16 |

| Ex. No. | Isoquinoline | Product | Chemical Name | [M + H⁺] | R_f/[min] | Method |
|---|---|---|---|---|---|---|
| 63 | 10 | | cis-6-[4-(1-Amino-propyl)-4-(3-ethoxy-phenyl)-cyclohexyloxy]-7-chloro-2H-isoquinolin-1-one | 455.3 | 1.24 | 16 |
| 64 | 10 | | cis-6-[4-(1-Amino-propyl)-4-(3-methoxy-4-methyl-phenyl)-cyclohexyloxy]-7-chloro-2H-isoquinolin-1-one | 438.2 (M + H⁺ − NH₃) | 3.69 | 3 |
| 65 | 52 | | cis-6-[4-(1-Amino-propyl)-4-(3,4-difluoro-phenyl)-cyclohexyloxy]-7-methyl-2H-isoquinolin-1-one | 427.2 | 1.38 | 10 |
| 66 | 50 | | cis-6-[4-(1-Amino-propyl)-4-(3,5-difluoro-phenyl)-cyclohexyloxy]-7-fluoro-2H-isoquinolin-1-one | 431.2 | 1.36 | 10 |
| 67 | 51 | | cis-6-[4-(1-Amino-propyl)-4-(3,4-difluoro-phenyl)-cyclohexyloxy]-7-fluoro-5-methyl-2H-isoquinolin-1-one | 445.3 | 0.98 | 11 |

-continued

| Ex. No. | Isoquinoline | Product | Chemical Name | [M + H⁺] | R$_t$/ [min] | Method |
|---|---|---|---|---|---|---|
| 68 | 54 | 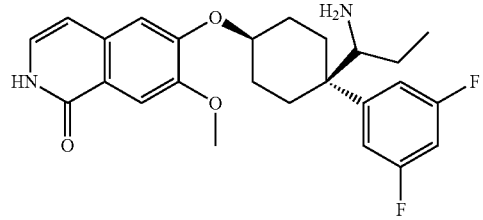 [SMILES: CCC(N)[C@]1(c2cc(F)cc(F)c2)CC[C@H](Oc2cc3cc[nH]c(=O)c3cc2OC)CC1] | cis-6-[4-(1-Amino-propyl)-4-(3,5-difluoro-phenyl)-cyclohexyloxy]-7-methoxy-2H-isoquinolin-1-one | 443.3 | 0.96 | 11 |
| 69 | 10 | 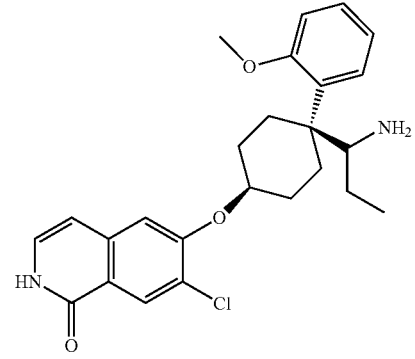 [SMILES: CCC(N)[C@]1(c2ccccc2OC)CC[C@H](Oc2cc3cc[nH]c(=O)c3cc2Cl)CC1] | cis-6-[4-(1-Amino-propyl)-4-(2-methoxy-phenyl)-cyclohexyloxy]-7-chloro-2H isoquinolin-1-one | 441.2 | 1.88 | 13 |
| 70 | 10 | 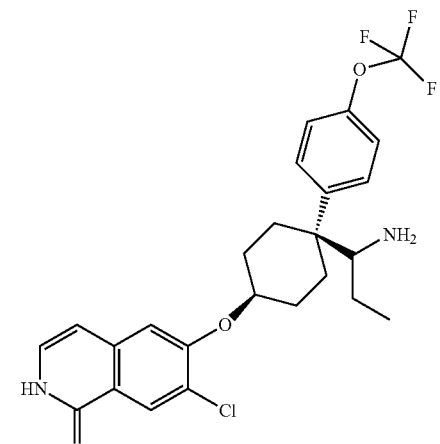 | cis-6-[4-(1-Amino-propyl)-4-(4-trifluoro-methoxy-phenyl)-cyclohexyloxy]-7-chloro-2H-isoquinolin-1-one | 495.2 | 2.32 | 14 |
| 71 | 7-Chloro-6-fluoro-isoquinoline | 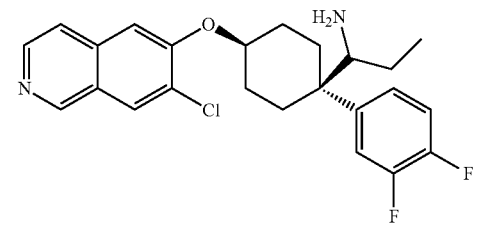 | cis-1-[4-(7-Chloro-isoquinolin-6-yloxy)-1-(3,4-difluoro-phenyl)-cyclohexyl]-propylamine | 431.3 | 2.28 | 2 |
| 72 | 46 | 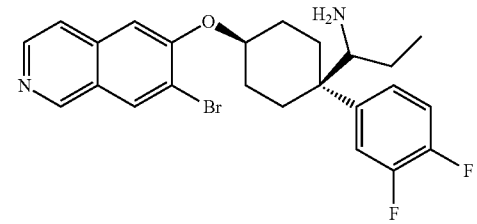 [SMILES: CCC(N)[C@]1(c2ccc(F)c(F)c2)CC[C@H](Oc2cc3ccncc3cc2Br)CC1] | cis-1-[4-(7-Bromo-isoquinolin-6-yloxy)-1-(3,4-difluoro-phenyl)-cyclohexyl]-propylamine | 475.3 | 2.34 | 2 |

| Ex. No. | Isoquinoline | Product | Chemical Name | [M + H+] | R_f [min] | Method |
|---|---|---|---|---|---|---|
| 73 | 44 | | cis-1-[1-(3,5-Difluoro-phenyl)-4-(5,7-dimethyl-isoquinolin-6-yloxy)-cyclohexyl]-propylamine | 425.3 | 0.87 | 11 |
| 74 | 43 | | cis-1-[1-(3,5-Difluoro-phenyl)-4-(7-fluoro-5-methyl-isoquinolin-6-yloxy)-cyclohexyl]-propylamine | 429.3 | 1.30 | 10 |
| 75 | 45 | | cis-1-[1-(3,4-Difluoro-phenyl)-4-(7-fluoro-isoquinolin-6-yloxy)-cyclohexyl]-propylamine | 415.3 | 2.24 | 2 |
| 76 | 7-Chloro-6-fluoro-isoquinoline | | cis-1-[4-(7-Chloro-isoquinolin-6-yloxy)-1-(3,5-difluoro-phenyl)-cyclohexyl]-propylamine | 431.1 | 1.20 | 10 |
| 77 | 10 | | cis-6-[4-(1-Amino-1-methyl-ethyl)-4-(4-fluoro-phenyl)-cyclohexyloxy]-7-chloro-2H-isoquinolin-1-one | 431.3 | 0.70 | 15 |
| 78 | 55 | | cis-6-[4-(1-Amino-propyl)-4-(3,5-difluoro-phenyl)-cyclohexyloxy]-4-benzyl-7-chloro-2H-isoquinolin-1-one | 537.2 | 1.50 | 10 |

-continued

| Ex. No. | Isoquinoline | Product | Chemical Name | [M + H⁺] | R$_t$ [min] | Method |
|---|---|---|---|---|---|---|
| 79 | 49 | | cis-6-[4-(1-Amino-propyl)-4-(3,5-difluoro-phenyl)-cyclohexyloxy]-5-chloro-2H-isoquinolin-1-one | 447.2 | 1.33 | 10 |
| 80 | 53 | | cis-6-[4-(1-Amino-propyl)-4-(3,5-difluoro-phenyl)-cyclohexyloxy]-5,7-dimethyl-2H-isoquinolin-1-one | 441.3 | 3.24 | 6 |
| 81 | 5-Chloro-6-fluoro-isoquinoline | | cis-1-[4-(5-Chloro-isoquinolin-6-yloxy)-1-(3,5-difluoro-phenyl)-cyclohexyl]-propylamine | 431.1 | 1.21 | 10 |
| 82 | 10 | | cis-6-[4-(Amino-cyclopropyl-methyl)-4-(4-fluoro-phenyl)-cyclohexyloxy]-7-chloro-2H-isoquinolin-1-one | 441.2 | 1.86 | 13 |
| 83 | 10 | | cis-6-[4-(1-Amino-propyl)-4-(3-trifluoromethyl-phenyl)-cyclohexyloxy]-7-chloro-2H-isoquinolin-1-one | 479.1 | 3.26 | 3 |

-continued

| Ex. No. | Isoquinoline | Product | Chemical Name | [M + H⁺] | R_f [min] | Method |
|---|---|---|---|---|---|---|
| 84 | 10 | | cis-6-[4-(1-Amino-propyl)-4-(3-trifluoromethoxy-phenyl)-cyclohexyloxy]-7-chloro-2H-isoquinolin-1-one | 495.1 | 1.97 | 12 |
| 85 | 52 | | cis-6-[4-(1-Amino-propyl)-4-(3-trifluoro-methoxy-phenyl)-cyclohexyloxy]-7-methyl-2H-isoquinolin-1-one | 475.3 | 1.36 | 16 |
| 86 | 52 | | cis-6-[4-(1-Amino-propyl)-4-(3-trifluoromethyl-phenyl)-cyclohexyloxy]-7-methyl-2H-isoquinolin-1-one | 459.2 | 1.32 | 16 |
| 87 | 50 | | cis-6-[4-(1-Amino-propyl)-4-phenyl-cyclohexyloxy]-7-fluoro-2H-isoquinolin-1-one | 395.2 | 1.37 | 10 |
| 88 | 51 | | cis-6-[4-(1-Amino-propyl)-4-phenyl-cyclohexyloxy]-7-fluoro-5-methyl-2H-isoquinolin-1-one | 409.3 | 0.96 | 11 |
| 89 | 7-chloro-6-fluoro-isoquinoline | | cis-1-[4-(7-Chloro-isoquinolin-6-yloxy)-1-phenyl-cyclohexyl]-propylamine | 395.2 | 1.20 | 10 |

-continued

| Ex. No. | Isoquinoline | Product | Chemical Name | [M + H⁺] | R$_t$/ [min] | Method |
|---|---|---|---|---|---|---|
| 90 | 44 | | cis-1-[4-(5,7-Dimethyl-isoquinolin-6-yloxy)-1-phenyl-cyclohexyl]-propylamine | 389.3 | 0.86 | 11 |
| 91 | 45 | | cis-1-[4-(7-Fluoro-isoquinolin-6-yloxy)-1-phenyl-cyclohexyl]-propylamine | 379.2 | 1.16 | 10 |
| 92 | 5-chloro-6-fluoro-isoquinoline | | cis-1-[4-(5-Chloro-isoquinolin-6-yloxy)-1-phenyl-cyclohexyl]-propylamine | 395.2 | 1.18 | 10 |
| 93 | 43 | | cis-1-[4-(7-Fluoro-5-methyl-isoquinolin-6-yloxy)-1-phenyl-cyclohexyl]propylamine | 393.2 | 1.20 | 10 |
| 94 | 46 | | cis-1-[4-(7-Bromo-isoquinolin-6-yloxy)-1-phenyl-cyclohexyl]-propylamine | 439.1 | 1.19 | 10 |
| 95 | 48 | | cis-1-[4-(7-Methyl-isoquinolin-6-yloxy)-1-phenyl-cyclohexyl]-propylamine | 375.3 | 1.22 | 10 |

| Ex. No. | Isoquinoline | Product | Chemical Name | [M + H⁺] | $R_f$/ [min] | Method |
|---|---|---|---|---|---|---|
| 96 | 55 | | cis-6-[4-(1-Amino-propyl)-4-phenyl-cyclohexyloxy]-4-benzyl-7-chloro-2H-isoquinolin-1-one | 501.3 | 1.50 | 10 |

Example 33 cis-6-[4-(1-Amino-propyl)-4-phenyl-cyclohexyloxy]-4-bromo-7-chloro-2H-isoquinolin-1-one

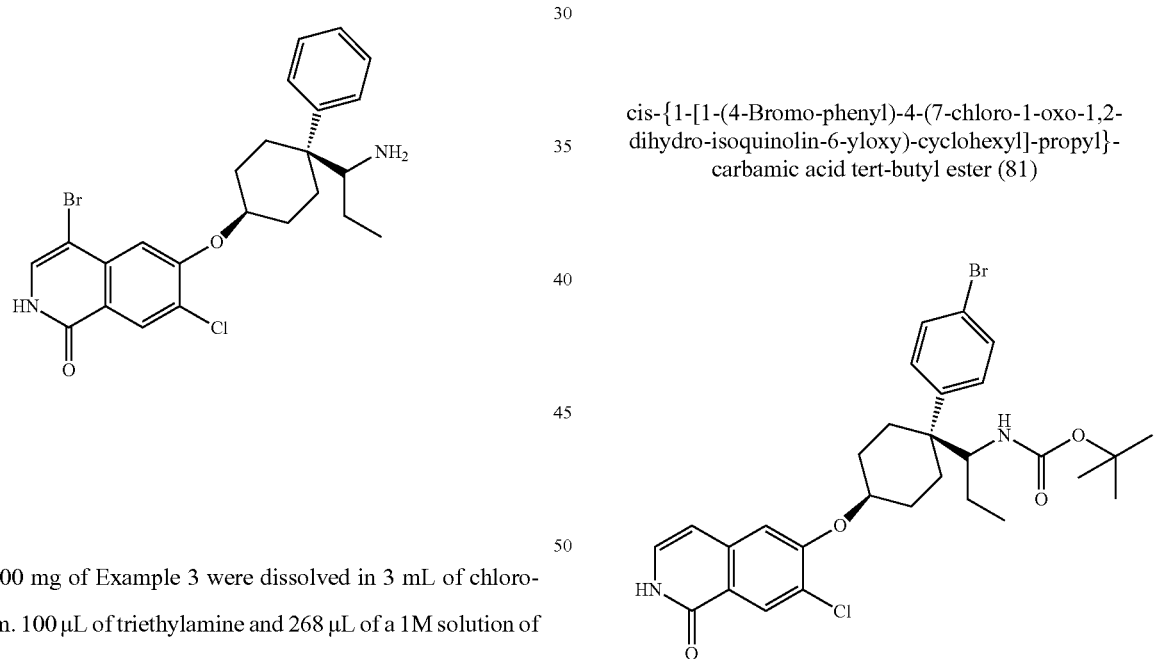

100 mg of Example 3 were dissolved in 3 mL of chloroform. 100 μL of triethylamine and 268 μL of a 1M solution of bromine in chloroform were added. The reaction was stirred at room temperature until conversion was complete. The mixture was quenched by addition of 11 mL sat. sodium thiosulfate solution. 5 mL of 2N sodium hydroxide solution were added and the aqueous layer was extracted three times with dichloromethane:isopropanol (3:1). The combined organic layer was washed with 2N NaOH and brine, dried over sodium sulphate and evaporated. The mixture was purified by HPLC and the obtained product was dissolved in 1 mL of isopropanol:1N HCl and heated in a microwave oven for 20 minutes at 100° C. The mixture was evaporated to dryness, taken up in water and lyophilized to give 29 mg of the desired product as the hydrochloride. $R_t$=2.77 min (Method 1). Detected mass: 491.1 (M+H⁺).

cis-{1-[1-(4-Bromo-phenyl)-4-(7-chloro-1-oxo-1,2-dihydro-isoquinolin-6-yloxy)-cyclohexyl]-propyl}-carbamic acid tert-butyl ester (81)

1.11 g of Example 6 were dissolved in 100 mL of dry dichloromethane. 1.2 mL of triethylamine and 1.44 g of di-tert.butyl dicarbonate were added. After conversion was complete, the mixture was extracted with 1N sodium hydroxide solution, 0.2 N hydrochloric acid, water and brine, dried and evaporated. The crude product was purified by silica gel filtration to give 886 mg of the desired product. $R_t$=4.00 min (Method 1). Detected mass: 533.0 (M+H-isobutene$^+$).

Example 97 cis-4-[1-(1-Amino-propyl)-4-(7-chloro-1-oxo-1,2-dihydro-isoquinolin-6-yloxy)-cyclohexyl]benzonitrile

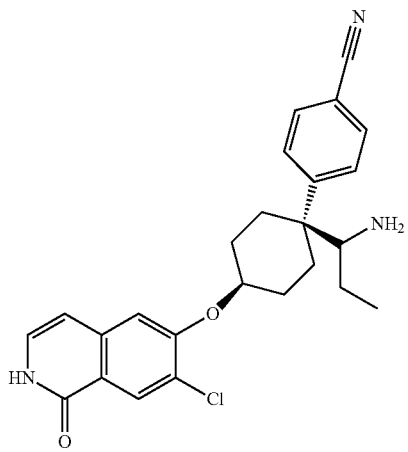 [SMILES: CCC(N)[C@]1(c2ccc(C#N)cc2)CC[C@H](Oc2cc3cc[nH]c(=O)c3cc2Cl)CC1]

200 mg of 81 were dissolved in 10 mL of degassed dimethyl formamide and 50 mg of zinc cyanide and 18 mg of tetrakis(triphenylphosphine)palladium(0) were added under argon. The mixture was heated in a microwave oven for 30 minutes at 150° C. The mixture was diluted with methyl tert. butyl ether and filtered over Celite. The organic layer was washed twice with water and once with brine, dried over sodium sulphate and evaporated to dryness. The crude product was purified by silica gel chromatography and subsequently taken up in 2 mL of isopropanol and 2 mL of 1N hydrochloric acid and heated in a microwave oven at 100° C. for 1 hour. Water was added and the mixture was lyophilized. The residue was taken up in water and lyophilized again to give 65 mg of the desired product as hydrochloride. $R_t$=2.55 min (Method 2). Detected mass: 436.2 (M+H$^+$).

Example 98 cis-3-[1-(1-Amino-propyl)-4-(7-chloro-1-oxo-1,2-dihydro-isoquinolin-6-yloxy)-cyclohexyl]benzonitrile

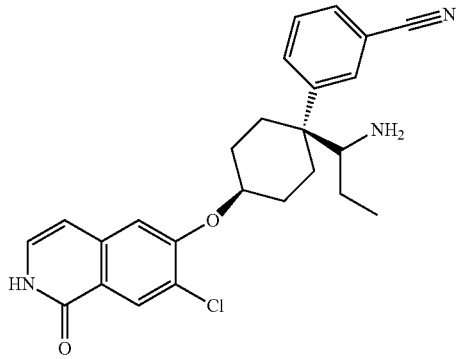 [SMILES: CCC(N)[C@]1(c2cccc(C#N)c2)CC[C@H](Oc2cc3cc[nH]c(=O)c3cc2Cl)CC1]

Example 98 can be obtained following a similar reaction sequence as used for the synthesis of Example 97, starting from Example 16. $R_t$=2.98 min (Method 3). Detected mass: 436.2 (M+H$^+$).

Example 99

6-[cis-4-(1-Amino-propyl)-4-(3-methanesulfonyl-phenyl)-cyclohexyloxy]-7-chloro-2H-isoquinolin-1-one a) cis-{1-[4-(7-Chloro-1-oxo-1,2-dihydro-isoquinolin-6-yloxy)-1-(3-methanesulfonyl-phenyl)-cyclohexyl]-propyl-carbamic acid tert-butyl ester (82)

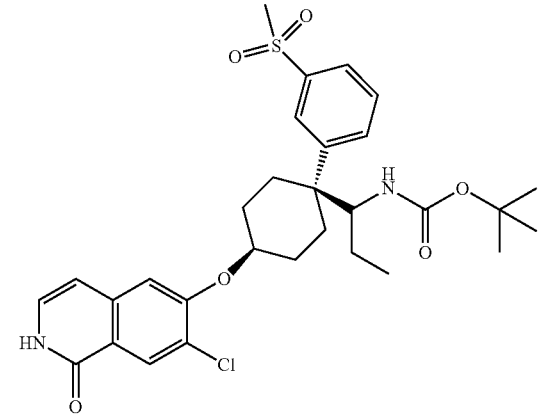 [SMILES: CCC(NC(=O)OC(C)(C)C)[C@]1(c2cccc(S(C)(=O)=O)c2)CC[C@H](Oc2cc3cc[nH]c(=O)c3cc2Cl)CC1]

330 mg (559 µmol) of cis-{1-[1-(3-Bromo-phenyl)-4-(7-chloro-1-oxo-1,2-dihydro-isoquinolin-6-yloxy)-cyclohexyl]-propyl}-carbamic acid tert-butyl ester (obtained from Example 29 as described for synthesis of 81), 213 mg (1.1 mmol) CuI and 114 mg (1.1 mmol) methansulfinic acid sodium salt were dissolved in 10 mL of anhydrous NMP. The mixture was stirred at 150° C. for 1 h under microwave irradiation, then poured into 100 mL of a saturated aqueous NaHCO$_3$-solution and extracted three times using 30 mL of ethyl acetate each. The organic layer was then washed five times using 20 mL of water each, dried over MgSO$_4$, filtered and the solvent removed under reduced pressure. Flash chromatography using ethyl acetate yielded 143 mg of 82 as a viscous oil. $R_f$ (ethyl acetate): 0.33 b) Example 99 cis-6-[4-(1-Amino-propyl)-4-(3-methanesulfonyl-phenyl)-cyclohexyloxy]-7-chloro-2H-isoquinolin-1-one

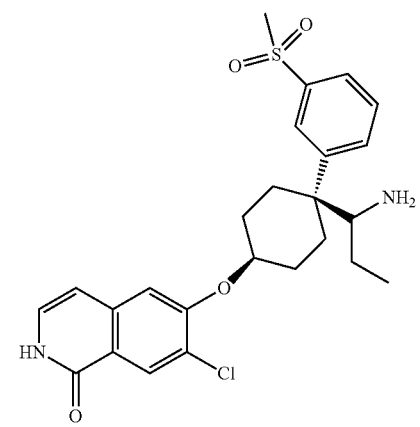 [SMILES: CCC(N)[C@]1(c2cccc(S(C)(=O)=O)c2)CC[C@H](Oc2cc3cc[nH]c(=O)c3cc2Cl)CC1]

140 mg (238 µmol) of cis-{1-[4-(7-Chloro-1-oxo-1,2-dihydro-isoquinolin-6-yloxy)-1-(3-methanesulfonyl-phenyl)-cyclohexyl]propyl-carbamic acid tert-butyl ester (82) were dissolved in 3 mL of isopropanol and 3 mL of a 2N aqueous solution of HCl added. The mixture was stirred for 20 h at ambient temperature, diluted with 30 mL of water and freeze dried to yield 120 mg of Example 99 as its hydrochloride as an amorphous solid. $R_t$=0.66 min (Method 18). Detected mass: 489.2 (M+H$^+$)

Example 100

6-[(1S,4S,5S)-5-(1-Amino-propyl)-5-phenyl-bicyclo[2.2.1]hept-2-yloxy]-7-chloro-2H-isoquinolin-1-one a) 5-Oxo-bicyclo[2.2.1]heptane-2-carbonitrile ethylene ketal (83)

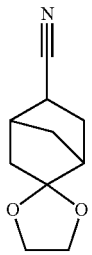

9.0 g (71 mmol) of 2-cyclopen-1-one ethylene ketal, 11.4 g (214 mmol) of acrylonitrile and 150 mg (1.4 mmol) of hydroquinone were mixed and heated to 150° C. for 1 h under microwave irradiation. The excess of acrylonitrile was removed under reduced pressure and the residue dissolved using 150 mL of diethylether. This solution was washed three times using 50 mL of saturated aqueous Na$_2$CO$_3$-solution each, dried over MgSO$_4$ and evaporated. The resulting oil was dissolved in 200 mL of cyclohexane and 100 mL of diethylether, washed three times using 50 mL of an aqueous 0.1 N NaOH-solution and twice using 100 mL of a saturated aqueous NaCl-solution. The organic layer was dried over MgSO$_4$, filtered and the solvent evaporated to yield 7.3 g of 83 as a colourless oil.

b) (1S,2S,4S)-5-Oxo-2-phenyl-bicyclo[2.2.1]heptane-2-carbonitrile ethylene ketal and (1R,2R,4R)-5-Oxo-2-phenyl-bicyclo[2.2.1]heptane-2-carbonitrile ethylene ketal (84 and 85)

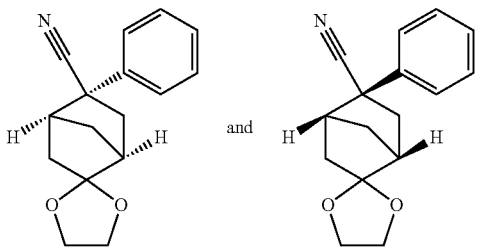 [SMILES: N#C[C@@]1(c2ccccc2)C[C@@H]2C[C@H]1CC21OCCO1 ; N#C[C@]1(c2ccccc2)C[C@H]2C[C@@H]1CC21OCCO1]

7.5 g (42 mmol) of 5-Oxo-bicyclo[2.2.1]heptane-2-carbonitrile ethylene ketal (83) and 4.4 g (46 mmol) of fluorobenzene were dissolved in 10 mL of anhydrous toluene. The mixture was stirred at 65° C. for 20 h, then poured into 300 mL of a saturated aqueous NaHCO$_3$-solution, and extracted twice using 100 mL ethyl acetate each. The organic layer was dried using MgSO$_4$ and evaporated. Chromatography on reversed phase (acetonitrile/water) yielded 3.4 g of the racemic mixture as a single diastereomer as colourless oil.

Chromatography on chiral phase (Chiralpak AD-H, 250× 4.6 mm) using n-heptane:2-propanol:methanol 5:1:1 yielded 1.4 g of 84 ($R_t$=7.4 min) and 1.4 g of 85 ($R_t$=9.3 min). $R_t$=1.44 min (Method 5). Detected mass: 256.3 (M+H$^+$)

The absolute stereochemistry was assigned arbitrarily.

c) (1S,2S,4S)-5-Oxo-2-phenyl-bicyclo[2.2.1]heptane-2-carbonitrile (86)

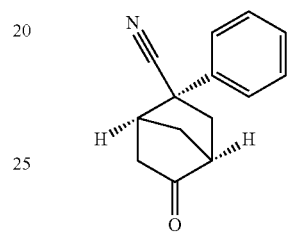

1.3 g of (1S,2S,4S)-5-Oxo-2-phenyl-bicyclo[2.2.1]heptane-2-carbonitrile ethylene ketal (84) were dissolved in a mixture of 30 mL THF and 30 mL of a 5% aqueous HCl-solution and kept at ambient temperature for 30 h. The mixture was diluted using 100 mL of a saturated aqueous NaCl-solution and 100 mL of ethyl acetate. After separation, the aqueous layer was extracted twice using 50 mL of ethyl acetate each. The organic layer was dried using MgSO$_4$ and evaporated to give 1.2 g of (86) as a colourless oil.

$[\alpha]_D$=+5.6° (c=0.013 in methanol), $R_t$=1.27 min (Method 5).

d) (1S,2S,4S)-5-Hydroxy-2-phenyl-bicyclo[2.2.1]heptane-2-carbonitrile (87)

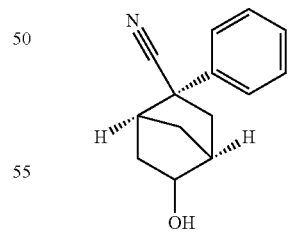

0.9 g (4.3 mmol) of (1S,2S,4S)-5-Oxo-2-phenyl-bicyclo[2.2.1]heptane-2-carbonitrile (86) were dissolved using 20 mL of ethanol and 161 mg (4.3 mmol) of NaBH$_4$ was added at −70° C. The mixture was stirred at ambient temperature for 1 h, 100 mL of a saturated aqueous NaCl-solution was added and the pH adjusted to 2-3 using aqueous HCl-solution. The mixture was extracted three times using 50 mL of ethyl acetate each. The organic layer was dried over MgSO$_4$ and evaporated to yield 0.9 g of (87) as a single diastereomer as a colourless oil. $R_f$=0.76 min (Method 18). Detected mass: 214.1 (M+H$^+$)

e) (1S,2S,4S)-5-(tert-Butyl-dimethyl-silanyloxy)-2-phenyl-bicyclo[2.2.1]heptane-2-carbonitrile (88)

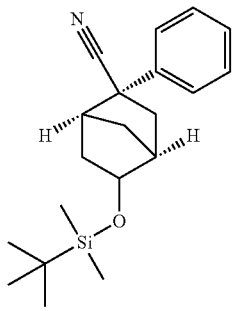 [SMILES: CC(C)(C)[Si](C)(C)OC1C[C@@H]2C[C@H]1C[C@@]2(C#N)c1ccccc1]

0.9 g (4.2 mmol) of (1S,2S,4S)-5-Hydroxy-2-phenyl-bicyclo[2.2.1]heptane-2-carbonitrile (87) and 1.1 g (10.6 mmol) of 2,6-lutidine were dissolved in 40 mL of dichloromethane. 1.3 g (5.1 mmol) of tert-butyldimethylsilyl trifluormethanesulfonate were added at −10° C. The mixture was stirred at ambient temperature for 17 h.

Afterwards, additional 500 mg of 2,6-lutidine and 600 mg of tert-butyldimethylsilyl trifluormethanesulfonate were added at −10° C. and the mixture stirred at ambient temperature for 48 h. Afterwards, additional 1.1 g of 2,6-lutidine and 1.3 g of tert-butyldimethylsilyl trifluormethanesulfonate were added at −10° C. and the mixture stirred at ambient temperature for 24 h. The mixture was evaporated, the residue dissolved using 100 mL of ethyl acetate and washed using three times 50 mL of a saturated aqueous Na$_2$CO$_3$-solution each, three times 50 mL of a 0.5 N aqueous HCl-solution each and finally once using 50 mL of a saturated aqueous Na$_2$CO$_3$-solution. The organic layer was dried using a mixture of MgSO$_4$ and K$_2$CO$_3$, filtered and evaporated. Flash chromatography on silica gel using ethyl acetate/n-heptane 1:2 yielded 970 mg of (88) as a colourless oil. $R_f$ (ethyl acetate/n-heptane 1:2)=0.8. $R_t$=1.32 min (Method 18).

f) (1S,4S,5S)-5-(1-Amino-propyl)-5-phenyl-bicyclo[2.2.1]heptan-2-ol (89)

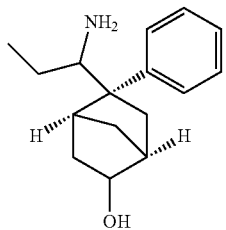 [SMILES: CCC(N)[C@@]1(c2ccccc2)C[C@@H]2C[C@H]1CC2O]

930 mg (2.8 mmol) of (1S,2S,4S)-5-(tert-Butyl-dimethyl-silanyloxy)-2-phenyl-bicyclo[2.2.1]heptane-2-carbonitrile (88) were dissolved in 10 mL of anhydrous toluene. Afterwards, 5.7 mL of a 1M solution of ethylmagnesium bromide in THF was added and the mixture was heated under reflux for 12 h. The mixture was then treated with 3 mL ethanol and evaporated. The residue was dissolved in 20 mL of ethanol and 215 mg (5.7 mmol) of NaBH$_4$ was added. The mixture was stirred at ambient temperature for 3 h and then evaporated. The residue was dissolved using 100 mL of water, the pH adjusted to 3 using aqueous HCl-solution to remove excess NaBH$_4$ and then adjusted to pH=12 using saturated aqueous Na$_2$CO$_3$-solution. The mixture was extracted three times using 30 mL of t-butylmethylether each. Afterwards, the organic layer was extracted twice using 20 mL of a 1N aqueous HCl-solution each, the aqueous layer was adjusted to pH>11 using saturated aqueous Na$_2$CO$_3$-solution and extracted three times using 30 mL t-butylmethylether each. The organic layer was dried using MgSO$_4$ and evaporated yielding 200 mg of the desired product 89, used without further purification. $R_t$=0.58 min (Method 18).

g) 1-[(1S,2S,4S)-5-(7-Chloro-1-methoxy-isoquinolin-6-yloxy)-2-phenyl-bicyclo[2.2.1]hept-2-yl]-propylamine (90)

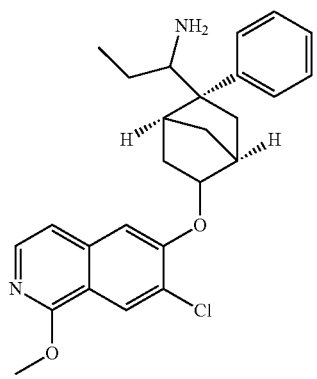 [SMILES: CCC(N)[C@@]1(c2ccccc2)C[C@@H]2C[C@H]1CC2Oc1cc2ccnc(OC)c2cc1Cl]

200 mg (0.82 mmol) of (1S,4S,5S)-5-(1-Amino-propyl)-5-phenyl-bicyclo[2.2.1]heptan-2-ol (89) were dissolved in 5 mL anhydrous dimethylacetamide. Afterwards, 39 mg (1.63 mmol) of NaH were added, followed by the addition of 173 mg (0.82 mmol) of 7-chloro-6-fluoro-1-methoxy-isoquinoline (10). The mixture was stirred at ambient temperature for 20 h. Afterwards, 50 mL of a saturated aqueous NaHCO$_3$-solution were added and the mixture extracted three times using 30 mL ethyl acetate each. The organic layer was dried using MgSO$_4$ and evaporated. The residue was purified using chromatography on reversed phase (acetonitrile/water). The product-containing fractions were evaporated to half of the original volume, 10 mL of a saturated aqueous Na$_2$CO$_3$-solution was added and the mixture extracted three times using 20 mL of ethyl acetate each. The organic layer was dried using MgSO$_4$, filtered and evaporated yielding 34 mg of the desired product 90. $R_t$=0.86 min (Method 18). Detected mass: 437.3 (M+H$^+$)

h) 6-[(1S,4S,5S)-5-(1-Amino-propyl)-5-phenyl-bicyclo[2.2.1]hept-2-yloxy]-7-chloro-2H-isoquinolin-1-one (Example 100)

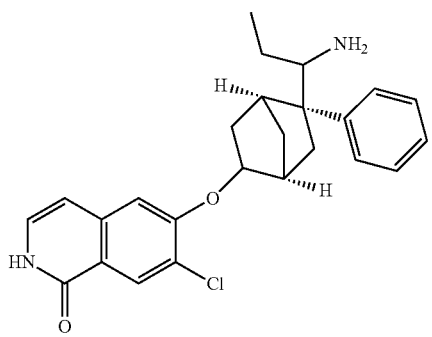 [SMILES: CCC(N)[C@@]1(c2ccccc2)C[C@@H]2C[C@H]1CC2Oc1cc2cc[nH]c(=O)c2cc1Cl]

35 mg of 1-[(1S,2S,4S)-5-(7-Chloro-1-methoxy-isoquinolin-6-yloxy)-2-phenyl-bicyclo[2.2.1]hept-2-yl]-propylamine (90) were dissolved using 1 mL of 2-propanol and 1 mL of a 1N aqueous HCl-solution. The mixture was heated to 100° C. for 1 h under microwave irradiation. Afterwards, 20 mL of water were added and the mixture freeze dried. The residue was once again treated with 20 mL of water and freeze dried to yield 34 mg of the desired product as its hydrochloride. $R_t$=0.75 min (Method 18). Detected mass: 423.2 (M+H$^+$)

Example 101

6-[(1R,4R,5R)-5-(1-Amino-propyl)-5-phenyl-bicyclo[2.2.1]hept-2-yloxy]-7-chloro-2H-isoquinolin-1-one

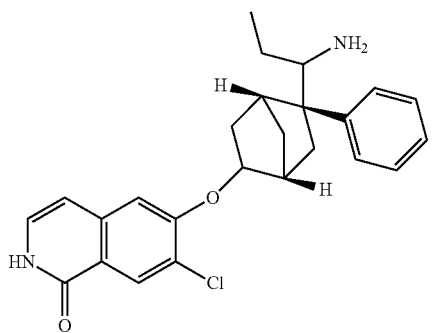 [SMILES: CCC(N)[C@]1(c2ccccc2)C[C@H]2C[C@@H]1CC2Oc1cc2cc[nH]c(=O)c2cc1Cl]

Example 101 has been synthesized as its hydrochloride in analogy to the synthesis of example 100 starting from 7-chloro-6-fluoro-1-methoxy-isoquinoline (10) and (1R,2R,4R)-5-oxo-2-phenyl-bicyclo[2.2.1]heptane-2-carbonitrile ethylene ketal (85). $R_t$=0.75 min (Method 18). Detected mass: 423.2 (M+H$^+$)

Example 102 cis-6-[4-(1-Benzylamino-propyl)-4-phenyl-cyclohexyloxy]-7-methyl-2H-isoquinolin-1-one

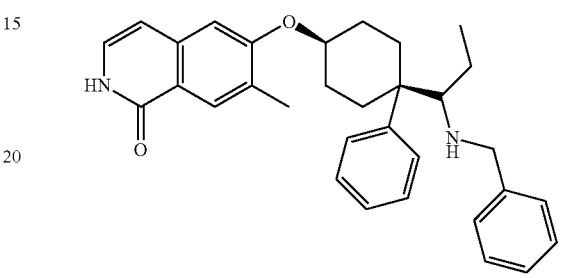

60 mg of Example 11 were dissolve in 850 μL of methanol, then 39 μL of triethylamine, 80 μL of acetic acid, 50 mg of powdered molecular sieves and 43 μL of benzaldehyde were added and the mixture was allowed to stir for 1 h. A solution of 26 mg of sodium cyanoborohydride in 200 μL of methanol was added and the mixture was stirred at 40° C. for 5 min. The reaction mixture was filtered and the filtrate was evaporated to dryness. The residue was dissolved in 50 mL of dichloromethane and washed with saturated sodium bicarbonate solution. The aqueous phase was reextracted twice with dichloromethane. The combined organic layer was dried over magnesium sulphate, filtered, evaporated and the crude material was purified by reversed phase HPLC (acetonitrile/water) to yield 27 mg of the desired product as trifluoroacetic acid salt. $R_t$=2.94 min (Method 2). Detected mass: 481.4 (M+H$^+$).

The following examples were obtained in a similar fashion as described for example 102, using the respective isoquinolines and aldehydes as starting materials:

| Ex. No. | Product | Start. Mat. | Aldehyde | Chemical Name | [M + H$^+$] | $R_t$ [min] | Method |
|---|---|---|---|---|---|---|---|
| 103 |  | Ex. 11 | Acetaldehyde | cis-6-[4-(1-Diethylamino-propyl)-4-phenyl-cyclohexyloxy]-7-methyl-2H-isoquinolin-1-one | 447.4 | 2.73 | 2 |

| Ex. No. | Product | Start. Mat. | Aldehyde | Chemical Name | [M + H⁺] | R₁/[min] | Method |
|---|---|---|---|---|---|---|---|
| 104 | | Ex. 86 | Propanal | cis-7-Methyl-6-[4-(1-propyl amino-propyl)-4-(3-trifluoro methyl-phenyl)-cyclo hexyloxy]-2H-isoquinolin-1-one | 501.2 | 1.50 | 10 |
| 105 | | Ex. 3 | Benz-aldehyde | cis-6-[4-(1-Benzylamino-propyl)-4-phenyl-cyclohexyloxy]-7-chloro-2H-isoquinolin-1-one | 501.3 | 1.47 | 10 |
| 106 | | Ex. 3 | Iso-butyr-aldehyde | cis-7-Chloro-6-[4-(1-isobutyl amino-propyl)-4-phenyl-cyclohexyloxy]-2H-iso quinolin-1-one | 467.3 | 1.45 | 10 |
| 107 | | Ex. 3 | Buta-nal | cis-6-[4-(1-Butylamino-propyl)-4-phenyl-cyclo hexyloxy]-7-chloro-2H-isoquinolin-1-one | 501.3 | 1.46 | 10 |

| Ex. No. | Product | Start. Mat. | Aldehyde | Chemical Name | [M + H⁺] | $R_t$/ [min] | Method |
|---|---|---|---|---|---|---|---|
| 108 | 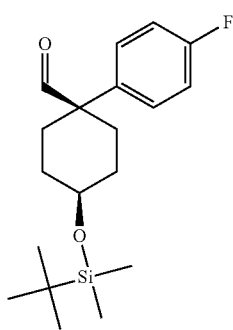 [SMILES: CC(C)(C)[Si](C)(C)O[C@H]1CC[C@](C=O)(c2ccc(F)cc2)CC1] | Ex. 3 | Cyclopropyl carbox aldehyde | cis-7-Chloro-6-{4-[1-(cyclopropylmethyl-amino)-propyl]-4-phenyl-cyclohexyloxy}-2H-isoquinolin-1-one | 465.3 | 1.43 | 10 | cis-4-(tert-Butyl-dimethyl-silanyloxy)-1-(4-fluoro-phenyl)-cyclohexanecarb-aldehyde (91)

To a solution of 9.74 g (29.2 mmol) of cis-4-(tert-butyl-dimethyl-silanyloxy)-1-(4-fluoro-phenyl)-cyclohexane-carbonitrile (78) in 290 mL of dichloromethane at −70° C. were added over a period of 20 min 73 mL (73 mmol) of a solution of diisobutylaluminium hydride in dichloromethane (1M). The reaction mixture was stirred for 1 h at −70° C., before 250 mL of 10% aqueous potassium sodium tartrate solution were added and the resulting biphasic system was vigourously stirred for 2 h at room temperature. 200 mL of ethyl acetate were added and the phases were separated. The aqueous phase was extracted with 150 mL of ethyl acetate and the combined organic phases were dried over magnesium sulphate, filtered and concentrated. The resulting oil was purified by silica gel chromatography (heptanes:ethyl acetate) to give 8.38 g of the desired product. $R_t$=1.09 min (Method 17). Detected mass: 337.2 (M+H⁺).

cis-[4-(tert-Butyl-dimethyl-silanyloxy)-1-(4-fluoro-phenyl)-cyclohexyl]-acetonitrile (92)

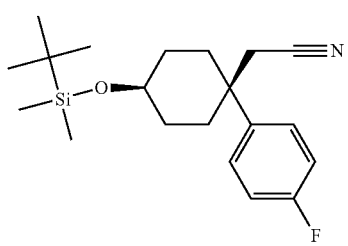 [SMILES: CC(C)(C)[Si](C)(C)O[C@H]1CC[C@](CC#N)(c2ccc(F)cc2)CC1]

To an ice-cold solution of 6.60 g (19.6 mmol) of cis-4-(tert-butyl-dimethyl-silanyloxy)-1-(4-fluoro-phenyl)cyclohexanecarbaldehyde (91) in 50 mL of dry methanol were added portionwise 1.48 g (39.2 mmol) of sodium borohydride. The reaction mixture was stirred for 1 h at 0° C., then 16 h at room temperature, before being quenched by addition of 70 mL of water. The solution was extracted three times with ethyl acetate (100 mL each). The organic phases were combined, washed with brine, dried over magnesium sulphate, filtered and evaporated to dryness.

The resulting alcohol (6.17 g crude) was dissolved in 50 mL of dry dichloromethane and cooled to 0° C. 2.56 mL (1.84 g, 18.2 mmol) of triethylamine were added and the mixture stirred for 5 min. Then, 3.53 mL (5.22 g, 45.6 mmol) of methanesulfonylchloride was added dropwise and the solution was stirred for 2.5 h at 0° C. The reaction mixture was treated with 50 mL of water and stirred for 30 min at room temperature. The phases were separated and the aqueous phase was extracted twice with 100 mL dichloromethane. The organic phases were combined, washed with brine, dried over magnesium sulphate, filtered and evaporated to dryness. The crude product was purified by silica gel chromatography (heptanes:ethyl acetate) to give 5.20 g of the desired mesylate, which was dissolved in 200 mL of dry dimethylformamide and treated with 4.06 g (62.4 mmol) of potassium cyanide and 6.60 g (25.0 mmol) of 18-crown-6. The orange solution was heated to 155° C. for 36 h and stirred 16 h at room temperature before being poured onto 200 mL of a mixture of water and ice. The mixture was extracted twice with ethyl acetate. The organic phases were combined, dried over magnesium sulphate, filtered and concentrated. The crude product was purified by silica gel chromatography (heptanes:ethyl acetate) to give 1.22 g of the desired product 92. $R_t$=1.04 min (Method 17). Detected mass: 348.2 (M+H⁺).

cis-4-(2-Amino-propyl)-4-(4-fluoro-phenyl)-cyclohexanol (93)

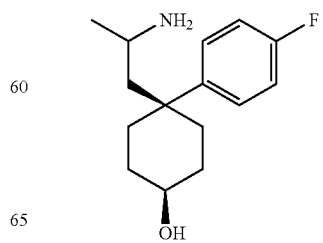

Under argon, 260 mg (0.75 mmol) of cis-[4-(tert-butyl-dimethyl-silanyloxy)-1-(4-fluoro-phenyl)-cyclohexyl]-acetonitrile (92) were dissolved in 5 mL of absolute toluene. Then, 500 µL of methylmagnesium bromide (3M in diethylether) were added dropwise and the reaction mixture was heated to 80° C. for 2 h. After cooling to room temperature, 3 mL of dry methanol were added. After a period of 10 min, 28.3 mg (1.45 mmol) of sodium borohydride were added and the mixture was stirred for 3 h at room temperature. The reaction was quenched by addition of 1M aqueous sodium hydroxide solution and extracted three times with diethylether (100 mL each).

The combined organic phases were concentrated to a volume of approximately 80 mL and 50 mL of 2N aqueous hydrochloric acid were added. The biphasic system was stirred vigourously at room temperature for 3 h. The phases were separated, the aqueous layer was adjusted to pH 12 by addition of 5N sodium hydroxide solution and extracted three times with a 3:1 mixture of dichloromethane and 2-propanol (80 mL each). The combined organic layers were evaporated to give 92 mg of the desired product, which was used directly in the next step. $R_f$=0.64 min (Method 18). Detected mass: 252.2 (M+H$^+$).

cis-4-(2-Amino-butyl)-4-(4-fluoro-phenyl)-cyclohexanol (94)

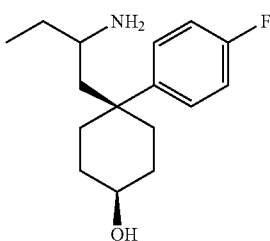 [SMILES: CCC(N)C[C@]1(c2ccc(F)cc2)CC[C@H](O)CC1]

355 mg of cis-4-(2-Amino-butyl)-4-(4-fluoro-phenyl)-cyclohexanol (94) were prepared analoguosly to the preparation of cis-4-(2-amino-propyl)-4-(4-fluoro-phenyl)-cyclohexanol (93), starting from 500 mg (1.44 mmol) of cis-[4-(tert-butyl-dimethyl-silanyloxy)-1-(4-fluoro-phenyl)-cyclohexyl]acetonitrile (92), 960 µL (2.88 mmol) of ethylmagnesium bromide (3M in diethylether) and 54.4 mg (2.88 mmol) of sodium borohydride. $R_f$=0.66 min (Method 18). Detected mass: 266.2 (M+H$^+$).

Example 109 cis-6-[4-(2-Amino-propyl)-4-(4-fluoro-phenyl)-cyclohexyloxy]-7-chloro-2H-isoquinolin-1-one

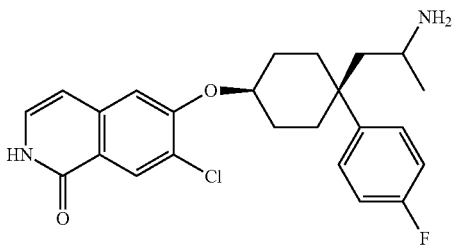 [SMILES: CC(N)C[C@]1(c2ccc(F)cc2)CC[C@H](Oc2cc3cc[nH]c(=O)c3cc2Cl)CC1]

Example 109 was synthesized using the reaction sequence as described for the synthesis of Example 1. 90 mg of cis-4-(2-amino-propyl)-4-(4-fluoro-phenyl)-cyclohexanol (93) and 79.6 mg of 7-chloro-6-fluoro-1-methoxy-isoquinoline (10) were used to give 35 mg of Example 109 as hydrochloride. $R_f$=1.31 min (Method 16). Detected mass: 429.2 (M+H$^+$).

Example 110 cis-6-[4-(2-Amino-butyl)-4-(4-fluoro-phenyl)-cyclohexyloxy]-7-chloro-2H-isoquinolin-1-one

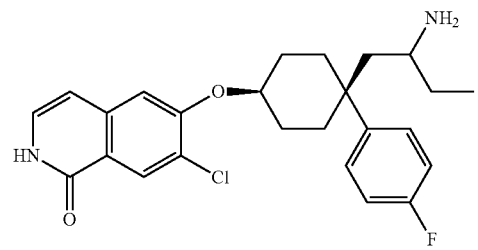 [SMILES: CCC(N)C[C@]1(c2ccc(F)cc2)CC[C@H](Oc2cc3cc[nH]c(=O)c3cc2Cl)CC1]

Example 110 was obtained as hydrochloride following the reaction sequence as used for the synthesis of Example 109, starting from cis-4-(2-amino-butyl)-4-(4-fluoro-phenyl)-cyclohexanol (94) and 7-chloro-6-fluoro-1-methoxy-isoquinoline (10). $R_f$=1.45 min (Method 16). Detected mass: 443.2 (M+H$^+$).

tert-Butyl-(7-chloro-6-fluoro-isoquinolin-1-yl)-amine (95)

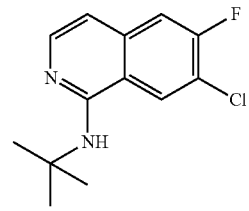 [SMILES: CC(C)(C)Nc1nccc2cc(F)c(Cl)cc12]

A solution of 5.0 g (25.3 mmol) of 7-chloro-6-fluoro-isoquinoline-2-oxide (9) in 120 mL of benzotrifluoride was treated with 15.9 mL (11.1 g, 152 mmol) of tert-butylamine and cooled to 0° C. Then, 17.3 g (53.1 mmol) of p-toluenesulfonic anhydride were added portionwise with temperature control (<10° C.). The reaction mixture was stirred at room temperature for 16 h, before being cooled to 0° C. and another 8.0 mL (76.1 mmol) of tert-butylamine and 8.26 g (25.3 mmol) of p-toluenesulfonic anhydride were added. The reaction mixture was stirred for 24 h at room temperature, then concentrated and partitioned between 120 mL of water and 150 mL of dichloromethane. The phases were separated and the organic phase was washed eight times with 3N aqueous sodium hydroxide, to extract excess p-toluenesulfonic acid, dried over magnesium sulphate, filtered and evaporated to dryness. The crude product was purified twice by silica gel chromatography (dichloromethane:methanol) to give 277 mg of pure desired product (95) and 714 mg of the product slightly contaminated with p-toluenesulfonic acid. $R_t$=2.35 min (Method 2). Detected mass: 253.1 (M+H$^+$).

Example 111 cis-6-[4-(1-Amino-propyl)-4-phenyl-cyclohexyloxy]-7-chloro-isoquinolin-1-ylamine

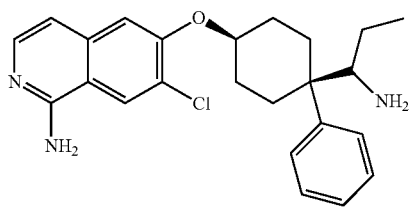 [SMILES: CCC(N)[C@]1(c2ccccc2)CC[C@H](Oc2cc3ccnc(N)c3cc2Cl)CC1]

58 mg of Example 111 were obtained following a reaction sequence with NaH-mediated coupling and acidic deprotection in the microwave similar to the one used for the synthesis of Example 1, starting from 102 mg (0.44 mmol) of cis-4-(1-aminopropyl)-4-phenylcyclohexanol (6) and 100 mg (0.40 mmol) of tert-butyl-(7-chloro-6-fluoro-isoquinolin-1-yl)-amine (95). $R_t$=0.84 min (Method 11). Detected mass: 410.3 (M+H$^+$).

{1-[8-(4-Methoxy-phenyl)-1,4-dioxa-spiro[4.5]dec-8-yl]-propyl}-carbamic acid benzyl ester (96)

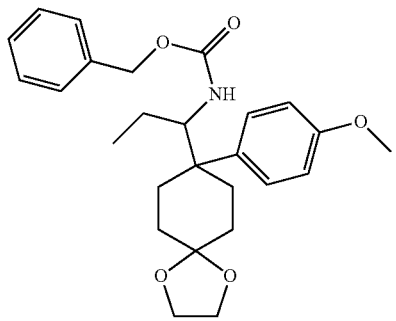 [SMILES: CCC(NC(=O)OCc1ccccc1)C1(c2ccc(OC)cc2)CCC2(CC1)OCCO2]

5.0 g (18.3 mmol) of 8-(4-methoxy-phenyl)-1,4-dioxa-spiro[4.5]decane-8-carbonitrile (synthesized from 1-(4-methoxy-phenyl)-4-oxo-cyclohexanecarbonitrile in a similar fashion as described for 15) were dissolved in 20 mL of absolute toluene. Then, 12.2 mL (36.6 mmol) of ethylmagnesium chloride (3M in THF) were added dropwise and the reaction mixture was heated to 90° C. for 5 h. After cooling to −15° C., 10 mL of dry methanol were added. After a period of 10 min, 1.37 g (36.3 mmol) of sodium borohydride were added portionwise at 0° C. and the mixture was stirred for 16 h at room temperature. The reaction was quenched by addition of 1M aqueous sodium hydroxide solution (100 mL) and extracted three times with diethylether (150 mL each). The combined organic phases were dried over magnesium sulphate, filtered and the solvent evaporated.

The crude amine (4.90 g) was dissolved in 55 mL of dry dichloromethane, cooled to −78° C. and 2.46 mL (1.79 g, 17.6 mmol) of triethylamine and 2.71 mL (2.74 g, 16.0 mmol) of benzylchloroformate were added. The reaction mixture was warmed to room temperature and stirred for 2 h. Then, 100 mL of water were added and the mixture was extracted three times with ethyl acetate. The combined organic phases were dried over magnesium sulphate, filtered and concentrated to give the crude product (96), which was used directly in the next step. $R_t$=1.09 min (Method 18). Detected mass: 440.4 (M+H$^+$).

{1-[1-(4-Methoxy-phenyl)-4-oxo-cyclohexyl]-propyl}-carbamic acid benzyl ester (97)

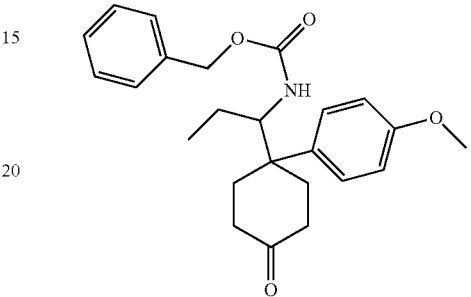

534 mg of {1-[8-(4-Methoxy-phenyl)-1,4-dioxa-spiro[4.5]dec-8-yl]-propyl}-carbamic acid benzyl ester (96) were dissolved in 1 mL of a 2:1 mixture of acetone and 6N aqueous hydrochloric acid. The reaction mixture was stirred for 16 h at room temperature, then dropped into 150 mL of saturated aqueous sodium bicarbonate solution. The phases were separated and the aqueous phase was extracted three times with dichloromethane (100 mL each). The combined organic phases were dried over magnesium sulphate, filtered and concentrated to give the ketone 97. $R_t$=1.58 min (Method 19). Detected mass: 396.3 (M+H$^+$).

{1-[4-Amino-1-(4-methoxy-phenyl)-cyclohexyl]-propyl}carbamic acid benzyl ester (98)

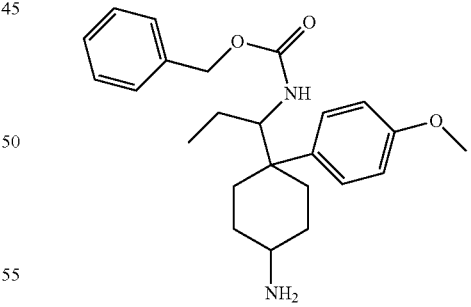

200 mg (0.51 mmol) of the ketone (97) were dissolved in 1.5 mL of absolute methanol, then 390 mg (5.06 mmol) of ammonium acetate and 31.8 mg (0.51 mmol) of sodium cyanoborohydride were added, and the mixture was stirred at room temperature for 2 h. The reaction mixture was evaporated, the residue dissolved in 50 mL of 1N aqueous sodium hydroxide and extracted twice with 100 mL of dichloromethane. The combined organic layer was dried over magnesium sulphate, filtered, and evaporated to give 150 mg of the title compound 98 in a purity sufficient to be used directly in the next step. $R_t$=1.18 min (Method 19). Detected mass: 397.3 (M+H$^+$).

{1-[4-(Isoquinolin-6-ylamino)-1-(4-methoxy-phenyl)-cyclohexyl]-propyl}-carbamic acid benzyl ester (99)

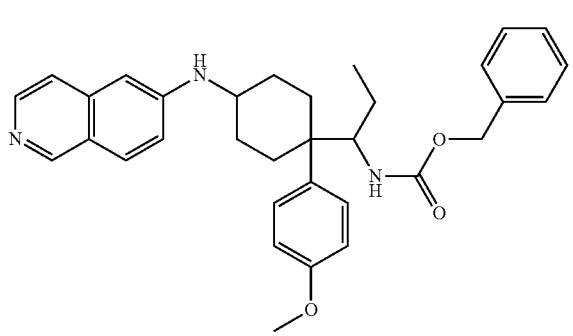 [SMILES: CCC(NC(=O)OCc1ccccc1)C1(c2ccc(OC)cc2)CCC(Nc2ccc3cnccc3c2)CC1]

In 1 mL of absolute toluene were dissolved 66.0 mg (0.32 mmol) of 6-bromo-isoquinoline, 151 mg (380 µmol) of {1-[4-amino-1-(4-methoxy-phenyl)-cyclohexyl]-propyl}-carbamic acid benzyl ester (98), and 155 mg (476 µmol) of cesium carbonate. The solution was degassed twice, then 2.14 mg (9.5 µmol) of palladium acetate and 8.89 mg (14.3 µmol) of 2,2'-bis(diphenylphosphino)-1,1'-binaphthyl were added and the reaction mixture was heated to 100° C. until complete conversion could be observed. The mixture was evaporated, then redissolved in 50 mL of dichloromethane and washed twice with 50 mL of saturated aqueous sodium bicarbonate solution. The organic phase was dried over magnesium sulphate, filtered, concentrated and purified by silica gel chromatography (dichloromethane:methanol) to give 48 mg of the pure desired product. $R_t$=1.38 min (Method 19). Detected mass: 524.4 (M+H$^+$).

Example 112

[4-(1-Amino-propyl)-4-(4-methoxy-phenyl)-cyclohexyl]-isoquinolin-6-yl-amine

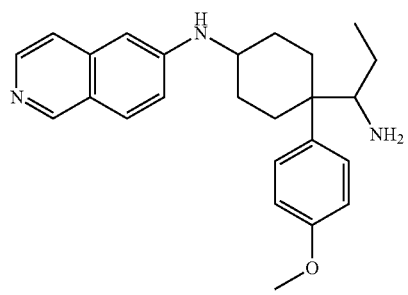 [SMILES: CCC(N)C1(c2ccc(OC)cc2)CCC(Nc2ccc3cnccc3c2)CC1]

48 mg (91.7 µmol) of {1-[4-(Isoquinolin-6-ylamino)-1-(4-methoxy-phenyl)-cyclohexyl]-propyl}-carbamic acid benzyl ester (99) were dissolved in 300 µL of dry methanol and 9.7 µg of palladium on activated charcoal (10%) were added. The mixture was stirred under a hydrogen atmosphere until conversion was complete. The catalyst was filtered off and the reaction mixture was evaporated to dryness to give the title compound. $R_t$=0.89 min (Method 19). Detected mass: 390.3 (M+H$^+$).

1-(Di-tert-butyloxycarbonyl)-amino-[4-(1-amino-propyl)-4-(4-methoxy-phenyl)-cyclohexyl]-isoquinolin-6-yl-amine (100)

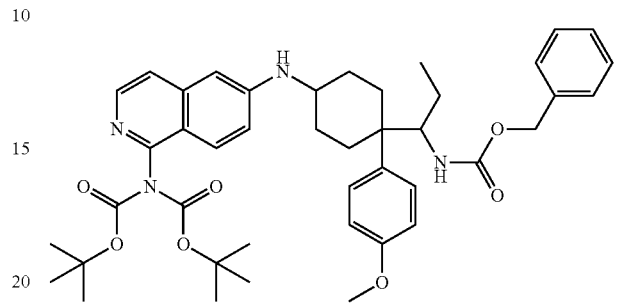

30 mg (83.5 µmol) of 1-(di-tert-butyloxycarbonyl)-amino-isoquinolin-6-amine were dissolved in 135 µL of abs. methanol, then 23 µL (16.9 mg, 167 µmol) of triethylamine, 47.7 µL (50.1 mg, 835 µmol) of acetic acid, 20 mg of powdered molecular sieves and 99 mg (250 µmol) of (97) were added and the mixture was allowed to stir for 1 h. A solution of 15.7 mg (250 µmol) of sodium cyanoborohydride in 50 µL of methanol was added and the mixture was stirred at 70° C. for 10 h. Then, another 50 mg (125 µmol) of (97) followed by a portion of 15.7 mg (250 µmol) of sodium cyanoborohydride in 50 µL of methanol were added and the mixture was allowed to stir for 1 h at 70° C. The reaction mixture was filtered and the filtrate was evaporated to dryness. The residue was dissolved in 50 mL of dichloromethane and washed with saturated sodium bicarbonate solution. The aqueous phase was reextracted three times with dichloromethane. The combined organic layer was dried over magnesium sulphate, filtered, evaporated and the crude material was purified by reversed phase HPLC (acetonitrile/water) to yield 5 mg of the desired product as trifluoroacetic acid salt. $R_t$=1.65 min (Method 19). Detected mass: 739.3 (M+H$^+$).

Example 113

1-Amino-[4-(1-amino-propyl)-4-(4-methoxy-phenyl)-cyclohexyl]-isoquinolin-6-yl-amine

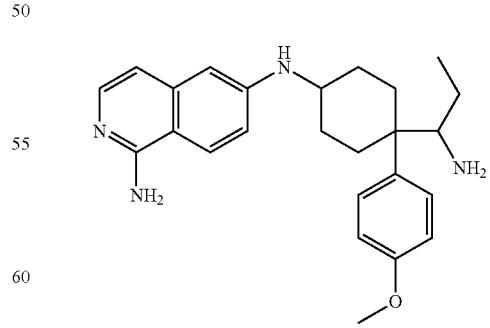

5 mg (6.77 µmol) of 1-(Di-tert-butyloxycarbonyl)-amino-[4-(1-amino-propyl)-4-(4-methoxy-phenyl)-cyclohexyl]-isoquinolin-6-yl-amine (100) were dissolved in 500 µL of dry methanol and 5.0 mg of palladium on activated charcoal (10%) were added. The mixture was stirred under a hydrogen atmosphere until conversion was complete. The catalyst was filtered off and the reaction mixture was evaporated to dryness. The solid residue was treated with 500 μL of 4N hydrochloric acid in dioxane and stirred at room temperature until complete deprotection could be observed. The reaction mixture was evaporated, water was added and the mixture was lyophilized. The residue was taken up in water and lyophilized again to give 1.2 mg of the desired product as hydrochloride. Rt=0.98 min (Method 19). Detected mass: 405.3 (M+H$^+$).

cis-2-Methyl-propane-2-sulfinic acid 1-[4-(tert-butyl-dimethyl-silanyloxy)-1-(4-fluoro-phenyl)-cyclohexyl]-methylideneamide (101)

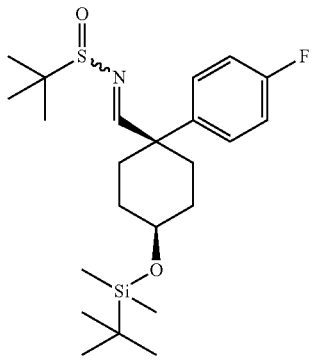 [SMILES: CC(C)(C)S(=O)N=C[C@]1(c2ccc(F)cc2)CC[C@H](O[Si](C)(C)C(C)(C)C)CC1]

To a solution of 3.0 g (8.92 mmol) of cis-4-(tert-butyl-dimethyl-silanyloxy)-1-(4-fluoro-phenyl)-cyclohexanecarbaldehyde (91) in 26 mL of tetrahydrofuran were added 1.19 g (9.81 mmol) of 2-methyl-2-propanesulfinamide and 4.31 mL (4.69 g, 13.4 mmol) of titanium(IV) ethoxide. The resulting mixture was stirred for 16 h under reflux, before being treated with 30 mL of water. The resulting suspension was filtered through celite. The filter cake was rinsed with 200 mL of ethyl acetate and 60 mL of water. The phases were separated and the aqueous layer was extracted with ethyl acetate. The combined organic layers were dried over magnesium sulphate, filtered, and concentrated in vacuo. The crude product was purified by flash chromatography (SiO$_2$, 0%→100% ethyl acetate in heptane) to yield 1.64 g of the title compound (101). R$_t$=1.15 min (Method 17). Detected mass: 440.2 (M+H$^+$).

cis-2-Methyl-propane-2-sulfinic acid {2-benzenesulfonyl-1-[4-(tert-butyl-dimethyl-silanyloxy)-1-(4-fluoro-phenyl)-cyclohexyl]-2-fluoro-ethyl}-amide (102)

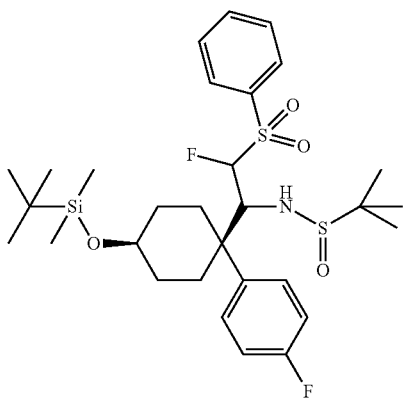 [SMILES: CC(C)(C)S(=O)NC(C(F)S(=O)(=O)c1ccccc1)[C@]1(c2ccc(F)cc2)CC[C@H](O[Si](C)(C)C(C)(C)C)CC1]

A solution of 1.75 g (3.98 mmol) of cis-2-methyl-propane-2-sulfinic acid 1-[4-(tert-butyl-dimethyl-silanyloxy)-1-(4-fluoro-phenyl)-cyclohexyl]-methylideneamide (101) and 693 mg (3.98 mmol) of fluoromethyl-phenyl-sulfone in 40 mL of dry tetrahydrofuran was cooled to −78° C. and 4.17 mL (4.17 mmol) of a 1M solution of lithium bis(trimethylsilyl)amide in tetrahydrofuran were added. The mixture was stirred for 1 h at −78° C. before being quenched by addition of saturated aqueous ammonium chloride solution and extracted twice with ethyl acetate. The combined organic layers were dried over magnesium sulphate, filtered, and concentrated in vacuo to give 2.45 g of the crude title compound (102) as diastereomeric mixture. R$_t$=3.31 min (Method 12). Detected mass: 614.3 (M+H$^+$)

cis-2-Methyl-propane-2-sulfinic acid {1-[4-(tert-butyl-dimethyl-silanyloxy)-1-(4-fluoro-phenyl)-cyclohexyl]-2-fluoro-ethyl}-amide (103)

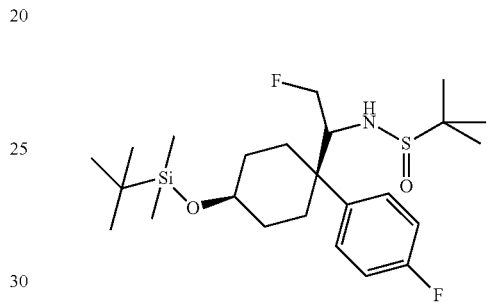

1.70 g (2.77 mmol) of cis-2-Methyl-propane-2-sulfinic acid {2-benzenesulfonyl-1-[4-(tert-butyl-dimethyl-silanyloxy)-1-(4-fluoro-phenyl)-cyclohexyl]-2-fluoro-ethyl}-amide (102) was dissolved in 30 mL of dry methanol and 1.57 g (11.1 mmol) of dibasic sodium phosphate were added. The suspension was cooled to −20° C., and treated with 2.48 g of sodium mercury amalgam (5% mercury). The reaction mixture was stirred at 0° C. for 16 h and another 620 mg of sodium amalgam were added. After stirring for 24 h at room temperature, the solution was decanted from the solids, evaporated to dryness and the residue partitioned between 50 mL of brine and 100 mL of diethylether. The organic layer was dried over sodium sulphate, filtered and concentrated in vacuo. Purification by flash chromatography (SiO$_2$, 0%→100% ethyl acetate in heptane) yielded 300 mg of the title compound (103). R$_t$=1.07 min (Method 17). Detected mass: 474.4 (M+H$^+$).

cis-4-(1-Amino-2-fluoro-ethyl)-4-(4-fluoro-phenyl)cyclohexanol (104)

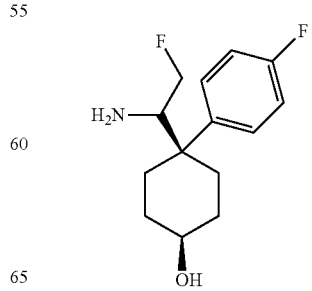

A solution of 300 mg (0.63 mmol) of cis-2-methyl-propane-2-sulfinic acid {1-[4-(tert-butyl-dimethyl-silanyloxy)-1-(4-fluoro-phenyl)-cyclohexyl]-2-fluoro-ethyl}-amide (103) in 3 mL of 2-propanol was treated with 3 mL of 6N aqueous hydrochloric acid and stirred for 18 h at room temperature. The mixture was washed with 50 mL of diethylether and lyophilized, then taken up in water and lyophilized again to give the title compound (104) as its hydrochloride. $R_t$=0.49 min (Method 18). Detected mass: 256.3 (M+H$^+$).

Example 114 cis-6-[4-(1-Amino-2-fluoro-ethyl)-4-(4-fluoro-phenyl)-cyclohexyloxy]-7-chloro-2H-isoquinolin-1-one

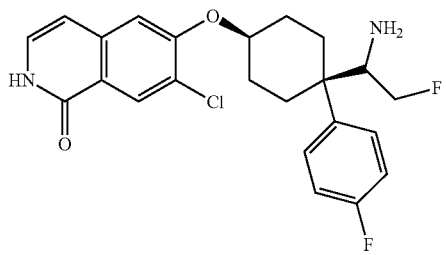 [SMILES: NC(CF)[C@]1(c2ccc(F)cc2)CC[C@H](Oc2cc3cc[nH]c(=O)c3cc2Cl)CC1]

Example 114 was synthesized using the reaction sequence as described for the synthesis of Example 1. 209 mg of cis-4-(1-amino-2-fluoro-ethyl)-4-(4-fluoro-phenyl)-cyclohexanol (104) and 158 mg of 7-chloro-6-fluoro-1-methoxy-isoquinoline (10) were used to give 132 mg of Example 114 as its hydrochloride. $R_t$=1.79 min (Method 12). Detected mass: 433.2 (M+H$^+$)

2-Methyl-propane-2-sulfinic acid 8-(4-fluoro-phenyl)-1,4-dioxa-spiro[4.5]dec-8-ylmethyleneamide (105)

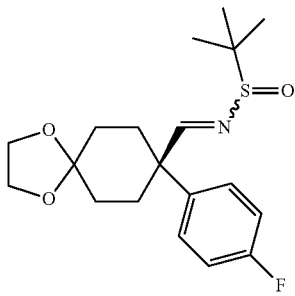

To a solution of 10.0 g (38.3 mmol) of 8-(4-fluoro-phenyl)-1,4-dioxa-spiro[4.5]decane-8-carbonitrile (15) in 44 mL of tetrahydrofuran at −78° C. were slowly added 76.5 mL (76.5 mmol) of a 1M solution of diisobutylaluminium hydride in toluene and the reaction was allowed to warmed to 0° C. over a period of 3 h. The mixture was recooled to −78° C., neutralized by dropwise addition of a 10% aqueous citric acid solution and warmed to room temperature over 15 h. The mixture was extracted three times with methyl-tert.butyl ether (50 mL each), the combined organics were dried over magnesium sulphate, filtered and evaporated to give 8-(4-fluoro-phenyl)-1,4-dioxa-spiro[4.5]decane-8-carbaldehyde-carbaldehyde.

The crude aldehyde was dissolved in 113 mL of tetrahydrofuran and 5.09 g (42.0 mmol) of 2-methyl-2-propanesulfinamide and 12.0 mL (13.1 g, 57.3 mmol) of titanium(IV) ethoxide were added. The resulting mixture was stirred for 3 h under reflux and 16 h at room temperature, before being treated with 30 mL of water and filtered through celite. The filter cake was washed with 200 mL of ethyl acetate and 60 mL of water, the phases were separated and the aqueous layer was extracted twice with ethyl acetate. The combined organic layers were dried over magnesium sulphate, filtered, and concentrated in vacuo. The crude product was purified by flash chromatography (SiO$_2$, 0%→100% ethyl acetate in heptane) to yield 3.20 g of the title compound (105). $R_t$=1.01 min (Method 18). Detected mass: 368.3 (M+H$^+$).

2-Methyl-propane-2-sulfinic acid {1-[8-(4-fluoro-phenyl)-1,4-dioxa-spiro[4.5]dec-8-yl]-allyl}-amide (106)

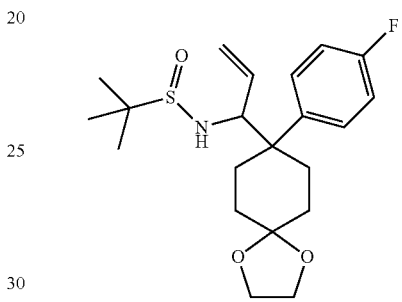

Under argon, 2.00 g (5.44 mmol) of 2-methyl-propane-2-sulfinic acid 8-(4-fluoro-phenyl)-1,4-dioxa-spiro[4.5]dec-8-ylmethyleneamide (105) were dissolved in 27 mL of absolute tetrahydrofuran. Then, 5.99 mL (5.99 mmol) of vinylmagnesium bromide (1M in tetrahydrofuran) were added dropwise at 0° C. and the reaction mixture was stirred for 17 h at room temperature. Another 3 mL (3.00 mmol) of vinylmagnesium bromide (1M in tetrahydrofuran) were added and the mixture stirred for 20 h at room temperature. The reaction mixture was cooled to 0° C. and 15 mL of saturated aqueous sodium sulphate solution were added. The suspension was filtered over celite, the organic layer was dried over magnesium sulphate, filtered, and concentrated in vacuo. The crude product was purified by flash chromatography (SiO$_2$, 0%→100% ethyl acetate in heptane) to yield 1.09 g of (106). $R_t$=0.96 min (Method 18). Detected mass: 396.4 (M+H$^+$).

2-Methyl-propane-2-sulfinic acid {1-[8-(4-fluoro-phenyl)-1,4-dioxa-spiro[4.5]dec-8-yl]-3-methoxy-propyl}-amide (107)

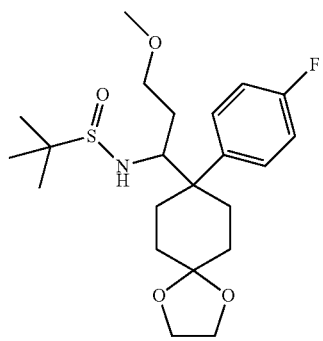 [SMILES: COCCC(NS(=O)C(C)(C)C)C1(c2ccc(F)cc2)CCC2(CC1)OCCO2]

16.5 mL (8.23 mmol) of a 0.5M solution of 9-BBN in tetrahydrofuran were added to a solution of 1.09 g (2.74 mmol) of 2-methyl-propane-2-sulfinic acid {1-[8-(4-fluoro-phenyl)-1,4-dioxa-spiro[4.5]dec-8-yl]allyl}-amide (106) in 5 mL THF at 0° C. The reaction mixture was allowed to warm to room temperature over night, before being cooled to 0° C. Then, 20 mL of 3M aqueous sodium hydroxide and 7.5 mL of 30% aqueous hydrogen peroxide were added slowly, and the mixture was stirred for 16 h at room temperature. The mixture was extracted twice with 50 mL of ethyl acetate, washed with water and saturated sodium chloride solution, dried over magnesium sulfate and concentrated in vacuo. The crude alcohol was dissolved in 5 mL of tetrahydrofuran and added slowly to a suspension of 131 mg (4.46 mmol) of sodium hydride (60%) in 5 mL tetrahydrofuran at 0° C. 515 µL (8.20 mmol) of iodomethane were added, and after stirring for 16 h at room temperature another 50 mg of sodium hydride (60%) were added. The reaction mixture was stirred for 1 h at room temperature, then 30 mL of methanol and 15 mL of aqueous ammonium hydroxide solution (33%) were added. The reaction mixture was evaporated to dryness and lyophilized from water to give 1.17 g of the title compound (107) in a purity sufficient for further conversion. $R_t$=0.93 min (Method 18). Detected mass: 428.2 (M+H$^+$).

cis-4-(1-Amino-3-methoxy-propyl)-4-(4-fluoro-phenyl)-cyclohexanol (108)

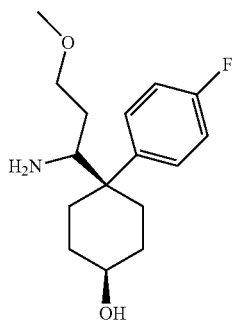

A solution of 1.16 g (2.71 mmol) of 2-methyl-propane-2-sulfinic acid {1-[8-(4-fluoro-phenyl)-1,4-dioxa-spiro[4.5]dec-8-yl]-3-methoxy-propyl}-amide (107) in a mixture of 5 mL of acetic acid and 1.25 mL of water was heated in the microwave oven at 100° C. for 5 min. The mixture was cooled to room temperature and slowly poured onto 100 mL of cold saturated aqueous sodium bicarbonate solution. The mixture was extracted three times with a 3:1 mixture of dichloromethane and ethanol (50 mL each). The organic phase was concentrated in vacuo to remove the dichloromethane and 203 mg (5.37 mmol) of sodium borohydride were added. The reaction mixture was stirred at room temperature overnight, when another 203 mg (5.37 mmol) of sodium borohydride were added. After 18 h at room temperature, the reaction mixture was quenched with water, concentrated in vacuo and lyophilized twice from water to give the title compound (108), which was used crude in the next step. $R_t$=1.95 min (Method 2). Detected mass: 282.2 (M+H$^+$).

Example 115 cis-6-[4-(1-Amino-3-methoxy-propyl)-4-(4-fluoro-phenyl)-cyclohexyloxy]-7-chloro-2H-isoquinolin-1-one

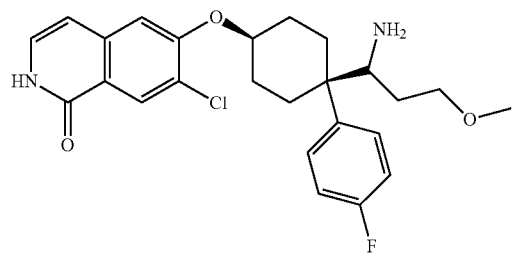 [SMILES: COCCC(N)[C@]1(c2ccc(F)cc2)CC[C@H](Oc2cc3cc[nH]c(=O)c3cc2Cl)CC1]

Example 115 was synthesized using the reaction sequence as described for the synthesis of Example 1. 414 mg of cis-4-(1-amino-3-methoxy-propyl)-4-(4-fluoro-phenyl)-cyclohexanol (108) and 283 mg of 7-chloro-6-fluoro-1-methoxy-isoquinoline (10) were used to give 66.6 mg of Example 115 as its hydrochloride. $R_t$=1.88 min (Method 12). Detected mass: 459.3 (M+H$^+$)

1-(1,4-Dioxa-spiro[4.5]dec-8-yl)-1-phenyl-ethylamine (26)

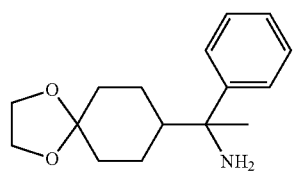 [SMILES: CC(N)(c1ccccc1)C1CCC2(CC1)OCCO2]

Under argon, phenylmagnesium bromide (3M) in diethyl ether (6.7 mL, 20 mmol) was added to a solution of 1,4-dioxa-spiro[4.5]decane-8-carbonitrile (3.34 g, 20 mmol) in diethyl ether (60 mL). The mixture was stirred for 30 minutes. Titanium (IV) isopropoxide (5.7 g, 20 mmol) was then added. After stirring for 5 min, methyl lithium (1.6 M in diethyl ether, 31.2 mL, 50 mmol) was added and the reaction was heated under reflux for 10 hours. After cooling in ice/water the brown mixture was treated cautiously with 2M NaOH solution (30 mL) dropwise (exothermic). The mixture was extracted with t-butyl methyl ether and dried over sodium sulphate. After filtration the organic phase was evaporated to give 5 g of a pale yellow oil, which was used in the next step without further purification. $R_t$=2.10 min (Method 2). Detected mass: 261.2 (M+H$^+$).

4-(1-Amino-1-phenyl-ethyl)-cyclohexanone (27)

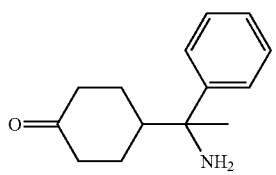

Crude 1-(1,4-dioxa-spiro[4.5]dec-8-yl)-1-phenyl-ethylamine (26, 2.5 g) was dissolved in acetone (40 mL) and treated with 6M aqueous hydrochloric acid (21.1 mL). After 5 hours stirring the mixture was evaporated at less than 20° C. to give a residue which was treated with dichloromethane, washed with saturated sodium bicarbonate solution, dried and filtered to give a solution of crude product which was used immediately. $R_t$=0.7 min (Method 5). Detected mass: 218.3 (M+H$^+$).

[1-(4-Oxo-cyclohexyl)-1-phenyl-ethyl]carbamic acid tert-butyl ester (28)

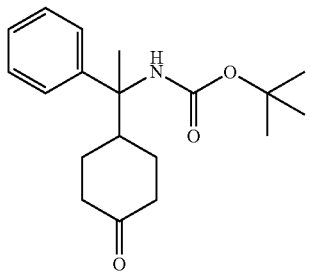 [SMILES: CC(C)(C)OC(=O)NC(C)(c1ccccc1)C1CCC(=O)CC1]

With cooling di-tert.-butyl dicarbonate (3.46 g, 10.6 mmol) and triethylamine (1.47 mL, 10.6 mmol) was added to the crude solution of 4-(1-amino-1-phenyl-ethyl)-cyclohexanone (27) from the previous stage. After stirring overnight, the reaction was worked up by extraction with dichloromethane, washing with 1M NaOH solution and then with 0.05M aqueous hydrochloric acid (three times until pH of washings were pH4). After washing the organic phase with brine, it was dried over sodium sulphate, filtered and evaporated to give crude product (28) as a colourless oil which was used without further purification. $R_t$=0.14 min (Method 5). Detected mass: 318.4 (M+H$^+$)

[1-(4-Hydroxy-cyclohexyl)-1-phenyl-ethyl]carbamic acid tert-butyl ester (29)

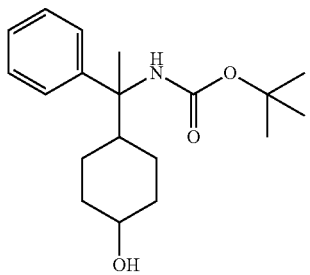 [SMILES: CC(C)(C)OC(=O)NC(C)(c1ccccc1)C1CCC(O)CC1]

[1-(4-Oxo-cyclohexyl)-1-phenyl-ethyl]-carbamic acid tert-butyl ester (28) from the previous stage (2.7 g) was dissolved in THF (60 mL) and cooled to −70° C. Sodium borohydride was added (356 mg) and the reaction mixture stirred overnight with gradual warming to room temperature. Water was added and the solution extracted with t-butylmethyl ether. The organic phase was washed with brine and dried over sodium sulphate. Evaporation gave 1.24 g of a white foam as crude product. $R_t$=1.41 min (Method 5). Detected mass: 246.3 (M—C$_4$H$_8$—H$_2$O+H$^+$).

4-(1-Amino-1-phenyl-ethyl)-cyclohexanol (30)

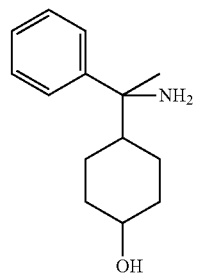 [SMILES: CC(N)(c1ccccc1)C1CCC(O)CC1]

Trifluoroacetic acid (8 mL) was added to a solution of [1-(4-hydroxy-cyclohexyl)-1-phenyl-ethyl]-carbamic acid tert-butyl ester (29) in dichloromethane (75 mL) from the previous stage. After stirring for 4 hours the reaction mixture was worked up by adding 2M aqueous hydrochloric acid (39 mL), followed by evaporation. Freeze drying overnight gave a pale brown semi-solid residue. This was treated with a mixture of water and acetonitrile. After freeze drying again 1.24 g of crude product as the hydrochloride was obtained which was used in the next stage without further purification. $R_t$=0.58 min (Method 5). Detected mass: 185.15 (M—NH$_3$—H$_2$O+H$^+$).

1-[4-(1-Benzyloxy-7-chloro-isoquinolin-6-yloxy)-cyclohexyl]-1-phenyl-ethylamine (31)

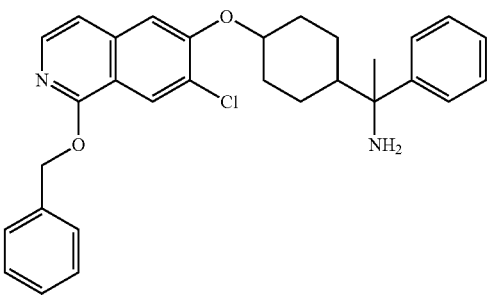 [SMILES: CC(N)(c1ccccc1)C1CCC(Oc2cc3ccnc(OCc4ccccc4)c3cc2Cl)CC1]

4-(1-Amino-1-phenyl-ethyl)-cyclohexanol (30, 404 mg, 1.6 mmol) was evaporated twice to dryness from toluene. The residue was dissolved in dimethylacetamide (3 mL) and the solution added dropwise to a suspension of sodium hydride (114 mg, 4.1 mmol, 60% in mineral oil) in dimethyl acetamide (8 mL) under argon. After stirring for 1 hour, a solution of 1-benzyloxy-7-chloro-6-fluoroquinoline (38, 0.31 g, 1.09 mmol) in dimethylacetamide (6 mL) was added dropwise and the mixture stirred overnight. Then mixture was then heated and stirred at 60° C. for 1 hour before cooling and addition of water (30 mL) to quench the reaction. The product was isolated by extraction with dichloromethane/isopropanol (3:1) and evaporation of the organic phase under reduced pressure. Purification by column chromatography (silica gel, 2% methanol in dichloromethane) gave the desired product (67 mg) as a colourless solid. $R_t$=4.3 min (Method 3). Detected mass: 487.3 (M+H$^+$).

Example 34

6-[4-(1-Amino-1-phenyl-ethyl)-cyclohexyloxy]-7-chloro-2H-isoquinolin-1-one

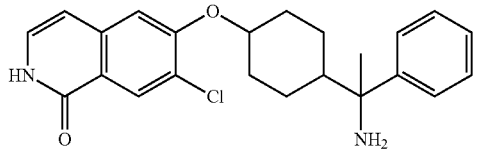

Hydrochloric acid (6.6 mL of a 2M aqueous solution) was added to a solution of 1-[4-(1-benzyloxy-7-chloro-isoquinolin-6-yloxy)-cyclohexyl]-1-phenyl-ethylamine (31, 67 mg, 0.14 mmol) in isopropanol (7 mL). The reaction mixture was stirred overnight. Isopropanol was removed under reduced pressure and the remaining aqueous solution freeze dried to give crude product as an amorphous powder.

This was treated twice with acetonitrile/water and freeze dried to give 57 mg of the desired product as a colourless hydrochloride salt. $R_t$=2.83 min (Method 3). Detected mass: 380.3 (M—NH$_3$+H$^+$).

Example 116

6-{4-[1-Amino-1-(4-fluoro-phenyl)-ethyl]-cyclohexyloxy}-7-chloro-2H-isoquinolin-1-one (Isomer 1)

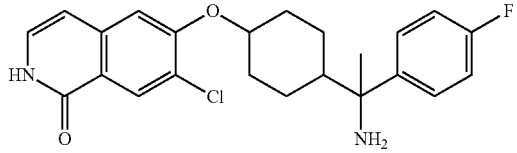

6-{-4-[1-Amino-1-(4-fluoro-phenyl)-ethyl]-cyclohexyloxy}-7-chloro-2H-isoquinolin-1-one (Example 116) was obtained by the same procedure described for the synthesis of Example 34 using 1-benzyloxy-7-chloro-6-fluoroquinoline (38) and 4-[amino-4-fluoro-phenyl-methyl]-cyclohexanol (prepared from 1,4-dioxa-spiro[4.5]decane-8-carbonitrile, 4-fluorophenyl-magnesium bromide and methyl lithium analogously to 30). $R_t$=1.74 min (Method 20). Detected mass: 398.2 (M—NH$_3$+H$^+$).

Example 117

6-{-4-[1-Amino-1-(4-methoxy-phenyl)-ethyl]-cyclohexyloxy}-7-chloro-2H-isoquinolin-1-one a) 1-[4-(7-chloro-1-methoxyisoquinolin-6-yloxy)-cyclohexyl]-1-(4-methoxyphenyl)-ethylamine (109)

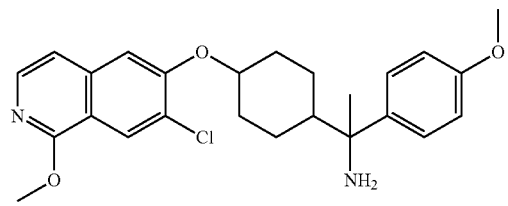 [SMILES: COc1ccc(C(C)(N)C2CCC(Oc3cc4ccnc(OC)c4cc3Cl)CC2)cc1]

4-[1-Amino-1-(4-methoxyphenyl)-ethyl]-cyclohexanol (prepared as described for the synthesis of 30, 400 mg, 1.4 mmol) was evaporated twice to dryness from toluene. The residue was dissolved in dimethylacetamide (3 mL) and the solution added dropwise to a suspension of sodium hydride (147 mg, 3.7 mmol, 60% in mineral oil) in dimethyl acetamide (6 mL) under argon. After stirring for 1 hour, a solution of 7-chloro-6-fluoro-1-methoxyisoquinoline (0.3 g, 1.4 mmol) in dimethylacetamide (6 mL) was then added dropwise and the mixture stirred overnight. The mixture was then heated and stirred at 60° C. for 1 hour before cooling and addition of water (30 mL) to quench the reaction.

Product was isolated by extraction with dichloromethane/isopropanol (3:1) and evaporation of the organic phase under reduced pressure. Purification by column chromatography (silica gel, dichloromethane to dichloromethane:methanol=98:2 to MeOH) gave desired product (30 mg) as a colourless solid. $R_t$=3.84 min (Method 3). Detected mass: 441.4 (M+H$^+$).

b) 6-{4-[1-Amino-1-(4-methoxy-phenyl)-ethyl]-cyclohexyloxy}-7-chloro-2H-isoquinolin-1-one (Example 117)

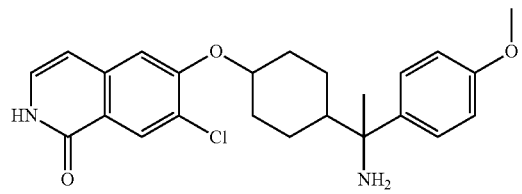

Hydrochloric acid (0.4 mL of a 1M aqueous solution) was added to a solution of 1-[4-(7-chloro-1-methoxyisoquinolin-6-yloxy)-cyclohexyl]-1-(4-methoxyphenyl)-ethylamine (109, 30 mg, 0.07 mmol) in isopropanol (0.4 mL). The reaction mixture was heated in a microwave oven at 100° C. for 30 minutes. Isopropanol was removed under reduced pressure and the remaining aqueous solution freeze dried to give crude product as an amorphous powder. This was treated twice with acetonitrile/water and freeze dried to give 29 mg of the desired product Example 117 as a colourless hydrochloride salt. $R_t$=2.60 min (Method 2). Detected mass: 410.1 (M—NH$_3$+H$^+$).

The following racemic products were obtained by the same procedure described for the synthesis of Example 117 using 7-chloro-6-fluoro-1-methoxyisoquinoline (10) and the corresponding aminoalcohols (prepared from the respective carbonitriles, grignard reagents and methyl or ethyl lithium reagents analogously to 30). One stereoisomer could be isolated (named isomer 1); the relative stereochemistry was not assigned.

A solution of sodium trimethylsilanoate (149.2 mL, 1M in THF) was added to a solution of 7-chloro-6-fluoro-1-methoxyisoquinoline (10, 10 g, 47.2 mmol) in DMA (200 mL) under argon. After stirring at 60° C. for 24 hours, the solution was evaporated under reduced pressure and then freeze dried to give crude product (20.4 g). This was dissolved in water and the pH adjusted to pH=6.5. A light brown precipitate was collected by filtration and purified by reverse phase chromatography (0 to 4 minutes, 15% acetonitrile/water, 4 to 24 minutes 15 to 90% acetonitrile/water and then 100% aceto-

| Example | Product | Chemical Name | [M + H$^+$] | $R_t$/ [min] | Method |
|---|---|---|---|---|---|
| 118 | | 6-{4-[1-Amino-1-cyclopentyl-ethyl]-cyclo-hexyl-oxy}-7-chloro-2H-iso-quinolin-1-one | 389.5 | 3.10 | 3 |
| 119 | | 6-{4-[1-Amino-1-ethyl-propyl]-cyclohexyloxy}-7-chloro-2H-isoquinolin-1-one | 363.2 | 1.71 | 12 |
| 120 | | 6-{4-[1-Amino-1-cyclopropyl-ethyl]-cyclo-hexyloxy}-7-chloro-2H-iso-quinolin-1-one | 361.2 | 1.98 | 13 |
| 121 | | 6-{4-[1-Amino-1-n-propyl-ethyl]-cyclo hexyloxy}-7-chloro-2H-isoquinolin-1-one | 363.2 | 1.77 | 12 |

Example 122

6-{-4-[1-Amino-1-ethyl-propyl]-cyclohexyloxy}-7-chloro-2H-isoquinolin-1-one (Isomer 2)

a) 7-chloro-6-hydroxy-1-methoxyisoquinoline (110)

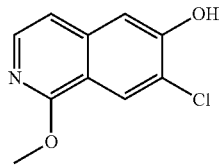

nitrile) to give 7 g of the desired product. $R_t$=2.60 min (Method 2). Detected mass: 210.0 (M+H$^+$).

b) 1-(4-[7-Chloro-1-methoxyisoquinolin-6-yloxy-cyclohexyl)-1-ethyl-propyl]-carbamic acid tert-butyl ester (111)

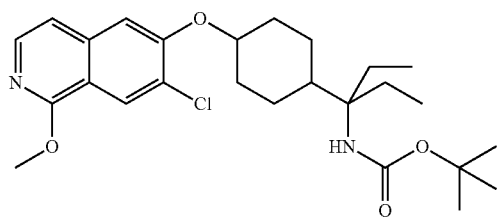 [SMILES: CCC(CC)(NC(=O)OC(C)(C)C)C1CCC(Oc2cc3ccnc(OC)c3cc2Cl)CC1]

[1-(4-Hydroxycyclohexyl)-1-ethyl-propyl]-carbamic acid tert-butyl ester (from the preparation of 119) was dried by evaporating twice from toluene. The dried material was dissolved in dry THF (2.5 mL) and triphenylphosphine (0.63 g, 2.42 mmol), and 7-chloro-6-hydroxy-1-methoxyisoquinoline (110, 0.39 g, 1.86 mmol) added. Then Hunig's base (0.24 g, 0.32 mL, 1.86 mmol) was added. The reaction mixture was cooled to 0° C. and DEAD (0.49 g, 434 µl, 2.79 mmol) added dropwise over 1 hour. The reaction mixture was warmed to 25° C. and stirred overnight.

using 7-chloro-6-hydroxy-1-methoxyisoquinoline (110) and the corresponding 1-(4-hydroxycyclohexyl)-1-ethyl]-carbamic acid tert-butyl ester (prepared analogously to 30). The isolated products are different stereoisomers as compared to Example 34 and Example 121, therefore named "isomer 2", their relative stereochemistry, however, was not assigned.

| Example | Product | Chemical Name | [M + H⁺] | $R_t$/ [min] | Method |
|---|---|---|---|---|---|
| 123 | | 6-{4-[1-Amino-1-phenyl-ethyl]-cyclohexyloxy}-7-chloro-2H-isoquinolin-1-one | 397.12 | 1.74 | 12 |
| | Isomer 2 | | | | |
| 124 | | 6-{4-[1-Amino-1-methyl-n-butyl]-cyclo hexyloxy}-7-chloro-2H-isoquinolin-1-one | 363.2 | 1.76 | 21 |
| | Isomer 2 | | | | |

The reaction mixture was taken up in dichloromethane, washed twice with aqueous 2M NaOH solution and once with brine. Drying over sodium sulphate followed by filtration and evaporation gave 1.7 g of crude product which was purified by stirring three times with 5% ethyl acetate/95% heptane. Combined organic extracts were evaporated to give a brown residue which was purified by chromatography on silica gel. Elution with heptane/ethyl acetate (95:5) gave 113 mg of desired compound. $R_t$=1.54 min (Method 11). Detected mass: 476.2 (M+H⁺).

c) 6-{-4-[1-Amino-1-ethyl-propyl]-cyclohexyloxy}-7-chloro-2H-isoquinolin-1-one, isomer 2 (Example 122)

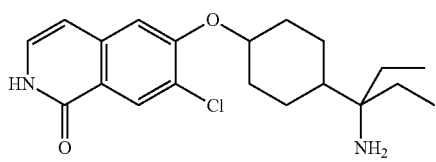 [SMILES: CCC(N)(CC)C1CCC(Oc2cc3cc[nH]c(=O)c3cc2Cl)CC1]

1-(4-[7-Chloro-1-methoxyisoquinolin-6-yloxy-cyclohexyl)-1-ethyl-propyl]-carbamic acid tert-butyl ester (111, 113 mg, 0.24 mmol) was dissolved in isopropanol (1.5 mL) and treated with hydrochloric acid (1M, 1.5 mL). The reaction mixture was heated in a microwave oven at 100° C. for 30 minutes. Evaporation gave crude product, which was treated twice with acetonitrile/water and freeze dried to give 63 mg of the desired product as a colourless hydrochloride salt. $R_t$=2.45 min (Method 2). Detected mass: 363.3 (M+H⁺).

The following two racemic products were obtained by the same procedure described for the synthesis of Example 122

Example 125 and 126

6-[3-(1-Amino-propyl)-3-(4-fluoro-phenyl)-cyclobutyloxy]-7-chloro-2H-isoquinolin-1-one a) 3-Cyano-3-(4-fluorophenyl)cyclobutan-1-ol (112)

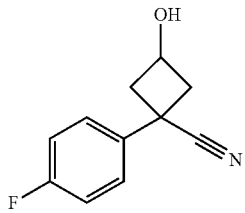 [SMILES: N#CC1(c2ccc(F)cc2)CC(O)C1]

Methyl lithium-lithium bromide complex (123 mL, 185 mmol) was added dropwise to a solution of 4-fluoroacetonitrile (22 mL, 25 g, 185 mmol) in THF (550 mL) at −70° C. After stirring for 1 hour at −70° C., a solution of epibromhydrin (15.8 mL, 25.3 g, 185 mmol) in THF (125 mL) was added dropwise. The reaction mixture was stirred for a further hour. Then, at −70° C., methyl magnesium iodide in ether (3M, 61.7 mL, 185 mmol) was added dropwise and the reaction mixture allowed to warm up gently to room temperature with stirring overnight. The reaction mixture was then cooled in an ice bath and dropwise water (30 mL) and then hydrochloric acid (5M) were added. The acidic solution was saturated with sodium chloride and extracted with methyl t-butyl ether. The organic phase was then washed with sodium thiosulphate solution and brine. After drying over sodium sulphate, followed by filtration, the solvent was removed under reduced pressure to give crude product (33.5 g) as an orange oil. The compound was purified by chromatography on silica gel, elution with heptane/ethyl acetate gave 19.8 g of the desired compound. $R_t$=3.33 min (Method 3). Detected mass: 192.1 (M+H$^+$).

b) 3-Cyano-3-(4-fluorophenyl)cyclobutan-1-yl t-butyldimethylsilyl ether (113)

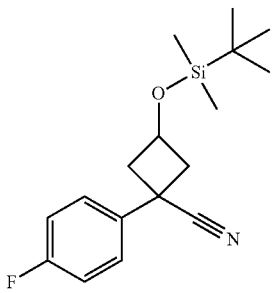 [SMILES: CC(C)(C)[Si](C)(C)OC1CC(C#N)(c2ccc(F)cc2)C1]

3-cyano-3-(4-fluorophenyl)cyclobutan-1-ol (112, 19.8 g, 103.6 mmol) was dissolved in dichloromethane (200 mL) under argon, then 2,6-lutidine (27.78 g, 30.1 mL, 259 mmol) was added and the solution cooled to 0° C. tert-Butyldimethylsilyl trifluoromethanesulphonate (32.9 g, 28.6 mL, 124.3 mmol) was added dropwise and the stirred reaction mixture was then allowed to warm up to room temperature overnight. The reaction mixture was washed successively with water, hydrochloric acid (0.1M), saturated sodium bicarbonate solution and brine before being dried over sodium sulphate. Filtration and evaporation gave 32.9 g of a yellow oil which was used in the next step without further purification. $R_t$=1.30 min (Method 18). Detected mass: 306.3 (M+H$^+$).

c) 1-(1-Aminopropyl)-1-(4-fluorophenyl)cyclobutan-3-ol (114)

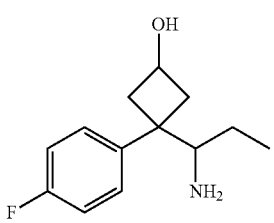 [SMILES: CCC(N)C1(c2ccc(F)cc2)CC(O)C1]

3-cyano-3-(4-fluorophenyl)cyclobutan-1-yl-t-butyldimethylsilyl ether (113, 1.55 g, 5.1 mmol) was dissolved in toluene (4 mL) and ethyl magnesium bromide (3.4 mL, 10.2 mmol, 3M in ether) added dropwise. The reaction mixture was then stirred for 30 minutes at 90° C. After cooling to 0° C., the reaction was quenched by addition of methanol (20 mL) followed by addition of sodium borohydride (384 mg, 10.2 mmol). After stirring overnight dilute sodium hydroxide was added (50 mL, 1M aqueous solution) and the mixture extracted with methyl-tert-butyl ether. The organic phase was stirred with hydrochloric acid (2N, 100 mL) for 4 hours. The aqueous layer was then washed with methyl-tert butyl ether before being made basic with sodium hydroxide solution (5M) and extracted with dichloromethane/isopropanol (3/1). Evaporation of the organic layer gave 900 mg of (114) as a yellow oil. $R_t$=1.04 min (Method 10). Detected mass: 224.2 (M+H$^+$).

d) 1-[3-(7-Chloro-1-methoxyisoquinolin-6-yloxy)-cyclobutyl]-1-(4-fluorophenyl)-propylamine (115 and 116)

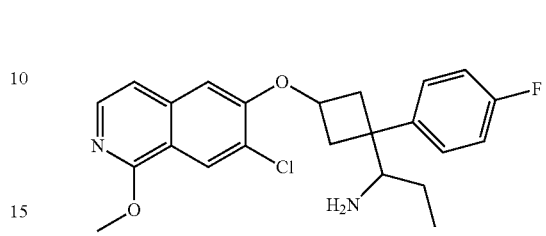

1-[3-(7-chloro-1-methoxyisoquinolin-6-yloxy)-cyclobutyl]-1-(4-fluorophenyl)-propylamine (2 isomeric mixtures) were prepared from 1-(1-aminopropyl)-1-(4-fluorophenyl) cyclobutan-3-ol (114) and 7-chloro-6-fluoro-1-methoxyisoquinoline (10) as described for (109). The two stereoisomers could be separated by silica gel chromatography, relative stereochemistry was not assigned.

115: $R_t$=1.50 min (Method 10). Detected mass: 415.2 (M+H$^+$)

116: $R_t$=1.55 min (Method 10). Detected mass: 415.2 (M+H$^+$)

e) 6-[3-(1-Amino-propyl)-3-(4-fluoro-phenyl)-cyclobutyloxy]-7-chloro-2H-isoquinolin-1-one (Example 125 and 126)

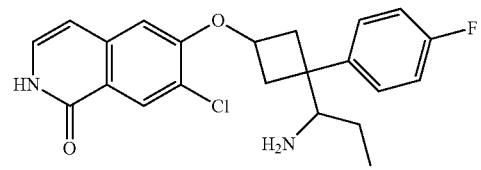 [SMILES: CCC(N)C1(c2ccc(F)cc2)CC(Oc2cc3cc[nH]c(=O)c3cc2Cl)C1]

6-[3-(1-Amino-propyl)-3-(4-fluorophenyl)-cyclobutyloxy]-7-chloro-2H-isoquinolin-1-one (Example 125 and 126) were prepared from 1-[3-(7-chloro-1-methoxyisoquinolin-6-yloxy)-cyclobutyl]-1-(4-fluorophenyl)-propylamines 115 and 116 as described for Example 117.

Example 125: $R_t$=0.94 min (Method 11). Detected mass: 401.1 (M+H$^+$).

Example 126: $R_t$=1.34 min (Method 10). Detected mass: 401.1 (M+H$^+$).

Example 127

6-[3-(1-Amino-propyl)-3-(4-fluoro-phenyl)-cyclopentyloxy]-7-chloro-2H-isoquinolin-1-one a) 1-cyano-1-(4-fluorophenyl)cyclopent-3-ene (117)

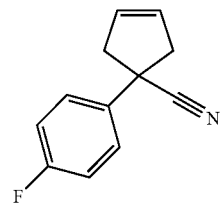 [SMILES: N#CC1(c2ccc(F)cc2)CC=CC1]

Sodium hydride (14.4 g, 0.36 mol, 60% in oil) was added to ice cooled DMSO (500 mL) under argon and stirred for 10 minutes. 4-Fluoroacetonitrile (22.4 g, 0.16 mol) was dissolved in DMSO (200 mL) and then added over 15 minutes to the stirred, cooled sodium hydride mixture. After dropwise addition of cis-1,4-dichlorobutene (17.7 g, 14.9 mL) the mixture was allowed to warm to room temperature and was then stirred overnight. The reaction was quenched by gentle addition to 1000 mL ice cold water and followed by extraction with dichloromethane. Evaporation gave crude product which was taken up in heptane/ethyl acetate (1/1) and washed with water three times. The organic phase was dried over sodium sulphate, filtered and evaporated to give 33.7 g red oil. This was purified by chromatography on silica gel, elution with heptane/ethyl acetate (1/2) gave 10.1 g of desired compound 117.

b) 1-(1-aminopropyl)-1-(4-fluorophenyl)cyclopent-3-ene (118)

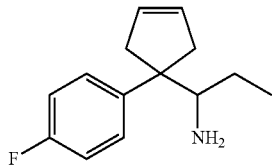 [SMILES: CCC(N)C1(c2ccc(F)cc2)CC=CC1]

1-cyano-1-(4-fluorophenyl)cyclopent-3-ene (117, 1.4 g, 7.48 mmol) was dissolved in toluene (3.5 mL) and ethyl magnesium bromide (5 mL, 15 mmol, 3M in ether) added. After stirring for 2.5 hours, the reaction mixture was added dropwise to ice cold methanol (50 mL), followed by sodium borohydride (560 mg, 15 mmol). The mixture was warmed to room temperature and stirred overnight. The white suspension was treated with sodium hydroxide solution (aq, 1M, 125 mL) and then extracted with dichloromethane/isopropanol (3/1). The organic phase was washed with brine, dried over sodium sulphate and evaporated to give 1.2 g of a yellow oil. This was taken up in dichloromethane and extracted twice with dilute hydrochloric acid (2M). The combined aqueous layers were made basic with aqueous sodium hydroxide solution (5M) and re-extracted with dichloromethane/isopropanol (3/1). Drying over sodium sulphate and evaporation gave 348 mg of the desired product $R_t$=2.37 min (Method 2). Detected mass: 220.1 (M+H$^+$).

c) 1-(1-aminopropyl)-1-(4-fluorophenyl)cyclopentan-3-ol (119)

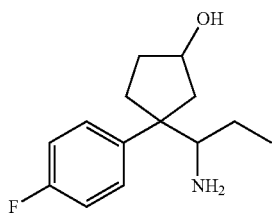 [SMILES: CCC(N)C1(c2ccc(F)cc2)CCC(O)C1]

1-(1-aminopropyl)-1-(4-fluorophenyl)cyclopent-3-ene (118, 348 mg, 1.6 mmol) was dissolved in THF at 0° C. under argon. Borane (1.75 mL, 1.75 mmol, 1M in THF) was added dropwise over 10 minutes. The reaction mixture was allowed to warm to room temperature before stirring overnight. After cooling to 0° C., water was added (4 mL), followed by hydrogen peroxide (0.61 mL, 30% solution in water) and sodium hydroxide solution (1.75 mL, 1M aqueous solution). After stirring for 5 minutes the mixture was extracted with ethyl acetate, dried over sodium sulphate and evaporated to give 458 mg of desired product, which was stirred for 15 minutes with dilute hydrochloric acid (10 mL, 2M aqueous solution). Evaporation, followed by freeze drying gave 514 mg of the desired product as mixture of four stereoisomers as a colourless hydrochloride salt. $R_t$=1.83, 1.99, 2.36, 2.86 min (Method 2). Detected mass: 203.1 (M—NH$_3$—H$_2$O+H$^+$).

d) 1-[3-(7-chloro-1-methoxyisoquinolin-6-yloxy)-cyclopentyl]-1-(4-fluorophenyl)-propylamine (120)

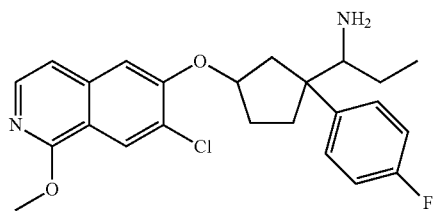 [SMILES: CCC(N)C1(c2ccc(F)cc2)CCC(Oc2cc3ccnc(OC)c3cc2Cl)C1]

1-[3-(7-chloro-1-methoxyisoquinolin-6-yloxy)-cyclopentyl]-1-(4-fluorophenyl)-propylamine (120) was prepared from 1-(1-aminopropyl)-1-(4-fluorophenyl)cyclopentan-3-ol (119) and 7-chloro-6-fluoro-1-methoxyisoquinoline (10) as described for 109. $R_t$=1.11 min (Method 11). Detected mass: 429.3 (M+H$^+$). The product was obtained as a mixture of isomers, their relative stereochemistry was not assigned.

e) 6-[3-(1-Amino-propyl)-3-(4-fluorophenyl)-cyclopentyloxy]-7-chloro-2H-isoquinolin-1-one (Example 127)

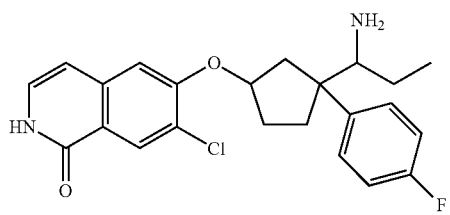 [SMILES: CCC(N)C1(c2ccc(F)cc2)CCC(Oc2cc3cc[nH]c(=O)c3cc2Cl)C1]

6-[3-(1-Amino-propyl)-3-(4-fluorophenyl)-cyclopentyloxy]-7-chloro-2H-isoquinolin-1-one (Example 127) was prepared from 1-[3-(7-chloro-1-methoxyisoquinolin-6-yloxy)-cyclopentyl]-1-(4-fluorophenyl)-propylamine (120) as described for Example 117. The material was obtained as a mixture of stereoisomers, their relative stereochemistry was not assigned. $R_t$=1.34, 1.37 min (Method 10). Detected mass: 415.1 (M+H$^+$).

C-(1,4-Dioxa-spiro[4.5]dec-8-yl)-C-(4-methoxyphenyl)-methylamine (32)

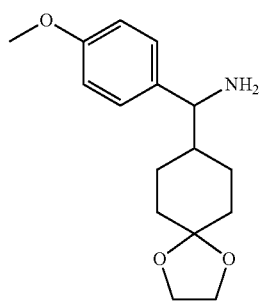 [SMILES: COc1ccc(C(N)C2CCC3(CC2)OCCO3)cc1]

Under argon, 4-methoxy-phenylmagnesium bromide (0.5M in THF, 24 mL, 12 mmol) was added to a solution of 1,4-dioxa-spiro[4.5]decane-8-carbonitrile (1.0 g, 6 mmol) in THF (100 mL). The mixture was stirred under reflux for 16 hours. The reaction mixture was then cooled to 0° C. Saturated sodium sulphate solution was added dropwise until no more precipitate formed. The precipitate was removed by filtration and washed with THF. The combined organic phases were stirred with sodium borohydride (452 mg, 12 mmol) overnight at 25° C. The reaction mixture was then diluted with t-butyl methyl ether (100 mL) and treated with 0.05M aqueous hydrochloric acid (three times with 100 mL). The combined aqueous phases were adjusted to alkaline pH with a 6M aqueous sodium hydroxide solution with cooling, before extraction with dichloromethane gave a solution of the desired product which was used directly in the next stage. $R_t$=0.74 min (Method 5). Detected mass: 278.2 (M+H$^+$).

[(4-Methoxy-phenyl)-(4-oxo-cyclohexyl)-methyl]-carbamic acid tert-butyl ester (33)

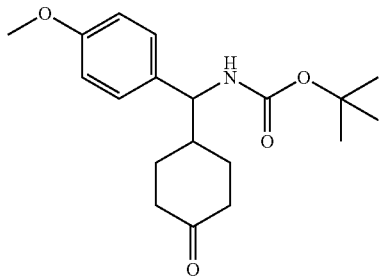 [SMILES: COc1ccc(C(NC(=O)OC(C)(C)C)C2CCC(=O)CC2)cc1]

With cooling di-tert.-butyl dicarbonate (1.31 g, 6 mmol) and triethylamine (0.83 mL, 6 mmol) were added to the crude solution of C-(1,4-dioxa-spiro[4.5]dec-8-yl)-C-(4-methoxy-phenyl)-methylamine (32) from the previous stage. After stirring overnight, the reaction was worked up by extraction with dichloromethane and washing with 1M HCl. The aqueous layer was treated with 1M NaOH solution to basic pH and then extracted with dichloromethane. After washing the combined organic phase with brine, and drying over sodium sulphate, the organic phase was evaporated to give crude product which was chromatographed on silica gel. Elution with ethyl acetate/hexane (30/70) gave 110 mg of the desired product. $R_t$=4.42 min (Method 6). Detected mass: 278.1 (M-isobutene+H$^+$).

[(4-Hydroxy-cyclohexyl)-(4-methoxy-phenyl)-methyl]-carbamic acid tert-butyl ester (34)

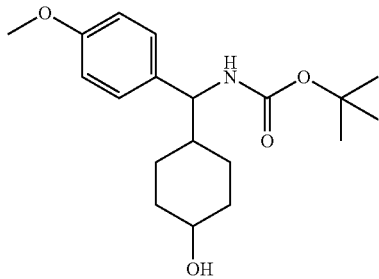 [SMILES: COc1ccc(C(NC(=O)OC(C)(C)C)C2CCC(O)CC2)cc1]

Sodium borohydride (12 mg, 0.34 mmol) and 2 drops methanol were added to a solution of [(4-methoxy-phenyl)-(4-oxo-cyclohexyl)-methyl]-carbamic acid tert-butyl ester (33, 110 mg) in THF (5 mL). After stirring for 7 hours the reaction was worked up by washing the solution with saturated sodium bicarbonate solution and brine. After drying the organic phase over sodium sulphate, followed by filtration, evaporation gave 101 mg of the desired cis/trans isomer mixture (34) as a colourless solid, which was used directly in the next stage. $R_t$=1.36, 1.39 min (Method 5). Detected mass: 219.2 (M—C$_4$H$_8$—CO$_2$—H$_2$O$^+$).

4-[Amino-(4-methoxy-phenyl)-methyl]-cyclohexanol (35)

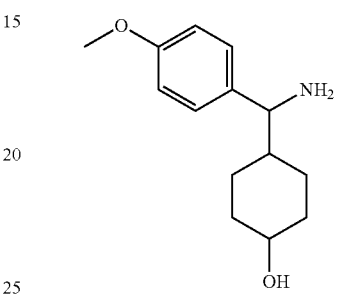

Trifluoroacetic acid (0.31 mL) was added to a solution of [(4-hydroxy-cyclohexyl)-(4-methoxy-phenyl)-methyl]-carbamic acid tert-butyl ester (34, 101 mg) in dichloromethane (6 mL). After stirring for 2 hours, 2M hydrochloric acid (3 mL) was added. Evaporation gave crude product as a colourless solid. Water and acetonitrile were added and the mixture was concentrated and then freeze dried to give 83 mg of 4-[amino-(4-methoxy-phenyl)-methyl]-cyclohexanol (35) as the hydrochloride salt. $R_t$=0.71 min (Method 5). Detected mass: 219.2 (M—NH$_2$$^+$).

C-[4-(1-Benzyloxy-7-chloro-isoquinolin-6-yloxy)-cyclohexyl]-C-(4-methoxy-phenyl)-methylamine (36 and 37)

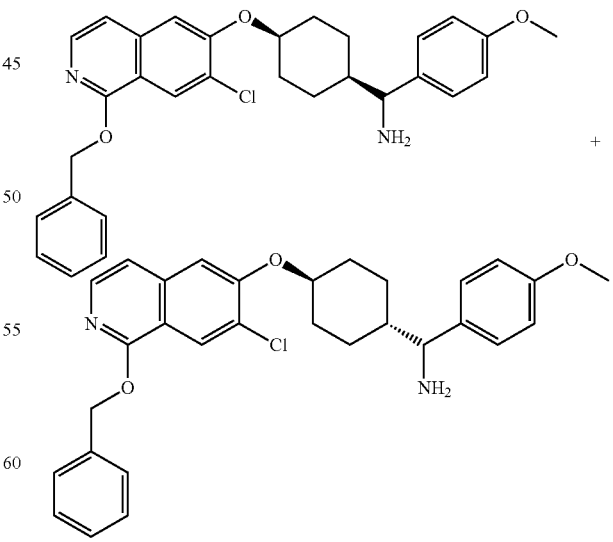

4-[Amino-(4-methoxy-phenyl)-methyl]-cyclohexanol (35, 83 mg, 0.3 mmol) was evaporated twice to dryness from toluene. The residue was dissolved in dimethylacetamide (1 mL) and the solution added dropwise to a suspension of sodium hydride, (37 mg, 0.92 mmol, 60% in mineral oil) in dimethyl acetamide (2 mL) under argon. After stirring for 1 hour a solution of 1-benzyloxy-7-chloro-6-fluoroquinoline (38, 62 mg, 0.21 mmol) in dimethylacetamide (2 mL) was then added dropwise and the mixture stirred overnight. Then mixture was then treated with water (6 mL) to quench the reaction. Product was isolated by extraction with dichloromethane/isopropanol (3:1) and the crude product was then obtained by evaporation of the organic phase under reduced pressure. Purification by column chromatography (silica gel, 5% methanol in dichloromethane) gave 40 mg of the earlier eluting isomer 1 (36) and 40 mg of the later eluting isomer 2 (37), both as colourless solids. The relative stereochemistry was not assigned.

36: $R_t$=1.46 min (Method 5). Detected mass: 503.2 (M+H$^+$).

37: $R_t$=1.51 min (Method 5). Detected mass: 503.2 (M+H$^+$).

Example 35 and Example 36

6-{4-[Amino-(4-methoxy-phenyl)-methyl]-cyclohexyloxy}-7-chloro-2H-isoquinolin-1-one

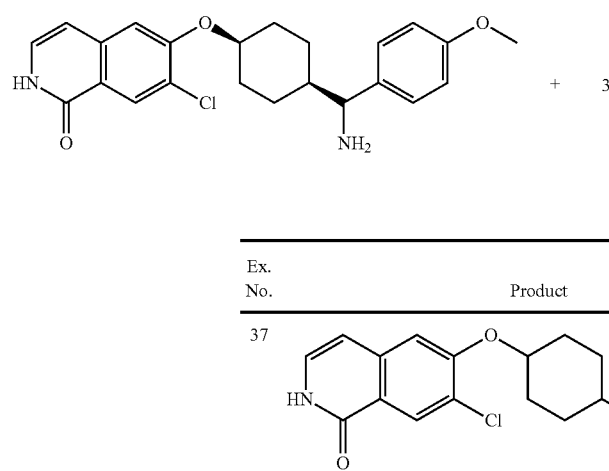

+

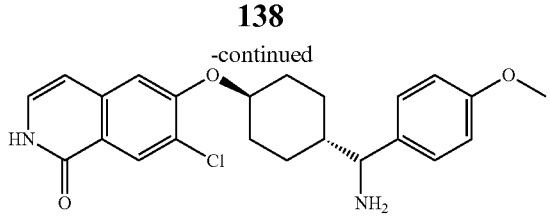

-continued

A 2M aqueous solution of hydrochloric acid (3.8 mL) was added to a solution of C-[4-(1-benzyloxy-7-chloro-isoquinolin-6-yloxy)-cyclohexyl]-C-(4-methoxy-phenyl)-methylamine (36, 40 mg, 0.08 mmol) in isopropanol (4 mL). The reaction mixture was stirred overnight. Isopropanol was removed under reduced pressure and the remaining aqueous solution freeze dried to give crude product as an amorphous powder. This was treated twice with acetonitrile/water and freeze dried to give the desired product as a colourless hydrochloride salt. The relative stereochemistry was not assigned.

Example 35: $R_t$=2.56 min (Method 1). Detected mass: 396.2 (M—NH$_2^+$)

Example 36 was synthesized analogously starting from 37: $R_t$=2.86 min (Method 1). Detected mass: 396.2 (M—NH$_3$+H$^+$)

The following four products were obtained by the same procedure described for the synthesis of example 35 and example 36 using 1-benzyloxy-7-chloro-6-fluoroisoquinoline and the corresponding 4-[amino-phenyl-methyl]-cyclohexanols, using the respective phenyl Grignard reagents and 1,4-dioxa-spiro[4.5]decane-8-carbonitriles.

| Ex. No. | Product | Chemical Name | [M + H$^+$] | Isomer | $R_t$/[min] | Method |
|---|---|---|---|---|---|---|
| 37 | | 6-{4-[Amino-(4-fluoro-phenyl)-methyl]-cyclohexyloxy}-7-chloro-2H-isoquinolin-1-one | 401.2 | 1 | 2.61 | 1 |
| 38 | | 6-[4-(Amino-p-tolyl-methyl)-cyclohexyloxy]-7-chloro-2H-isoquinolin-1-one | 397.2 | 1 | 2.69 | 1 |
| 39 | | 6-[4-(Amino-p-tolyl-methyl)-cyclohexyloxy]-7-chloro-2H-isoquinolin-1-one | 397.0 | 2 | 2.63 | 1 |
| 40 | | 6-[4-(Amino-phenyl-methyl)-cyclohexyloxy]-7-chloro-2H-isoquinolin-1-one | 383.2 | 1 | 2.51 | 1 |

Alternative Synthesis of Example 40

6-[4-(Amino-phenyl-methyl)-cyclohexyloxy]-7-chloro-2H-isoquinolin-1-one a) 4-Hydroxy-cyclohexanecarbonitrile (121)

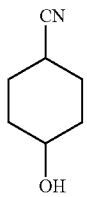

A solution of 10.0 g (59.8 mmol) of 4-cyanocyclohexanone cyclic ethylene acetal in a mixture of 80 mL of acetic acid and 20 mL of water was heated in the microwave oven at 130° C. for 20 min. The mixture was cooled to room temperature and slowly poured onto 2.2 L of cold saturated aqueous sodium bicarbonate solution. The mixture was extracted twice with dichloromethane, the organic phase was dried over magnesium sulphate, filtered, 100 mL of ethanol were added and the dichloromethane was removed in vacuo. To the solution were then added 2.0 g (52.9 mmol) of sodium borohydride and the mixture was stirred at room temperature overnight. The reaction mixture was quenched with water, and extracted twice with dichloromethane. The combined organic layer was concentrated in vacuo to give 6.4 g of 4-hydroxy-cyclohexanecarbonitrile as a mixture of cis/trans isomers in a purity sufficient for further conversion. $R_t$=0.14 min (Method 18). Detected mass: 126.1 (M+H$^+$).

b) 4-(tert-Butyl-dimethyl-silanyloxy)-cyclohexanecarbonitrile (122)

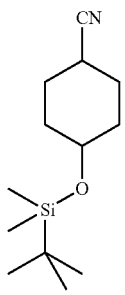

6.4 g (51.1 mmol) of 4-hydroxy-cyclohexanecarbonitrile (121) were dissolved in 120 mL of dichloromethane, cooled to 0° C. and 14.9 mL (13.7 g, 128 mmol) of 2,6-lutidine and 15.4 mL (14.9 g, 56.2 mmol) of tert-butyldimethylsilyltrifluoromethanesulfonate were added. The reaction mixture was stirred for 16 h at room temperature, then additional 5.0 mL of tert-butyldimethylsilyltrifluoromethanesulfonate were added and stirring continued for 1 h. The reaction mixture was diluted with 100 mL of dichloromethane and washed with 100 mL of water, 80 mL of saturated aqueous sodium bicarbonate solution and 50 mL of brine. The organic phase was dried over magnesium sulphate, filtered, concentrated in vacuo and purified by silica gel chromatography (heptanes:ethyl acetate) to give 9.76 g of the desired product. $R_t$=0.95 min (Method 18). Detected mass: 240.1 (M+H$^+$).

c) 4-(Amino-phenyl-methyl)-cyclohexanol (123)

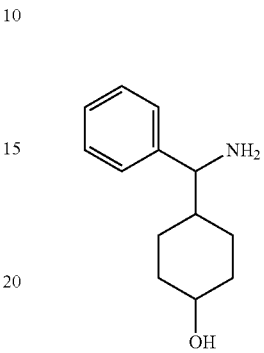

417 mg of 4-(Amino-phenyl-methyl)-cyclohexanol (123) as mixture of diastereoisomers was synthesized using the sequence described for the synthesis of 93, starting from 700 mg of 4-(tert-butyl-dimethyl-silanyloxy)-cyclohexanecarbonitrile (122) and 2.09 mL (5.85 mmol) of phenylmagnesium bromide. $R_t$=0.43 min (Method 18). Detected mass: 206.1 (M+H$^+$).

d) 6-[4-(amino-phenyl-methyl)-cyclohexyloxy]-7-chloro-2H-isoquinolin-1-one (Example 40)

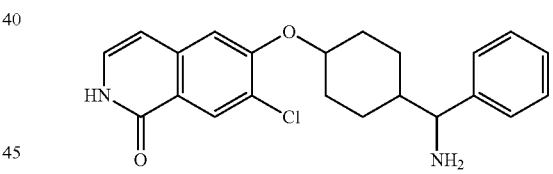

Example 40 was synthesized using the reaction sequence as described for the synthesis of Example 1. 240 mg of 4-(amino-phenyl-methyl)-cyclohexanol (123) and 272 mg of 7-chloro-6-fluoro-1-methoxy-isoquinoline (10) were used to give 51 mg of Example 40 as its hydrochloride. $R_t$=1.34 min (Method 10). Detected mass: 383.1 (M+H$^+$). 28 mg of the other isomer of 4-(amino-phenyl-methyl)-cyclohexanol (Example 128) were also isolated as its hydrochloride. $R_t$=1.31 min (Method 10). Detected mass: 383.1 (M+H$^+$). Separation of the two isomers was accomplished by silica gel chromatography after coupling of aminoalcohol 123 and 10. Relative stereochemistry was not assigned.

The following examples were obtained in a similar fashion as described for the alternative preparation of Example 40, using the corresponding isoquinolines and 4-(amino-methyl)-cyclohexanols (prepared following the sequence described for the synthesis of 123) as starting materials:

| Ex.-No. | Product | Chemical Name | [M + H]⁺ | Isomer | R$_t$/[min] | Method |
|---|---|---|---|---|---|---|
| 129 | | 6-[4-(1-Amino-propyl)-cyclohexyoxy]-7-chloro-2H-isoquinolin-1-one | 335.1 | 1 | 1.24 | 10 |
| 130 | | 6-[4-(1-Amino-propyl)-cyclohexyloxy]-7-chloro-2H-isoquinolin-1-one | 335.1 | 2 | 1.19 | 10 |
| 131 | | 6-[4-(Amino-cyclopropyl-methyl)-cyclohexyloxy]-7-chloro-2H-isoquinolin-1-one | 347.2 | 1 | 2.38 | 2 |
| 132 | | 6-[4-(Amino-cyclopropyl-methyl)-cyclohexyloxy]-7-chloro-2H-isoquinolin-1-one | 347.2 | 2 | 2.36 | 2 |

The following racemates were separated by HPLC, using a chiral column. Absolute stereochemistry was not determined, the earlier eluting enantiomer was designated to be enantiomer one. In case of Example 41 and Example 42, enantiomeric separation was performed on stage of the racemic O-benzyl protected precursor (1-[trans-4-(1-benzyloxy-7-chloro-isoquinolin-6-yloxy)-1-phenyl-cyclohexyl]-1-phenyl-methylamine) and the final products were liberated after separation, using the standard procedure described above. In the case of Example 41 and Example 42, data for retention times is given for said protected compounds.

| Example | Racemate | Enantiomer | Method | R$_t$ chiral [min] |
|---|---|---|---|---|
| 41 | 21 | 1 | B | 6.84 |
| 42 | 21 | 2 | B | 9.01 |
| 43 | 01 | 1 | A | 6.18 |
| 44 | 01 | 2 | A | 9.22 |
| 45 | 03 | 1 | A | 4.98 |
| 46 | 03 | 2 | A | 7.05 |
| 47 | 26 | 1 | A | 6.24 |
| 48 | 26 | 2 | A | 8.87 |
| 49 | 24 | 1 | A | 4.56 |
| 50 | 24 | 2 | A | 7.96 |
| 51 | 37 | 1 | C | 5.53 |
| 52 | 37 | 2 | C | 8.12 |
| 53 | 32 | 1 | A | 11.60 |
| 54 | 32 | 2 | A | 15.03 |

The enantiomers obtained from these examples by separation of the racemate are trans-6-[4-((S)-Amino-phenyl-methyl)-4-phenyl-cyclohexyloxy]-7-chloro-2H-isoquinolin-1-one,
trans-6-[4-((R)-Amino-phenyl-methyl)-4-phenyl-cyclohexyloxy]-7-chloro-2H-isoquinolin-1-one,
cis-6-[4-((S)-1-Amino-propyl)-4-phenyl-cyclohexyloxy]-7-chloro-2H-isoquinolin-1-one,
cis-6-[4-((R)-1-Amino-propyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((S)-1-Amino-ethyl)-4-phenyl-cyclohexyloxy]-7-chloro-2H-isoquinolin-1-one, cis-6-[4-((R)-1-Amino-ethyl)-4-phenyl-cyclohexyloxy]-7-chloro-2H-isoquinolin-1-one,
6-{4-[(S)-Amino-(4-fluoro-phenyl)-methyl]-cyclohexyloxy}-7-chloro-2H-isoquinolin-1-one,
6-{4-[(R)-Amino-(4-fluoro-phenyl)-methyl]cyclohexyloxy}-7-chloro-2H-isoquinolin-1-one,
cis-6-[4-((R)-1-Amino-propyl)-4-phenyl-cyclohexyloxy]-7-chloro-2H-isoquinolin-1-one, and
cis-6-[4-((S)-1-Amino-propyl)-4-phenyl-cyclohexyloxy]-7-chloro-2H-isoquinolin-1-one.
(enantiomers have not been assigned to "Enantiomer 1" or "Enantiomer 2", respectively)

LC/MS-Methods:

Method 1:

| Stationary phase: | Waters XBridge C18 |
|---|---|
| Gradient: | ACN + 0.05% TFA:H$_2$O + 0.05% TFA |
| | 5:95(0 min) to 5:95(0.3 min) to 95:5(3.5 min) to 95:5(4 min) |
| Flow: | 1.3 mL/min |

Method 2:

| Stationary phase: | Col YMC Jsphere 33 × 2.1 |
|---|---|
| Gradient: | ACN + 0.05% TFA:H$_2$O + 0.05% TFA |
| | 2:98(0 min) to 2:98(1 min) to 95:5(5 min) to 95:5(6.25 min) |
| Flow: | 1 mL/min |

Method 3:

| Stationary phase: | Waters XBridge C18 |
|---|---|
| Gradient: | ACN + 0.1% FA:H$_2$O + 0.1% FA |
| | 3:97(0 min) to 60:40(3.5 min) to 98:2(4.0 min) to 98:2(5.0 min) to 3:97(5.2 min) to 3:97(6.5 min) |
| Flow: | 1.3 mL/min |

Method 4:

| Stationary phase: | YMCJsphere H80, 33 × 2 |
|---|---|
| Gradient: | H$_2$O + 0.1% FA:ACN + 0.08% FA |
| | 95:5 (0 min) to 5:95(2.5 min) to 5:95(3 min) |
| Flow: | 1.3 mL/min |

Method 5

| Stationary phase: | Col YMC Jsphere ODS H80 20 × 2 |
|---|---|
| Gradient: | ACN:H$_2$O + 0.05% TFA |
| | 4:96(0 min) to 95:5(2.0 min) to 95:5(2.4 min) |
| Flow: | 1 mL/min |

Method 6:

| Stationary phase: | WatersXBridge C18 |
|---|---|
| Gradient: | H$_2$O + 0.1% FA:ACN + 0.08% FA |
| | 97:3(0 min) to 40:60(3.5 min) to 2:98(4 min) to 2:98 (5 min) to 97:3(5.2 min) to 97:3(6.5 min) |
| Flow: | 1.3 mL/min |

Method 7:

| Stationary phase: | Column Acquity BEH C18, 50 × 2.1 mm, 1.7 μm |
|---|---|
| Gradient: | H$_2$O + 0.05% TFA:ACN + 0.035% TFA |
| | 98:2(0 min) to 0:100(1.6 min) to 0:100(2.1 min) to 98:2(3 min) |
| Flow: | 1 mL/min |

Method 8:

| Stationary phase: | Column Gemini C18, 30 × 4.6 mm, 3 μm |
|---|---|
| Gradient: | H$_2$O + 0.1% FA:ACN + 0.1% FA |
| | 95:5(0 min) to 0:100(5.5 min) to 0:100(7.5 min) |
| Flow: | 1 mL/min |

Method 9:

| Stationary phase: | Column Gemini C18, 30 × 4.6 mm, 3 μm |
|---|---|
| Gradient: | H$_2$O + 0.1% FA:ACN + 0.1% FA |
| | 95:5(0 min) to 95:5(1 min) to 0:100(9 min) to 0:100(12 min) |
| Flow: | 1 mL/min |

Method 10:

| Stationary phase: | Merck Chromolith fast Grad |
|---|---|
| Gradient: | H$_2$O + 0.05% TFA:ACN + 0.035% TFA |
| | 98:2(0 min) to 98:2(0.2 min) to 2:98 (2.4 min) to 2:98 (3.2 min) to 98:2(3.3 min) to 98:2(4 min) |
| Flow: | 2 mL/min |

Method 11:

| Stationary phase: | Waters Aquity SDS |
|---|---|
| Gradient: | H$_2$O + 0.1% FA:ACN + 0.08% FA |
| | 95:5(0 min) to 5:95(1.1 min) to 5:95 (1.7 min) to 95:5 (1.8 min) to 95:5(2.0 min) |
| Flow: | 0.9 mL/min |

Method 12:

| Stationary phase: | WatersXBridge C18 |
|---|---|
| Gradient: | H$_2$O + 0.05% TFA:ACN + 0.05% TFA |
| | 95:5(0 min) to 95:5(0.2 min) to 5:95(2.4 min) (3.5 min) to 95:5(3.6 min) to 95:5(4.5 min) |
| Flow: | 1.7 mL/min |

Method 13:

| Stationary phase: | WatersXBridge C18 |
|---|---|
| Gradient: | H$_2$O + 0.05% TFA:ACN + 0.05% TFA |
| | 95:5(0 min) to 95:5(0.2 min) to 5:95(2.4 min) (3.2 min) to 95:5(3.3 min) to 95:5(4.0 min) |
| Flow: | 1.7 mL/min |

Method 14:

| Stationary phase: | WatersXBridge C18 |
|---|---|
| Gradient: | H₂O + 0.05% TFA:ACN + 0.05% TFA |
| | 95:5(0 min) to 95:5(0.1 min) to 5:95(3.3 min) to |
| | 95:5(3.85 min) to 95:5(4.3 min) |
| Flow: | 1.7 mL/min |

Method 15:

| Stationary phase: | Luna 3μ C18(2) 10 × 2.0 mm |
|---|---|
| Gradient: | ACN:H₂O + 0.05% TFA |
| | 7:93(0 min) to 95:5(1.2 min) to 95:5(1.4 min) |
| Flow: | 1.1 mL/min |

Method 16:

| Stationary phase: | Merck Chromolith fast Grad |
|---|---|
| Gradient: | H₂O + 0.05% TFA:ACN + 0.05% TFA |
| | 98:2(0 min) to 98:2(0.2 min) to 2:98 (2.4 min) to 2:98 |
| | (3.2 min) to 98:2(3.3 min) to 98:2(4 min) |
| Flow: | 2.4 mL/min |

Method 17:

| Stationary phase: | Luna 3μ C18(2) 10 × 2.0 mm (????) |
|---|---|
| Gradient: | ACN:H₂O + 0.05% TFA |
| | 20:80(0 min) to 95:5(0.8 min) to 95:5(1.4 min) to |
| | 20:80(1.45 min) |
| Flow: | 1.1 mL/min |

Method 18:

| Stationary phase: | Luna 3μ C18(2) 10 × 2.0 mm |
|---|---|
| Gradient: | ACN:H₂O + 0.05% TFA |
| | 7:93(0 min) to 95:5(1.2 min) to 95:5(1.4 min) to |
| | 7:93(1.45 min) |
| Flow: | 1.1 mL/min |

Method 19:

| Stationary phase: | Col YMC Jsphere ODS H80 20 × 2 |
|---|---|
| Gradient: | ACN:H₂O + 0.05% TFA |
| | 4:96(0 min) to 95:5(2.0 min) to 95:5(2.4 min) to |
| | 4:96 (2.45 min) |
| Flow: | 1 mL/min |

Method 20:

| Stationary phase: | WatersXBridge C18, 4.6, 6 × 50 2.5μ |
|---|---|
| Gradient: | Water + 0.05% TFA:ACN + 0.05% TFA |
| | 95:5(0 min) to 5:95(2.6 min) to 5:95(3.0 min) to |
| | 95:5(3.10 min) to 95:5 (4 min) |
| Flow | 1.7 mL/min |

Method 21:

| Stationary phase: | WatersXBridge C18, 4.6, 6 × 50 2.5μ |
|---|---|
| Gradient: | Water + 0.05% TFA:ACN + 0.05% TFA |
| | 95:5(0 min) to 95:5(0.2 min) to 5:95(2.4 min) to |
| | 5:95(3.5 min) to 95:5(3.6 min) to 95:5(4.5 min) |
| Flow | 1.7 mL/min |

Methods for Chiral Resolution

Method A:

| Stationary phase: | Chiralpak AD-H, 250 × 4.6 mm |
|---|---|
| Eluent: | MeOH:iPrOH 2:1 + 0.1% diethylamine |
| Flow: | 1 mL/min |
| Detection: | 249 nM |

Method B:

| Stationary phase: | Chiralpak AD-H, 250 × 4.6 mm |
|---|---|
| Eluent: | Heptane:EtOH:MeOH (5:1:1), column preconditioned with 0.1% diethylamine |
| Flow: | 1 mL/min |
| Detection: | 249 nM |

Method C:

| Stationary phase: | Chiralpak AD-H, 250 × 4.6 mm. |
|---|---|
| Eluent: | MeOH:EtOH (1:1) + 0.1% diethylamine. |
| Flow: | 1 mL/min |
| Detection: | 249 nM |

Determination of Rho Kinase Inhibition

To measure Rho-kinase inhibition, $IC_{50}$ values were determined according to the following protocol:

Active human recombinant ROCK II (N-terminal His6-tagged recombinant human ROCK-II residues 11-552) was purchased from Millipore GmbH, Schwalbach, Germany. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35, dithiothreitol (DTT) and Pluronic F-68 were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl2, 2 mM DTT, 0.02% (w/v) BSA, 0.01% Pluronic F-68 and 3% DMSO). The ROCK II enzyme was diluted to a concentration of 100 ng/mL in buffer 2 (25 mM Tris-HCl, pH 7.4, 5 mM MgCl2, 2 mM DTT and 0.02% (w/v) BSA). The peptide substrate and ATP were diluted to concentrations of 3 μM and 120 μM, respectively, in the buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure −1.3 psi, upstream voltage −1562 V, downstream voltage −500 V, sample sip time 200 ms. Positive controls (buffer 1 instead of compound) and negative controls (buffer 1 instead of compound and buffer 2 instead of ROCK II) were run in parallel on each plate.

The following products/compounds were tested in said assay by using the respective form (salt or free base) obtained as in the examples described above and the following activities were measured

| Example No. | pIC50 |
|---|---|
| 1 | +++++++ |
| 2 | +++++++ |
| 3 | +++++++ |
| 4 | +++++++ |
| 5 | +++++++ |
| 6 | +++++++ |
| 7 | +++++++ |
| 8 | +++++++ |
| 9 | +++++++ |
| 10 | +++++++ |
| 11 | ++++++ |
| 12 | +++++ |
| 13 | ++++++ |
| 14 | +++++ |
| 15 | +++++++ |
| 16 | ++++++ |
| 17 | ++++++ |
| 19 | +++++ |
| 20 | ++++++ |
| 22 | ++++++ |
| 24 | +++++++ |
| 25 | +++++++ |
| 26 | +++++++ |
| 27 | ++++++ |
| 28 | +++++++ |
| 29 | +++++++ |
| 31 | ++++++ |
| 32 | ++++++ |
| 34 | ++++++ |
| 35 | +++++++ |
| 36 | ++++++ |
| 37 | +++++++ |
| 38 | +++++++ |
| 39 | ++++++ |
| 40 | +++++ |
| 41 | +++++ |
| 42 | ++++++ |
| 44 | +++++++ |
| 45 | +++++++ |
| 46 | +++++++ |
| 51 | +++++ |
| 52 | +++++++ |
| 53 | ++++++ |
| 54 | +++++ |
| 55 | +++++++ |
| 56 | +++++++ |
| 57 | +++++++ |
| 58 | +++++++ |
| 59 | +++++++ |
| 60 | +++++++ |
| 61 | +++++ |
| 62 | +++++++ |
| 63 | +++++++ |
| 64 | +++++++ |
| 65 | +++++ |
| 66 | +++++ |
| 67 | +++++ |
| 69 | +++++++ |
| 70 | +++++++ |
| 77 | +++++++ |
| 82 | +++++++ |
| 83 | +++++ |
| 84 | +++++ |
| 85 | +++++ |
| 86 | +++++ |
| 87 | ++++++ |
| 88 | +++++ |
| 89 | +++++ |
| 90 | +++++ |
| 92 | +++++ |
| 94 | +++++ |
| 97 | +++++++ |
| 99 | +++++++ |
| 100 | +++++++ |
| 101 | +++++ |
| 109 | ++++++ |
| 110 | ++++++ |
| 111 | ++++++ |
| 114 | +++++++ |
| 115 | +++++ |
| 116 | ++++++ |
| 117 | ++++++ |
| 118 | +++++ |
| 119 | +++++ |
| 120 | +++++ |
| 121 | ++++++ |
| 122 | ++++++ |
| 123 | ++++++ |
| 124 | ++++++ |
| 125 | +++++ |
| 126 | +++++ |
| 128 | +++++ |
| 129 | ++++++ |
| 130 | ++++++ |
| 131 | +++++ |

The given activity is denoted as the negative decadal logarithm of the $IC_{50}$ ($pIC_{50}$) as follows:

+: $pIC50 \leq 3.0$
++: $3.0 \leq pIC_{50} < 4.0$
+++: $4.0 \leq pIC_{50} < 5.0$
++++: $5.0 \leq pIC_{50} < 6.0$
+++++: $6.0 \leq pIC50 < 7.0$
++++++: $7.0 \leq pIC50 < 8.0$
+++++++: $8.0 \leq pIC50$ Determination of Protein Kinase A and Protein Kinase G Inhibition To measure PKA and PKG1-beta inhibition, $IC_{50}$ values were determined according to the following protocol:

Active recombinant human PKG1-beta (full-length, with N-terminal His-tag) was purchased from Millipore GmbH, Schwalbach, Germany. Active recombinant human PKA (residues 1-351, N-terminal His-tag) was obtained from Invitrogen, Karlsruhe, Germany. The peptide substrate, Fluorescein-AKRRRLSSLRA-COOH, was obtained from JPT Peptide Technologies, Berlin, Germany. Adenosine-5'-triphosphate (ATP), bovine serum albumine (BSA), dimethylsulphoxide (DMSO), 4-(2-Hydroxyethyl)piperazine-1-ethanesulfonic acid (Hepes), Brij-35, dithiothreitol (DTT) and Pluronic F-68 were purchased from Sigma-Aldrich, Munich, Germany. Tris(hydroxymethyl)-aminomethane (Tris), magnesium chloride, NaOH, 1M HCl and EDTA were obtained from Merck Biosciences, Darmstadt, Germany. "Complete" protease inhibitor was from Roche Diagnostics, Mannheim, Germany.

Test compounds were diluted to the appropriate concentrations in buffer 1 (25 mM Tris-HCl, pH 7.4, 5 mM MgCl2, 2 mM DTT, 0.02% (w/v) BSA, 0.01% Pluronic F-68 and 3% DMSO). PKG1-beta and PKA were diluted to concentrations of 150 ng/ml and 30 ng/ml, respectively, in buffer 2. The peptide substrate and ATP were diluted to concentrations of 3 µM and 120 µM, respectively, in the buffer 2. Two µl of the compound solution were mixed with 2 µl of the diluted enzyme in a 384-well small volume microtiter plate (Greiner, Bio-One, Frickenhausen, Germany), and the kinase reaction was initiated by addition of 2 µl of the solution containing peptide substrate and ATP. After 60 min incubation at 32° C., the reaction was stopped by addition of 20 µl of a solution containing 100 mM Hepes-NaOH, pH 7.4, 0.015% (v/v) Brij-35, 45 mM EDTA and 0.227% chip coating reagent 1 (Caliper Lifescience Inc, Hopkinton, Mass.). Phosphorylation of the substrate peptide was then detected on a Caliper 3000 instrument essentially as described by Pommereau et al (J. Biomol. Screening 9(5), 409-416, 2004). Separation conditions were as follows: Pressure −1.3 psi, upstream voltage −1562 V, downstream voltage −500 V, sample sip time 200 ms. Positive controls (buffer 1 instead of compound) and negative controls (buffer 1 instead of compound and buffer 2 instead of kinase solution) were run in parallel on each plate. The following products/compounds were tested in said assay by using the respective form (salt or free base) obtained as in the examples described above and the following activities were measured.

| Example No. | Selectivity against PKA | Selectivity against PKG |
| --- | --- | --- |
| 1 | >1000 | >1000 |
| 2 | >1000 | >1000 |
| 3 | >1000 | >300 |
| 4 | >1000 | >100 |
| 5 | >1000 | >300 |
| 6 | >1000 | >300 |
| 7 | >1000 | >300 |
| 8 | >1000 | >300 |
| 9 | >1000 | >100 |
| 10 | >100 | >100 |
| 11 | >300 | >10 |
| 12 | >100 | >10 |
| 13 | >300 | >100 |
| 14 | >100 | >100 |
| 15 | >1000 | >300 |
| 16 | >300 | >100 |
| 17 | >300 | >100 |
| 19 | >100 | >100 |
| 20 | >100 | >100 |
| 22 | >300 | >100 |
| 24 | >1000 | >300 |
| 25 | >1000 | >100 |
| 26 | >1000 | >300 |
| 27 | >100 | >10 |
| 28 | >1000 | >1000 |
| 29 | >1000 | >1000 |
| 31 | >300 | >100 |
| 32 | >1000 | >300 |
| 34 | >300 | >10 |
| 35 | >1000 | >100 |
| 36 | >300 | >300 |
| 37 | >1000 | >300 |
| 38 | >1000 | >300 |
| 39 | >100 | >100 |
| 41 | >10 | >10 |
| 42 | >300 | >300 |
| 44 | >1000 | >1000 |
| 45 | >1000 | >100 |
| 46 | >1000 | >1000 |
| 51 | >100 | >10 |
| 52 | >1000 | >300 |
| 53 | >100 | >100 |
| 55 | >1000 | >300 |
| 56 | >1000 | >300 |
| 57 | >1000 | >300 |
| 58 | >1000 | >100 |
| 59 | >1000 | >300 |
| 60 | >1000 | >100 |
| 61 | >10 | >1 |
| 62 | >1000 | >300 |
| 63 | >1000 | >300 |
| 64 | >1000 | >100 |
| 66 | >10 | >10 |
| 69 | >1000 | >300 |
| 70 | >1000 | >1000 |
| 77 | >1000 | >300 |
| 82 | >1000 | >1000 |
| 83 | >100 | >10 |
| 84 | >100 | >10 |
| 85 | >100 | >10 |
| 86 | >10 | >10 |
| 87 | >1000 | >100 |
| 88 | >10 | >10 |
| 97 | >1000 | >300 |
| 99 | >1000 | >100 |
| 100 | >1000 | >1000 |
| 109 | >300 | >100 |
| 110 | >300 | >100 |
| 114 | >1000 | >1000 |
| 116 | >100 | >10 |
| 117 | >300 | >10 |
| 120 | >100 | >10 |
| 121 | >100 | >10 |
| 122 | >300 | >10 |
| 123 | >100 | >10 |
| 124 | >100 | >10 |
| 125 | >10 | >10 |
| 128 | >10 | >10 |
| 129 | >100 | >10 |
| 130 | >300 | >10 |
| 131 | >10 | >10 |
| 132 | >100 | >10 |

The invention claimed is:
1. A compound of the formula (I)

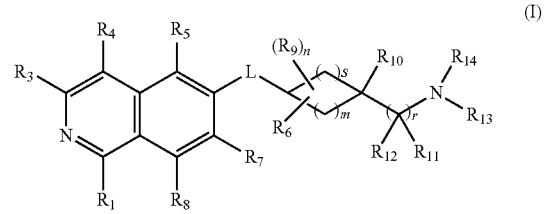

wherein
$R_1$ is H, OH or $NH_2$;
$R_3$ is H, halogen, CN, $(C_1-C_6)$alkyl, OH, $NH_2$, or NHR';
$R_4$ is H, halogen, hydroxy, CN, $(C_1-C_6)$alkyl, R', or $(C_1-C_6)$alkylene-R';
$R_5$ is H, halogen, CN, $(C_1-C_6)$alkyl, or R';
$R_7$ is H, halogen, CN, $(C_1-C_6)$alkyl, O—$(C_1-C_6)$alkyl, R', or $SO_2$—$NH_2$;
$R_8$ is H, halogen or $(C_1-C_6)$alkyl;
$R_9$ is
R',
OH,
halogen,
$(C_1-C_6)$alkyl,
O—$(C_1-C_6)$alkyl,
$(C_1-C_6)$alkylene-R',
$(C_2-C_6)$alkenyl, ($C_2$-$C_6$)alkynyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$;
($C_1$-$C_6$)alkylene-C(O)O—($C_1$-$C_6$)alkyl,
COOH,
C(O)O—($C_1$-$C_6$)alkyl,
C(O)OR'
C(O)($C_1$-$C_6$)alkyl,
C(O)R',
C(O)NH$_2$,
C(O)—NH—($C_2$-$C_6$)alkenyl,
C(O)—NH—($C_2$-$C_6$)alkynyl,
C(O)NH—($C_1$-$C_6$)alkyl,
C(O)NHR',
C(O)—NH($C_1$-$C_6$)alkylene-R',
C(O)N[($C_1$-$C_6$)alkyl]R'
C(O)N[($C_1$-$C_6$)alkyl]$_2$,
C(O)—($C_1$-$C_6$)alkylene-R', or
C(O)O($C_1$-$C_6$)alkylene-R';
$R_6$ is absent;
or is one ($C_1$-$C_4$)alkylene bound to the cycloalkyl ring, in which the ($C_1$-$C_4$)alkylene forms a second bond to a different carbon atom of the cycloalkyl ring to form a bicyclic ring system, wherein in the bicyclic ring system optionally one or two carbon atomes are replaced by a group independently selected from O, N—$R_{15}$, S, SO or SO$_2$;
or, if m; and s are 2, m is 3 and s is 1, or m is 4 and s is 0, $R_6$ is CH$_2$—CH—(CH$_2$)$_2$ which is bound with one CH$_2$ to the cycloalkyl ring and the two other CH$_2$ are bound to different carbon atoms of the cycloalkyl ring;
and, if m is 3 and s is 3,
$R_6$ are two methylene groups bound to different carbon atoms of the cycloalkyl ring, wherein the methylene groups or the CH$_2$—CH—(CH$_2$)$_2$ group are bound to carbon atoms of the cycloaalkyl ring such that they form an adamantane system of the formula

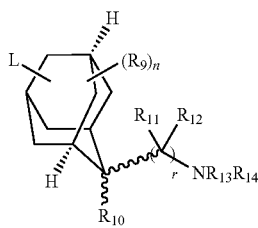

wherein L can be bound to any secondary or tertiary carbon atom and
wherein the bicyclic ring system or adamantane system is unsubstituted or optionally substituted by $R_9$;
$R_{10}$ is
H,
($C_6$-$C_{10}$)aryl,
O—($C_6$-$C_{10}$)aryl,
O—($C_1$-$C_6$)alkylene-($C_6$-$C_{10}$)aryl, or
($C_5$-$C_{10}$)heteroaryl, wherein ($C_6$-$C_{10}$)aryl or ($C_5$-$C_{10}$)heteroaryl are unsubstituted or substituted;

$R_{11}$ is
H,
($C_1$-$C_6$)alkyl,
($C_1$-$C_6$)alkylene-R',
($C_3$-$C_8$)cycloalkyl,
($C_5$-$C_{10}$)heteroaryl,
($C_3$-$C_8$)heterocycloalkyl,
($C_6$-$C_{10}$)aryl;
or $R_{11}$ and $R_{12}$ together with carbon atom to which they are attached form a ($C_3$-$C_8$)cycloalkyl or a ($C_3$-$C_8$)-heterocycloalkyl ring;
$R_{12}$ is
($C_1$-$C_6$)alkyl,
($C_3$-$C_8$)cycloalkyl,
($C_5$-$C_{10}$)heteroaryl,
($C_3$-$C_8$)heterocycloalkyl, or
($C_6$-$C_{10}$)aryl;
or $R_{12}$ is H, provided that r=2 and the other $R_{12}$ is not H;
or $R_{11}$ and $R_{12}$ together with carbon atom to which they are attached form a ($C_3$-$C_8$)cycloalkyl or a ($C_3$-$C_8$)-heterocycloalkyl ring;
$R_{13}$ and $R_{14}$ are independently of each other
H,
R',
($C_1$-$C_6$)alkyl,
($C_1$-$C_6$)alkylene-R',
($C_1$-$C_6$)alkylene-O—($C_1$-$C_6$)alkyl,
($C_1$-$C_6$)alkylene-O—R',
($C_1$-$C_6$)alkylene-CH[R']$_2$,
($C_1$-$C_6$)alkylene-C(O)—R',
($C_1$-$C_6$)alkylene-C(O)NH$_2$,
($C_1$-$C_6$)alkylene-C(O)NH—R',
($C_1$-$C_6$)alkylene-C(O)NH—($C_1$-$C_6$)alkyl,
($C_1$-$C_6$)alkylene-C(O)N[($C_1$-$C_6$)alkyl]$_2$,
($C_1$-$C_6$)alkylene-C(O)N[R']$_2$,
($C_1$-$C_6$)alkylene-C(O)O—($C_1$-$C_6$)alkyl,
C(O)O—($C_1$-$C_6$)alkyl,
C(O)OR',
C(O)($C_1$-$C_6$)alkyl,
C(O)R',
C(O)NH—($C_1$-$C_6$)alkyl,
C(O)NHR',
C(O)N [($C_1$-$C_6$)alkyl]R'
C(O)N[($C_1$-$C_6$)alkyl]$_2$,
C(O)—($C_1$-$C_6$)alkylene-R',
C(O)O($C_1$-$C_6$)alkylene-R', or
$R_{13}$ and $R_{14}$, together with the N-atom to which they are attached, form a ($C_3$-$C_8$) heterocycloalkyl;
$R_{15}$ is H or ($C_1$-$C_6$)alkyl;
n is 0, 1, 2, 3 or 4;
m is 1, 2, 3 or 4;
s is 0, 1, 2, or 3;
r is 1 or 2;
L is O(CH$_2$)$_p$, S(CH$_2$)$_p$, S(O)(CH$_2$)$_p$, SO$_2$(CH$_2$)$_p$, NH(CH$_2$)$_p$, N($C_1$-$C_6$)alkyl-(CH$_2$)$_p$, N($C_3$-$C_6$)cycloalkyl-(CH$_2$)$_p$; or N[($C_1$-$C_3$)alkylene-R]-(CH$_2$)$_p$;
p is 0, 1, 2, 3 or 4;
R' is
($C_3$-$C_8$)cycloalkyl,
($C_5$-$C_{10}$)heteroaryl,
($C_3$-$C_8$)heterocycloalkyl,
($C_6$-$C_{10}$)aryl;
wherein in residues $R_3$ to $R_{15}$ alkyl or alkylene is unsubstituted or optionally substituted one or more times by OH, OCH$_3$, C(O)OH, C(O)OCH$_3$, NH$_2$, NHCH$_3$, N(CH$_3$)$_2$, C(O)NH$_2$, C(O)NHCH$_3$ or C(O)N(CH$_3$)$_2$;
wherein in residues $R_3$ to $R_{15}$ cycloalkyl or heterocycloalkyl is unsubstituted or optionally substituted one or more times by $(C_1-C_6)$alkyl, halogen, OH, OCH$_3$, C(O) OH, C(O)OCH$_3$, NH$_2$, NHCH$_3$, N(CH$_3$)$_2$, C(O)NH$_2$, C(O)NHCH$_3$ or C(O)N(CH$_3$)$_2$;

wherein in residues $R_3$ to $R_{15}$ alkyl or alkylene is unsubstituted or optionally substituted one or more times by halogen;

wherein in residues $R_3$ to $R_{15}$ $(C_6-C_{10})$aryl and $(C_5-C_{10})$heteroaryl are unsubstituted or optionally substituted one or more times by a group independently selected from halogen, OH, NO$_2$, N$_3$, CN, C(O)—$(C_1-C_6)$alkyl, C(O)—$(C_6-C_{10})$aryl, COOH, COO$(C_1-C_6)$alkyl, CONH$_2$, CONH$(C_1-C_6)$alkyl, CON[$(C_1-C_6)$alkyl]$_2$, $(C_3-C_8)$cycloalkyl, $(C_1-C_6)$alkyl, $(C_1-C_6)$alkylene-NH$(C_1-C_6)$alkyl, $(C_1-C_6)$alkylene-N[$(C_1-C_6)$alkyl]$_2$, $(C_2-C_6)$alkenyl, $(C_2-C_6)$alkynyl, O—$(C_1-C_6)$alkyl, O—C(O)—$(C_1-C_6)$alkyl, PO$_3$H$_2$, SO$_3$H, SO$_2$—NH$_2$, SO$_2$NH$(C_1-C_6)$alkyl, SO$_2$N[$(C_1-C_6)$alkyl]$_2$, S—$(C_1-C_6)$alkyl; SO—$(C_1-C_6)$alkyl, SO$_2$—$(C_1-C_6)$alkyl, SO$_2$—N=CH—N[$(C_1-C_6)$alkyl]$_2$, SF$_5$,
C(NH)(NH$_2$), NH$_2$, NH—$(C_1-C_6)$alkyl, [$(C_1-C_6)$alkyl]$_2$, NH—C(O)—$(C_1-C_6)$alkyl, NH—C(O)O—$(C_1-C_6)$alkyl, NH—SO$_2$—$(C_1-C_6)$alkyl, NH—SO$_2$—$(C_6-C_{10})$aryl, NH—SO$_2$—$(C_5-C_{10})$heteroaryl, NH—SO$_2$—$(C_3-C_8)$heterocycloalkyl, N$(C_1-C_6)$alkyl-C(O)—$(C_1-C_6)$alkyl, N$(C_1-C_6)$alkyl-C(O)O—$(C_1-C_6)$alkyl, N$(C_1-C_6)$alkyl-C(O)—NH—$(C_1-C_6)$alkyl], $(C_6-C_{10})$aryl, $(C_1-C_6)$alkylene-$(C_6-C_{10})$aryl, O—$(C_6-C_{10})$aryl, O—$(C_1-C_6)$alkylene-$(C_6-C_{10})$aryl, $(C_5-C_{10})$heteroaryl, $(C_3-C_8)$heterocycloalkyl,
$(C_1-C_6)$alkylene-$(C_5-C_{10})$heteroaryl, $(C_1-C_6)$alkylene-$(C_3-C_8)$heterocycloalkyl, O—$(C_1-C_6)$alkylene-$(C_5-C_{10})$heteroaryl, O—$(C_1-C_6)$alkylene-$(C_3-C_8)$heterocycloalkyl, wherein said $(C_6-C_{10})$aryl, $(C_5-C_{10})$heteroaryl, $(C_3-C_8)$heterocycloalkyl or $(C_3-C_8)$cycloalkyl may be substituted one to three times by a group independently selected from halogen, OH, NO$_2$, CN, O—$(C_1-C_6)$alkyl, $(C_1-C_6)$alkyl, NH$_2$, NH$(C_1-C_6)$alkyl, N[$(C_1-C_6)$alkyl]$_2$, SO$_2$CH$_3$, COOH, C(O)O—$(C_1-C_6)$alkyl, CONH$_2$, $(C_1-C_6)$alkylene-O—$(C_1-C_6)$alkyl, $(C_1-C_6)$alkylene-β-$(C_6-C_{10})$aryl, or O—$(C_1-C_6)$alkylene-$(C_6-C_{10})$aryl; or wherein $(C_6-C_{10})$aryl is vicinally substituted by a O—$(C_1-C_4)$alkylene-O group whereby a 5-8-membered ring is formed together with the carbon atoms the oxygen atoms are attached to; and wherein aryl substituents of $(C_6-C_{10})$aryl, $(C_5-C_{10})$hetero aryl, $(C_3-C_8)$heterocycloalkyl or $(C_3-C_8)$cycloalkyl groups may not be further substituted by an aryl, heteroaryl, heterocycloalkyl, or $(C_3-C_8)$cycloalkyl containing group;

their stereoisomeric and/or tautomeric forms or a pharmaceutically acceptable salt.

2. A compound of formula (I) according to claim 1, wherein R$_1$ is H and is characterized by the formula (II)

(II)

3. A compound of formula (I) according to claim 1, wherein R$_1$ is OH and is characterized by the formula (IIIa)

(IIIa)

or of the formula (IIIb)

(IIIb)

4. A compound according to claim 1, wherein R$_1$ is NH$_2$.

5. A compound according to one of claims 1 to 4, wherein R$_3$ is H, halogen, $(C_1-C_6)$alkyl, or NHR', wherein $(C_1-C_6)$alkyl and R' are unsubstituted or substituted.

6. A compound according to one of claims 1 to 4, wherein R$_3$ is H.

7. A compound according to one of claims 1 to 4, wherein R$_4$ is H, halogen, $(C_1-C_6)$alkyl or $(C_1-C_2)$alkylene-phenyl, wherein $(C_1-C_6)$alkyl or phenyl are unsubstituted or substituted.

8. A compound according to one of claims 1 to 4, wherein R$_4$ is H or halogen.

9. A compound according to one of claims 1 to 4, wherein R$_5$ is H, halogen, $(C_1-C_6)$alkyl, $(C_6-C_{10})$aryl, $(C_3-C_8)$cycloalkyl or $(C_5-C_{10})$hetero aryl, wherein $(C_1-C_6)$alkyl, $(C_6-C_{10})$aryl, $(C_3-C_8)$cycloalkyl or $(C_5-C_{10})$heteroaryl are unsubstituted or substituted.

10. A compound according to one of claims 1 to 4, wherein R$_5$ is H.

11. A compound according to one of claims 1 to 4, wherein R$_7$ is H, halogen, $(C_1-C_6)$alkyl, O—$(C_1-C_6)$alkyl, or R', wherein $(C_1-C_6)$alkyl or R' are unsubstituted or substituted.

12. A compound according to one of claims 1 to 4, wherein R$_7$ is H, methyl or chloro.

13. A compound according to one of claims 1 to 4, wherein R$_8$ is H.

14. A compound according to one of claims 1 to 4, wherein R$_9$ is
R',
OH,
halogen,
$(C_1-C_6)$alkyl,
$(C_1-C_6)$alkylene-R',
$(C_2-C_6)$alkenyl,
$(C_1-C_6)$alkylene-C(O)NH—R',
$(C_1-C_6)$alkylene-C(O)NH—$(C_1-C_6)$alkyl,
C(O)OH,
C(O)NH$_2$,
C(O)NH—$(C_1-C_6)$alkyl, C(O)NHR',
C(O)—NH—(C$_1$-C$_6$)alkynyl,
C(O)—NH(C$_1$-C$_6$)alkylene-R', or
C(O)N[(C$_1$-C$_6$)alkyl]$_2$;
wherein (C$_1$-C$_6$)alkyl, (C$_1$-C$_6$)alkylene or R' are unsubstituted or substituted.

15. A compound according to one of claims 1 to 4, wherein R$_9$ is OH, halogen, (C$_1$-C$_6$)alkyl, C(O)OH, C(O)NH$_2$, or O—CH$_3$, wherein (C$_1$-C$_6$)alkyl is unsubstituted or substituted.

16. A compound according to one of claims 1 to 4, wherein R$_9$ is unsubstituted or substituted (C$_1$-C$_6$)alkyl.

17. A compound according to any of claims 1 to 4, wherein R$_{10}$ is H, phenyl, O-phenyl, or (C$_5$-C$_6$)heteroaryl,
wherein phenyl or (C$_5$-C$_6$)heteroaryl is unsubstituted or substituted.

18. A compound according to any of claims 1 to 4, wherein R$_{10}$ is H or phenyl optionally substituted by (C$_1$-C$_6$)alkyl, F, Cl, Br, OMe or CF$_3$.

19. A compound according to any of claims 1 to 4, wherein R$_{10}$ is H.

20. A compound according to any of claims 1 to 4, wherein R$_{11}$ is H or methyl.

21. A compound according to any of claims 1 to 4, wherein R$_{12}$ is
(C$_1$-C$_6$)alkyl, wherein optionally one or more hydrogen are substituted by fluoro;
(C$_3$-C$_8$)cycloalkyl,
(C$_5$-C$_6$)heteroaryl, or
(C$_6$-C$_{10}$)aryl,
wherein (C$_3$-C$_8$)cycloalkyl, (C$_5$-C$_6$)heteroaryl or (C$_6$-C$_{10}$)aryl are unsubstituted or substituted.

22. A compound according to any of claims 1 to 4, wherein R$_{12}$ is methyl, ethyl, propyl, isopropyl, cyclopropyl, trifluoromethyl, thiazolyl or phenyl unsubstituted or substituted by (C$_1$-C$_4$)alkyl or halogen.

23. A compound according to any of claims 1 to 4, wherein R$_{11}$ and R$_{12}$ form a substituted or unsubstituted (C$_3$-C$_8$)cycloalkyl ring.

24. A compound according to one of claims 1 to 4, wherein R$_{13}$ and R$_{14}$ are independently of each other
H,
R'
(C$_1$-C$_6$)alkyl,
(C$_1$-C$_6$)alkylene-R',
(C$_1$-C$_6$)alkylene-O—(C$_1$-C$_6$)alkyl,
(C$_1$-C$_6$)alkylene-O—R',
C(O)(C$_1$-C$_6$)alkyl,
C(O)R', or
C(O)(C$_1$-C$_6$)alkyene-R'
C(O)N[(C$_1$-C$_6$)alkyl]$_2$,
wherein R', (C$_1$-C$_6$)alkyl, or (C$_1$-C$_6$)alkylene are unsubstituted or substituted, or
R$_{13}$ and R$_{14}$, together with the N-atom to which they are attached, form a unsubstituted or substituted (C$_3$-C$_8$) heterocycloalkyl ring.

25. A compound according to one of claims 1 to 4, wherein R$_{13}$ and R$_{14}$ are independently of each other
H,
(C$_1$-C$_6$)alkyl,
(C$_3$-C$_8$)cycloalkyl,
(C$_1$-C$_4$)alkylene-(C$_3$-C$_8$)cycloalkyl,
(C$_1$-C$_4$)alkylene-(C$_5$-C$_{10}$)heteroaryl,
(C$_1$-C$_4$)alkylene-(C$_3$-C$_8$)heterocycloalkyl,
C$_1$-C$_4$)alkylene-(C$_6$-C$_{10}$)aryl,
(C$_1$-C$_6$)alkylene-O—(C$_1$-C$_6$)alkyl,
C(O)(C$_1$-C$_6$)alkyl, or
R$_{13}$ and R$_{14}$, together with the N-atom to which they are attached, form a (C$_3$-C$_8$) heterocycloalkyl group,
wherein (C$_1$-C$_6$)alkyl, (C$_3$-C$_8$)cycloalkyl, (C$_1$-C$_4$)alkylene, (C$_5$-C$_{10}$)heteroaryl, (C$_3$-C$_8$)heterocycloalkyl, or (C$_6$-C$_{10}$)aryl are unsubstituted or substituted.

26. A compound according to any of claims 1 to 4, wherein R$_{13}$ is H or (C$_1$-C$_6$)alkyl; and
R$_{14}$ is
H,
(C$_1$-C$_6$)alkyl,
(C$_3$-C$_8$)cycloalkyl,
(C$_1$-C$_4$)alkylene-(C$_3$-C$_8$)cycloalkyl,
(C$_1$-C$_4$)alkylene-(C$_5$-C$_{10}$)heteroaryl,
(C$_1$-C$_4$)alkylene-(C$_3$-C$_8$)heterocycloalkyl,
(C$_1$-C$_4$)alkylene-(C$_6$-C$_{10}$)aryl, or
(C$_1$-C$_4$)alkylene-O—(C$_1$-C$_6$)alkyl,
wherein (C$_1$-C$_6$)alkyl, (C$_3$-C$_8$)cycloalkyl, (C$_1$-C$_4$)alkylene, (C$_5$-C$_{10}$)heteroaryl, (C$_3$-C$_8$)heterocycloalkyl, or (C$_6$-C$_{10}$)aryl are unsubstituted or substituted.

27. A compound according to any of claims 1 to 4, wherein R$_{13}$ is H, (C$_1$-C$_6$)alkyl and
R$_{14}$ is H, (C$_1$-C$_6$)alkyl or (C$_3$-C$_8$)cycloalkyl,
wherein (C$_1$-C$_6$)alkyl or (C$_3$-C$_8$)cycloalkyl are unsubstituted or substituted.

28. A compound according to any of claims 1 to 4, wherein R$_{13}$ and R$_{14}$ are H.

29. A compound according to one of claims 1 to 4, wherein R$_6$ is absent or the bicyclus or adamantane formed with R$_6$ is selected from

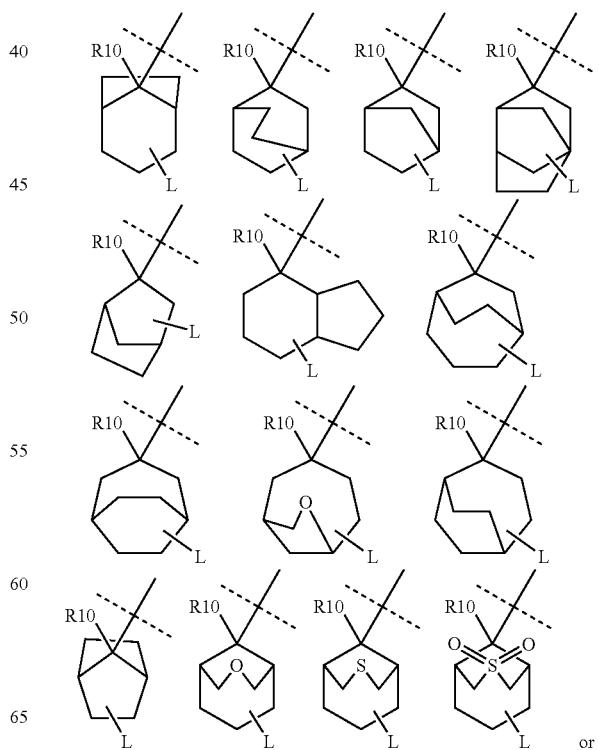

-continued

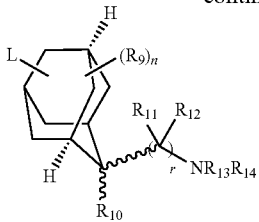

which are unsubstituted or optionally substituted by $R_9$.

30. A compound according to one of claims 1 to 4, wherein $R_6$ is absent.
31. A compound according to one of claims 1 to 4, wherein m is 2 and s is 2.
32. A compound according to one of claims 1 to 4, wherein m is 3 and s is 1.
33. A compound according to one of claims 1 to 4, wherein n is 0, 1, or 1.
34. A compound according to one of claims 1 to 4, wherein n is 0.
35. A compound according to one of claims 1 to 4, wherein r is 1.
36. A compound according to one of claims 1 to 4, wherein L is $S(CH_2)_p$, $S(O)(CH_2)p$, or $SO_2(CH_2)p$.
37. A compound according to one of claims 1 to 4, wherein L is $NH(CH_2)p$ or $N(C_1\text{-}C_6\text{alkyl})\text{-}(CH_2)p$.
38. A compound according to one of claims 1 to 4, wherein L is $O(CH_2)p$.
39. A compound according to one of claims 1 to 4, wherein p is 0.
40. A compound according to claim 1 selected from the group consisting of
    6-[4-(1-Amino-propyl)-4-(4-fluoro-phenyl)-cyclohexyloxy]-7-chloro-2H-isoquinolin-1-one,
    6-[4-(1-Amino-cyclopropyl)-4-phenyl-cyclohexyloxy]-7-chloro-2H-isoquinolin-1-one,
    6-{[4-(1-aminopropyl)-4-phenylcyclohexyl]oxy}-7-chloroisoquinolin-1(2H)-one,
    6-[4-(1-Amino-butyl)-4-phenyl-cyclohexyloxy]-7-chloro-2H-isoquinolin-1-one,
    6-[4-(1-Amino-butyl)-4-(4-fluoro-phenyl)-cyclo-hexyloxy]-7-chloro-2H-isoquinolin-1-one,
    6-[4-(1-Amino-propyl)-4-(4-bromo-phenye-cyclohexyloxy]-7-chloro-2H-isoquinolin-1-one,
    6-[4-(1-Amino-propyl)-4-(2-bromo-phenyl)-cyclohexyloxy]-7-chloro-2H-isoquinolin-1-one,
    6-[4-(1-Amino-propyl)-4-(4-trifluoromethyl-phenyl)-cyclo-hexyloxy]-7-chloro-2H-isoquinolin-1-one,
    6-[4-(1-Amino-propyl)-4-(2-fluoro-phenyl)-cyclohexyloxy]-7-chloro-2,1-isoquinolin-1-one,
    6-[4-(1-Amino-propyl)-4-(2-chloro-phenyl)-cyclohexyloxy]-7-chloro-2H-isoquinolin-1-one,
    6-[4-(1-Amino-propyl)-4-phenyl-cyclohexyloxy]-7-methyl-2H-isoquinolin-1-one,
    6-[4-(1-Amino-ethyl)-4-(4-fluoro-phenyl)-cyclo-hexyloxy]-7-chloro-2H-isoquinolin-1-one,
    6-[4-(1-Amino-2-methyl-propyl)-4-phenyl-cyclohexyloxy]-7-chloro-2H-isoquinolin-1-one,
    6-[4-(1-Amino-3-methyl-butyl)-4-phenyl-cyclohexyloxy]-7-chloro-2H-isoquinolin-1-one,
    6-[(Amino-phenyl-methyl)-4-phenyl-cyclo-hexyloxy]-7-chloro-2H-isoquinolin-1-one,
    6-[4-(1-Amino-1-methyl-ethyl)-4-(4-fluoro-phenyl)-cyclohexyloxy]-7-chloro-2H-isoquinolin-1-one,
    6-[4-(1-Amino-cyclopropyl)-4-(2-fluoro-phenyl)-cyclohexyloxy]-7-chloro-2H-isoquinolin-1-one,
    6-[4-(1-Amino-ethyl)-4-phenyl-cyclohexyloxy]-7-chloro-2H-isoquinolin-1-one,
    6-[4-(1-Amino-1-methyl-ethyl)-4-phenyl-cyclo-hexyloxy]-7-chloro-2H-isoquinolin-1-one,
    6-(4-[amino(cyclopropyl)methyl]-4-phenyl-cyclohexyl}oxy)-7-chloroisoquinolin-1(2H)-one,
    6-[4-(1-Amino-propyl)-4-(4-isopropyl-phenyl)-cyclohexyloxy]-7-chloro-2H-isoquinolin-1-one,
    6-[4-(1-Amino-propyl)-4-(3-methoxy)-phenye-cyclohexyloxy]-7-chloro-2H-isoquinolin-1-one,
    6-[4-(1-Amino-propyl)-4-(3-bromo-phenyl)-cyclohexyloxy]-7-chloro-2H-isoquinolin-1-one,
    6-[4-(1-Amino-2-methyl-propyl)-4-(4-fluoro-phenyl)-cyclohexyloxy]-7-chloro-2H-isoquinolin-1-one, or
    6-[4-(1-Amino-propyl)-4-phenyl-cyclohexyloxy]-4-bromo-7-chloro-2H-isoquinolin-1-one,
    their stereoisomeric and/or tautomeric forms or a pharmaceutically acceptable salt.
41. A compound according to claim 1 selected from the group consisting of
    cis-6-[4-(1-Amino-propyl)-4-(4-fluoro-phenyl)-cyclohexyloxy]-7-chloro-2H-isoquinolin-1-one,
    trans-6-[4-(1-amino-propyl)-4-(4-fluoro-phenyl)-cyclohexyloxy]-7-chloro-2H-isoquinolin-1-on,
    cis-6-[4-(1-Amino-cyclopropyl)-4-phenyl-cyclohexyloxy]-7-chloro-2H-isoquinolin-1-one,
    cis-6-{[4-(1-Amino-propyl)-4-phenylcyclohexyl]oxy}-7-chloro-2H-isoquinolin-1-one,
    trans-6-[4-(1-Amino-propyl)-4-phenyl)-cyclohexyloxy]-7-chloro-2H-isoquinolin-1-one,
    cis-6-[4-(1-Amino-butyl)-4-phenyl-cyclohexyloxy]-7-chloro-2H-isoquinolin-1-one,
    trans-6-[4-(1-Amino-butyl)-4-phenyl-cyclohexyloxy]-7-chloro-2H-isoquinolin-1-one,
    cis-6-[4-(1-Amino-butyl)-4-(4-fluoro-phenyl)-cyclohexyloxy]-7-chloro-2H-isoquinolin-1-one,
    trans-6-[4-(1-Amino-butyl)-4-(4-fluoro-phenyl)-cyclohexyloxy]-7-chloro-2H-isoquinolin-1-one,
    cis-6-[4-(1-Amino-propyl)-4-(4-bromo-phenyl)-cyclohexyloxy]-7-chloro-2H-isoquinolin-1-one,
    cis-6-[4-(1-Amino-propyl)-4-(2-bromo-phenyl)-cyclohexyloxy]-7-chloro-2H-isoquinolin-1-one,
    cis-6-[4-(1-Amino-propyl)-4-(4-trifluoromethyl-phenyl)-cyclo-hexyloxy]-7-chloro-2H-isoquinolin-1-one,
    cis-6-[4-(1-Amino-propyl)-4-(2-fluoro-phenyl)-cyclohexyloxy]-7-chloro-2H-isoquinolin-1-one,
    cis-6-[4-(1-Amino-propyl)-4-(2-chloro-phenyl)-cyclohexyloxy]-7-chloro-2H-isoquinolin-1-one,
    cis-6-[4-(1-Amino-propyl)-4-phenyl-cyclohexyloxy]-7-methyl-2H-isoquinolin-1-one,
    cis-6-[4-(1-Amino-ethyl)-4-(4-fluoro-phenyl)-cyclohexyloxy]-7-chloro-2H-isoquinolin-1-one,
    trans-6-[4-(1-Amino-ethyl)-4-(4-fluoro-phenyl)-cyclohexyloxy]-7-chloro-2H-isoquinolin-1-one,
    cis-6-[4-(1-Amino-propyl)-4-(3-bromo-phenyl)-cyclohexyloxy]-7-chloro-2H-isoquinolin-1-one,
    trans-6-[4-(1-Amino-propyl)-4-(3-bromo-phenyl)-cyclohexyloxy]-7-chloro-2H-isoquinolin-1-one,
    cis-6-[4-(1-Amino-propyl)-4-(3-methoxy)-phenyl)-cyclohexyloxy]-7-chloro-2H-isoquinolin-1-one,
    trans-6-[4-(1-Amino-propyl)-4-(3-methoxy-phenyl)-cyclohexyloxy]-7-chloro-2H-isoquinolin-1-one,
    trans-6-[4-(Amino-phenyl-methyl)-4-(4-fluoro-phenyl)-cyclohexyloxy]-7-chloro-2H-isoquinolin-1-one, trans-6-[4-(1-Amino-2-methyl-propyl)-4-phenyl-cyclohexyloxy]-7-chloro-2H-isoquinolin-1-one,
trans-6-[4-(1-Amino-3-methyl-butyl)-4-phenyl-cyclohexyloxy]-7-chloro-2H-isoquinolin-1-one,
trans-6-[4-(Amino-phenyl-methyl)-4-phenyl-cyclo-hexyloxy]-7-chloro-2H-isoquinolin-1-one,
trans-6-[4-(1-Amino-1-methyl-ethyl)-4-(4-fluoro-phenyl)-cyclohexyloxy]-7-chloro-2H-isoquinolin-1-one,
cis-6-[4-(1-Amino-cyclopropyl)-4-(2-fluoro-phenyl)-cyclohexyloxy]-7-chloro-2H-isoquinolin-1-one,
cis-6-[4-(1-Amino-ethyl)-4-phenyl-cyclohexyloxy]-7-chloro-2H-isoquinolin-1-one,
cis-6-[4-(1-Amino-1-methyl-ethyl)-4-phenyl-cyclo-hexyloxy]-7-chloro-2H-isoquinolin-1-one,
cis-6-(4-[amino(cyclopropyl)methyl]-4-phenyl-cyclohexyl}oxy)-7-chloro-2H-isoquinolin-1-one,
cis-6-[4-(1-Amino-propyl)-4-(4-isopropyl-phenyl)-cyclohexyloxy]-7-chloro-2H-isoquinolin-1-one,
cis-6-[4-(1-Amino-2-methyl-propyl)-4-(4-fluoro-phenyl)-cyclohexyloxy]-7-chloro-2H-isoquinolin-1-one, and
cis-6-[4-(1-Amino-propyl)-4-phenyl-cyclohexyloxy]-4-bromo-7-chloro-2H-isoquinolin-1-one,
their stereoisomeric and/or tautomeric forms or a pharmaceutically acceptable salt.

42. A compound according to claim 1 selected from the group consisting of
trans-6-[4-((S)-Amino-phenyl-methyl)-4-phenyl-cyclohexyloxy]-7-chloro-2H-isoquinolin-1-one,
trans-6-[4-((R)-Amino-phenyl-methyl)-4-phenyl-cyclohexyloxy]-7-chloro-2H-isoquinolin-1-one,
cis-6-[4-((S)-1-Amino-propyl)-4-phenyl-cyclohexyloxy]-7-chloro-2H-isoquinolin-1-one,
cis-6-[4-((R)-1-Amino-propyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((R)-Amino-cyclopropyl-methyl)-4-phenyl-cyclohexyloxy]-7-chloro-2H-isoquinolin-1-one,
cis-6-[4-((S)-Amino-cyclopropyl-methyl)-4-phenyl-cyclohexyloxy]-7-chloro-2H-isoquinolin-1-one,
cis-6-[4-((S)-1-Amino-ethyl)-4-phenyl-cyclohexyloxy]-7-chloro-2H-isoquinolin-1-one,
cis-6-[4-((R)-1-Amino-ethyl)-4-phenyl-cyclohexyloxy]-7-chloro-2H-isoquinolin-1-one,
6-{4-[(S)-Amino-(4-fluoro-phenyl)-methyl]-cyclohexyloxy}-7-chloro-2H-isoquinolin-1-one,
6-{4-[(R)-Amino-(4-fluoro-phenyl)-methyl]-cyclohexyloxy}-7-chloro-2H-isoquinolin-1-one,
cis-6-[4-((R)-1-Amino-propyl)-4-phenyl-cyclohexyloxy]-7-chloro-2H-isoquinolin-1-one, and
cis-6-[4-((S)-1-Amino-propyl)-4-phenyl-cyclohexyloxy]-7-chloro-2H-isoquinolin-1-one,
their tautomeric forms or a pharmaceutically acceptable salt.

43. A compound according to claim 1 selected from the group consisting of cis-6-[4-(1-Amino-propyl)-4-pyridin-2-yl-cyclohexyloxy]-7-chloro-2H-isoquinolin-1-one,
cis-6-[4-(1-Amino-propyl)-4-(2,4-difluoro-phenyl)-cyclohexyloxy]-7-chloro-2H-isoquinolin-1-one,
cis-6-[4-(1-Amino-propyl)-4-(4-fluoro-2-methyl-phenyl)cyclohexyloxy]-7-chloro-2H-isoquinolin-1-one,
cis-6-[4-(1-Amino-propyl)-4-(3,5-difluoro-phenyl)-cyclohexyloxy]-7-chloro-2H-isoquinolin-1-one,
cis-6-[4-(1-Amino-propyl)-4-(3,4-difluoro-phenyl)-cyclohexyloxy]-7-chloro-2H-isoquinolin-1-one,
cis-6-[4-(1-Amino-propyl)-4-o-tolyl-cyclohexyloxy]-7-chloro-2H-isoquinolin-1-one,
cis-6-[4-(1-Amino-propyl)-4-(2-trifluoromethoxy-phenyl)-cyclohexyloxy]-7-chloro-2H-isoquinolin-1-one,
cis-6-[4-(1-Amino-propyl)-4-(4-fluoro-3-methoxy-phenyl)-cyclohexyloxy]-7-chloro-2H-isoquinolin-1-one,
cis-6-[4-(1-Amino-propyl)-4-(3-ethoxy-phenyl)-cyclohexyloxy]-7-chloro-2H-isoquinolin-1-one,
cis-6-[4-(1-Amino-propyl)-4-(3-methoxy-4-methyl-phenyl)-cyclohexyloxy]-7-chloro-2H-isoquinolin-1-one,
cis-6-[4-(1-Amino-propyl)-4-(3,4-difluoro-phenyl)-cyclohexyloxy]-7-methyl-2H-isoquinolin-1-one,
cis-6-[4-(1-Amino-propyl)-4-(3,5-difluoro-phenyl)-cyclohexyloxy]-7-fluoro-2H-isoquinolin-1-one,
cis-6-[4-(1-Amino-propyl)-4-(3,4-difluoro-phenyl)-cyclohexyloxy]-7-fluoro-5-methyl-2H-isoquinolin-1-one,
cis-6-[4-(1-Amino-propyl)-4-(3,5-difluoro-phenyl)-cyclohexyloxy]-7-methoxy-2H-isoquinolin-1-one,
cis-6-[4-(1-Amino-propyl)-4-(2-methoxy-phenyl)-cyclohexyloxy]-7-chloro-2H isoquinolin-1-one,
cis-6-[4-(1-Amino-propyl)-4-(4-trifluoro-methoxy-phenyl)-cyclohexyloxy]-7-chloro-2H-isoquinolin-1-one,
cis-6-[4-(1-Amino-1-methyl-ethyl)-4-(4-fluoro-phenyl)-cyclohexyloxy]-7-chloro-2H-isoquinolin-1-one,
cis-6-[4-(1-Amino-propyl)-4-(3,5-difluoro-phenyl)-cyclohexyloxy]-4-benzyl-7-chloro-2H-isoquinolin-1-one,
cis-6-[4-(1-Amino-propyl)-4-(3,5-difluoro-phenyl)-cyclohexyloxy]-5-chloro-2H-isoquinolin-1-one,
cis-6-[4-(1-Amino-propyl)-4-(3,5-difluoro-phenyl)-cyclohexyloxy]-5,7-dimethyl-2H-isoquinolin-1-one,
cis-6-[4-(Amino-cyclopropyl-methyl)-4-(4-fluoro-phenyl)-cyclohexyloxy]-7-chloro-2H-isoquinolin-1-one,
cis-6-[4-(1-Amino-propyl)-4-(3-trifluoromethyl-phenyl)-cyclohexyloxy]-7-chloro-2H-isoquinolin-1-one,
cis-6-[4-(1-Amino-propyl)-4-(3-trifluoromethoxy-phenyl)-cyclohexyloxy]-7-chloro-2H-isoquinolin-1-one,
cis-6-[4-(1-Amino-propyl)-4-(3-trifluoromethoxy-phenyl)-cyclohexyloxy]-7-methyl-2H-isoquinolin-1-one,
cis-6-[4-(1-Amino-propyl)-4-(3-trifluoromethyl-phenyl)-cyclohexyloxy]-7-methyl-2H-isoquinolin-1-one,
cis-6-[4-(1-Amino-propyl)-4-phenyl-cyclohexyloxy]-7-fluoro-2H-isoquinolin-1-one,
cis-6-[4-(1-Amino-propyl)-4-phenyl-cyclohexyloxy]-7-fluoro-5-methyl-2H-isoquinolin-1-one,
cis-6-[4-(1-Amino-propyl)-4-phenyl-cyclohexyloxy]-4-benzyl-7-chloro-2H-isoquinolin-1-one,
cis-4-[1-(1-Amino-propyl)-4-(7-chloro-1-oxo-1,2-dihydro-isoquinolin-6-yloxy)-cyclohexyl]-benzonitrile,
cis-3-[1-(1-Amino-propyl)-4-(7-chloro-1-oxo-1,2-dihydro-isoquinolin-6-yloxy)-cyclohexyl]benzonitrile,
6-[cis-4-(1-Amino-propyl)-4-(3-methanesulfonyl-phenyl)-cyclohexyloxy]-7-chloro-2H-isoquinolin-1-one,
6-[(1S,4S,5S)-5-(1-Amino-propyl)-5-phenyl-bicyclo[2.2.1]hept-2-yloxy]-7-chloro-2H-isoquinolin-1-one,
6-[(1R,4R,5R)-5-(1-Amino-propyl)-5-phenyl-bicyclo[2.2.1]hept-2-yloxy]-7-chloro-2H-isoquinolin-1-one,
cis-6-[4-(1-Benzylamino-propyl)-4-phenyl-cyclohexyloxy]-7-methyl-2H-isoquinolin-1-one,
cis-6-[4-(1-Diethylamino-propyl)-4-phenyl-cyclohexyloxy]-7-methyl-2H-isoquinolin-1-one,
cis-7-Methyl-6-[4-(1-propylamino-propyl)-4-(3-trifluoromethyl-phenyl)-cyclohexyloxy]-2H-isoquinolin-1-one, cis-6-[4-(1-Benzylamino-propyl)-4-phenyl-cyclohexyloxy]-7-chloro-2H-isoquinolin-1-one,
cis-7-Chloro-6-[4-(1-isobutylamino-propyl)-4-phenyl-cyclohexyloxy]-2H-isoquinolin-1-one,
cis-6-[4-(1-Butylamino-propyl)-4-phenyl-cyclohexyloxy]-7-chloro-2H-isoquinolin-1-one,
cis-7-Chloro-6-{4-[1-(cyclopropylmethyl-amino)-propyl]-4-phenyl-cyclohexyloxy}-2H-isoquinolin-1-one,
cis-6-[4-(2-Amino-propyl)-4-(4-fluoro-phenyl)-cyclohexyloxy]-7-chloro-2H-isoquinolin-1-one,
cis-6-[4-(2-Amino-butyl)-4-(4-fluoro-phenyl)-cyclohexyloxy]-7-chloro-2H-isoquinolin-1-one,
cis-6-[4-(1-Amino-2-fluoro-ethyl)-4-(4-fluoro-phenyl)-cyclohexyloxy]-7-chloro-2H-isoquinolin-1-one,
cis-6-[4-(1-Amino-3-methoxy-propyl)-4-(4-fluoro-phenyl)-cyclohexyloxy]-7-chloro-2H-isoquinolin-1-one,
6-[3-(1-Amino-propyl)-3-(4-fluoro-phenyl)-cyclobutyloxy]-7-chloro-2H-isoquinolin-1-one, and
6-[3-(1-Amino-propyl)-3-(4-fluoro-phenyl)-cyclopentyloxy]-7-chloro-2H-isoquinolin-1-one,
and their stereoisomeric and/or tautomeric forms or a pharmaceutically acceptable salt.

44. A compound according to claim 1 is selected from the group consisting of
cis-1-[4-(7-Chloro-isoquinolin-6-yloxy)-1-(3,4-difluoro-phenyl)-cyclohexyl]-propylamine,
cis-1-[4-(7-Bromo-isoquinolin-6-yloxy)-1-(3,4-difluoro-phenyl)-cyclohexyl]-propylamine,
cis-1-[1-(3,5-Difluoro-phenyl)-4-(5,7-dimethyl-isoquinolin-6-yloxy)-cyclohexyl]-propylamine,
cis-1-[1-(3,5-Difluoro-phenyl)-4-(7-fluoro-5-methyl-isoquinolin-6-yloxy)-cyclohexyl]-propylamine,
cis-1-[1-(3,4-Difluoro-phenyl)-4-(7-fluoro-isoquinolin-6-yloxy)-cyclohexyl]-propylamine,
cis-1-[4-(7-Chloro-isoquinolin-6-yloxy)-1-(3,5-difluoro-phenyl)-cyclohexyl]-propylamine,
cis-1-[4-(5-Chloro-isoquinolin-6-yloxy)-1-(3,5-difluoro-phenyl)-cyclohexyl]-propylamine,
cis-1-[4-(7-Chloro-isoquinolin-6-yloxy)-1-phenyl-cyclohexyl]-propylamine,
cis-1-[4-(5,7-Dimethyl-isoquinolin-6-yloxy)-1-phenyl-cyclohexyl]-propylamine,
cis-1-[4-(7-Fluoro-isoquinolin-6-yloxy)-1-phenyl-cyclohexyl]-propylamine,
cis-1-[4-(5-Chloro-isoquinolin-6-yloxy)-1-phenyl-cyclohexyl]-propylamine,
cis-1-[4-(7-Fluoro-5-methyl-isoquinolin-6-yloxy)-1-phenyl-cyclohexyl]-propylamine,
cis-1-[4-(7-Bromo-isoquinolin-6-yloxy)-1-phenyl-cyclohexyl]-propylamine,
cis-1-[4-(7-Methyl-isoquinolin-6-yloxy)-1-phenyl-cyclohexyl]-propylamine,
cis-6-[4-(1-Amino-propyl)-4-phenyl-cyclohexyloxy]-7-chloro-isoquinolin-1-ylamine,
[4-(1-Amino-propyl)-4-(4-methoxy-phenyl)-cyclohexyl]-isoquinolin-6-yl-amine, and
1-Amino-[4-(1-amino-propyl)-4-(4-methoxy-phenyl)-cyclohexyl]-isoquinolin-6-yl-amine,
and their stereoisomeric and/or tautomeric forms or a pharmaceutically acceptable salt.

45. A compound according to claim 1 selected from the group consisting of
6-[4-(1-Amino-1-phenyl-ethyl)-cyclohexyloxy]-7-chloro-2H-isoquinolin-1-one,
6-{4-[Amino-(4-methoxy-phenyl)-methyl]-cyclohexyloxy}-7-chloro-2H-isoquinolin-1-one,
6-{4-[Amino-(4-fluoro-phenyl)-methyl]-cyclohexyloxy}-7-chloro-2H-isoquinolin-1-one,
6-[4-(Amino-p-tolyl-methyl)-cyclohexyloxy]-7-chloro-2H-isoquinolin-1-one, or
6-[4-(Amino-phenyl-methyl)-cyclohexyloxy]-7-chloro-2H-isoquinolin-1-one,
and their stereoisomeric and/or tautomeric forms or a pharmaceutically acceptable salt.

46. A compound according to claim 1 is selected from the group consisting of
6-{4-[1-Amino-1-(4-fluoro-phenyl)-ethyl]cyclohexyloxy}-7-chloro-2H-isoquinolin-1-one,
6-{4-[1-Amino-1-(4-methoxy-phenyl)-ethyl]-cyclohexyloxy}-7-chloro-2H-isoquinolin-1-one,
6-{4-[1-Amino-1-cyclopentyl-ethyl]-cyclohexyloxy}-7-chloro-2H-isoquinolin-1-one,
6-{4-[1-Amino-1-ethyl-propyl]-cyclohexyloxy}-7-chloro-2H-isoquinolin-1-one,
6-{4-[1-Amino-1-cyclopropyl-ethyl]-cyclohexyloxy}-7-chloro-2H-isoquinolin-1-one,
6-{4-[1-Amino-1-n-propyl-ethyl]-cyclohexyloxy}-7-chloro-2H-isoquinolin-1-one,
6-[4-(1-Amino-propyl)-cyclohexyloxy]-7-chloro-2H-isoquinolin-1-one, and
6-[4-(Amino-cyclopropyl-methyl)-cyclohexyloxy]-7-chloro-2H-isoquinolin-1-one,
and their stereoisomeric and/or tautomeric forms or a pharmaceutically acceptable salt.

47. A method for the treatment and/or prevention of hypertension, pulmonary hypertension, ocular hypertension, retinopathy, glaucoma, peripheral circulatory disorder, peripheral arterial occlusive disease (PAOD), coronary heart disease, angina pectoris, heart hypertrophy, heart failure, ischemic diseases, ischemic organ failure (end organ damage), fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy, infection of digestive tracts with bacteria, sepsis or cancer development and progression comprising administering to a patient in need thereof a therapeutically effective amount of a compound of formula (I) or a pharmaceutically acceptable salt thereof according to any one of claims 1 to 4.

48. A method for the treatment and/or prevention of hypertension, pulmonary hypertension, fibroid liver, liver failure, nephropathy, renal failure, chronic obstructive pulmonary disease (COPD), cerebral vasospasm, pain, spinal cord injury, erectile dysfunction, blood vessel restenosis, or cancer development and progression comprising administering to a patient in need thereof a therapeutically effective amount of a compound of formula (I) or a pharmaceutically acceptable salt thereof according to any one of claims 1 to 4.

49. A method for curative approaches associated with stem cell or induced pluripotent stem cell treatment, improvement of recognition or for treatment or prevention of depression, epilepsy, fibroid heart, renal papillary necrosis, tubulo-interstitial dysfunction, multiple sclerosis, vessel stenosis or lipid disorders comprising administering to a patient in need thereof a therapeutically effective amount of a compound of formula (I) or a pharmaceutically acceptable salt thereof according to any one of claims 1 to 4.

50. A pharmaceutical composition comprising an effective amount of at least one compound of formula (I) or a pharmacologically acceptable salt according to one of claims 1 to 4, pharmaceutically tolerated excipients and carriers and, further additives and/or other active ingredients.

* * * * *